(12) United States Patent
Lv et al.

(10) Patent No.: US 12,304,967 B2
(45) Date of Patent: *May 20, 2025

(54) FUSION PROTEIN AND USE THEREOF

(71) Applicants: HANGZHOU SUMGEN BIOTECH CO., LTD., Hangzhou (CN); SUMGEN MAB (BEIJING) BIOTECH CO., LTD., Beijing (CN)

(72) Inventors: Ming Lv, Hangzhou (CN); Xiaoran Ding, Hangzhou (CN); Shiwei Miao, Hangzhou (CN); Bin Tan, Hangzhou (CN); Xuegong Wang, Hangzhou (CN)

(73) Assignees: HANGZHOU SUMGEN BIOTECH CO., LTD., Hangzhou (CN); SUMGEN MAB (BEIJING) BIOTECH CO., LTD., Beijing (CN)

( * ) Notice: Subject to any disclaimer, the term of this patent is extended or adjusted under 35 U.S.C. 154(b) by 1039 days.

This patent is subject to a terminal disclaimer.

(21) Appl. No.: 17/293,729

(22) PCT Filed: Nov. 13, 2019

(86) PCT No.: PCT/CN2019/117856
§ 371 (c)(1),
(2) Date: May 13, 2021

(87) PCT Pub. No.: WO2020/098672
PCT Pub. Date: May 22, 2020

(65) Prior Publication Data
US 2021/0317230 A1  Oct. 14, 2021

(30) Foreign Application Priority Data
Nov. 14, 2018  (CN) .......................... 201811356690.9

(51) Int. Cl.
C07K 16/30 (2006.01)
A61K 38/00 (2006.01)
A61K 39/00 (2006.01)
A61P 35/00 (2006.01)
C07K 16/28 (2006.01)

(52) U.S. Cl.
CPC .............. C07K 16/30 (2013.01); A61P 35/00 (2018.01); C07K 16/2803 (2013.01); C07K 16/2863 (2013.01); C07K 16/2896 (2013.01); A61K 38/00 (2013.01); A61K 2039/505 (2013.01); C07K 2317/565 (2013.01); C07K 2319/30 (2013.01)

(58) Field of Classification Search
CPC .............. C07K 16/30; C07K 16/2803; C07K 16/2863; C07K 16/2896; C07K 2317/565; C07K 2319/30; A61P 35/00; A61K 38/00; A61K 2039/505
See application file for complete search history.

(56) References Cited

U.S. PATENT DOCUMENTS

| 7,829,673 B2 * | 11/2010 | De Weers | C12N 5/10 424/139.1 |
|---|---|---|---|
| 10,087,257 B2 | 10/2018 | Majeti et al. | |
| 10,259,859 B2 | 4/2019 | Pons et al. | |
| 10,487,150 B2 | 11/2019 | Majeti et al. | |
| 11,891,423 B2 * | 2/2024 | Lv | C07K 14/70596 |
| 2016/0177276 A1 | 6/2016 | Lo et al. | |
| 2016/0367663 A1 * | 12/2016 | Doshi | A61P 35/02 |
| 2017/0107270 A1 | 4/2017 | Pons et al. | |
| 2017/0121414 A1 * | 5/2017 | Jansson | A61K 47/22 |
| 2019/0169266 A1 | 6/2019 | Pons et al. | |

FOREIGN PATENT DOCUMENTS

| CN | 107108748 A | 8/2017 | |
|---|---|---|---|
| CN | 108350048 A | 7/2018 | |
| EA | 201100947 A1 | 2/2012 | |
| WO | WO 2013/109752 A1 | 7/2013 | |
| WO | WO 2016/022971 A1 | 2/2016 | |
| WO | WO 2016/024021 A1 | 2/2016 | |
| WO | WO 2017/027422 A1 | 2/2017 | |
| WO | WO 2018/014067 A1 | 1/2018 | |
| WO | WO-2019154421 A1 * | 8/2019 | ........... A61K 31/713 |
| WO | WO-2019201236 A1 * | 10/2019 | ........... A61K 38/00 |

OTHER PUBLICATIONS

Schroeder and Cavacini (Journal of Allergy and Clinical Immunology (2010) 125(2, Suppl.2): S41-S52) (Year: 2010).*
Sela-Culang et al. (Frontiers in Immunology (2013) 4: 302) (Year: 2013).*
Lv et al. U.S. Appl. No. 17/599,733. Fusion Protein and Use Thereof. (Year: 2021).*
Lv et al. U.S. Appl. No. 18/713,352. Fusion Protein Comprising SIRPA Mutant. (Year: 2024).*
Extended European Search Report issued Jul. 5, 2022 in European Patent Application No. 19884036.5, 9 pages.
Piccione, E.C., et al., "SIRPα-Antibody Fusion Proteins Selectivity Bind and Eliminate Dual Antigen-Expressing Tumor Cells", Clinical Cancer Research, vol. 22, No. 20, Apr. 28, 2016, XP055467921, pages.

(Continued)

*Primary Examiner* — Brad Duffy
*Assistant Examiner* — Elizabeth A Shupe
(74) *Attorney, Agent, or Firm* — Merchant & Gould P.C.; Daniel J. Pereira

(57) ABSTRACT

Provided is a fusion protein, comprising a first binding domain that specifically binds a tumor-associated antigen, and a second binding domain that specifically binds a CD47 protein, wherein the second binding domain comprises a mutant of a human SIRPα variant 1. Also provided are an immunoconjugate, nucleic acid molecules, vectors, compositions, and cells related to the fusion protein and preparation methods therefor, and the uses thereof in the preparation of medicaments.

16 Claims, 10 Drawing Sheets
Specification includes a Sequence Listing.

(56) References Cited

OTHER PUBLICATIONS

Weiskopf, K.., et al., "Engineered SIRPα Variants as Immunotherapeutic Adjuvants to Anticancer Antibodies", Science, vol. 341, No. 6141, May 30, 2013, XP055223925, pp. 88-91.
Ponce, L.P., et al., "SIRPα-Antibody fusion proteins stimulate phagocytosis and promote elimination of acute myeloid leukemia cells", Oncotarget, Retrieved from the Internet: URL:https:///www.ncbi.nlm.nih.gov/pmc/articles/PMC5355265/pdf/oncotarget-08-11284.pdf, Feb. 14, 2017, XP055549877, pp. 11284-11301.
International Search Report issued on Feb. 19, 2020 in PCT/CN2019/117856 filed on Nov. 13, 2019, 4 pages.

* cited by examiner

SEQUENCE LISTING

```
<160> NUMBER OF SEQ ID NOS: 78

<210> SEQ ID NO 1
<211> LENGTH: 15
<212> TYPE: PRT
<213> ORGANISM: Artificial Sequence
<220> FEATURE:
```

<223> OTHER INFORMATION: LCDR1 of SG003

<400> SEQUENCE: 1

Arg Ala Ser Ser Ser Val Ser Ser Ser Ala Phe Ser Tyr Val His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: LCDR2 of SG003

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: LCDR3 of SG003

<400> SEQUENCE: 3

His His Ser Arg Glu Leu Pro Phe Thr
1               5

<210> SEQ ID NO 4
<211> LENGTH: 5
<212> TYPE: PRT
<213> ORGANISM: Artificial Sequence
<220> FEATURE:
<223> OTHER INFORMATION: HCDR1 of SG003

<400> SEQUENCE: 4

Leu Tyr Trp Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: HCDR2 of SG003

<400> SEQUENCE: 5

Lys Ile Asn Pro Asp Ser Ser Thr Ile Asn Tyr Thr Pro Ser Leu Lys
1               5                   10                  15

Asp

<210> SEQ ID NO 6
<211> LENGTH: 10
<212> TYPE: PRT
<213> ORGANISM: Artificial Sequence
<220> FEATURE:
<223> OTHER INFORMATION: HCDR3 of SG003

<400> SEQUENCE: 6

Leu Trp Ile Ala Thr Gly Gly Phe Asp Tyr
1               5                   10

<210> SEQ ID NO 7
<211> LENGTH: 111
<212> TYPE: PRT
<213> ORGANISM: Artificial Sequence

```
<220> FEATURE:
<223> OTHER INFORMATION: VL of SG003

<400> SEQUENCE: 7

Glu Ile Val Met Thr Gln Ser Pro Ala Ser Leu Ser Ala Ser Leu Gly
1               5                   10                  15

Gln Arg Ala Thr Ile Ser Cys Arg Ala Ser Ser Val Ser Ser Ser
            20                  25                  30

Ala Phe Ser Tyr Val His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Leu Pro Phe Thr Phe Gly Ser Gly Thr Lys Leu Glu Ile Lys
            100                 105                 110

<210> SEQ ID NO 8
<211> LENGTH: 119
<212> TYPE: PRT
<213> ORGANISM: Artificial Sequence
<220> FEATURE:
<223> OTHER INFORMATION: VH of SG003

<400> SEQUENCE: 8

Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Asn Pro Asp Ser Ser Thr Ile Asn Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Phe Asp Tyr Trp Gly Gln Gly
            100                 105                 110

Thr Thr Leu Thr Val Ser Ser
        115

<210> SEQ ID NO 9
<211> LENGTH: 333
<212> TYPE: DNA
<213> ORGANISM: Artificial Sequence
<220> FEATURE:
<223> OTHER INFORMATION: Nucleic acid encoding VL of SG003

<400> SEQUENCE: 9
gagatcgtga tgacccagag ccctgccagc ctgagcgcca gcctgggcca gagggccacc        60
atcagctgca gggccagcag cagcgtgagc agcagcgcct tcagctacgt gcactggtac       120
cagcagaaga gcggccagcc tcctaagctg ctgatctacc tggccagcaa cctggagagc       180
ggcgtgcctg ccaggttcag cggcagcggc agcggcaccg acttcaccct gaccatccac       240
cctgtggaga gcgaggacgt ggccacctac tactgccacc acagcaggga gctgcctttc       300
```
accttcggca gcggcaccaa gctggagatc aag    333

<210> SEQ ID NO 10
<211> LENGTH: 357
<212> TYPE: DNA
<213> ORGANISM: Artificial Sequence
<220> FEATURE:
<223> OTHER INFORMATION: Nucleic acid encoding VH ofSG003

<400> SEQUENCE: 10
caggtgcagc tgctggagag cggcggcggc ctggtgcagc ctggcggcag cctgaagctg    60
agctgcgtgg ccagcggctt cgacttcagc ctgtactgga tgaactgggt gaggcaggcc    120
cctggcaagg gcctggagtg gatcggcaag atcaaccctg acagcagcac catcaactac    180 accctagcc tgaaggacaa gttcttcatc agcagggaca cgccaagaa caccctgtac    240 ctgcagatga ccaaggtgag gagcgaggac accgccctgt actactgcgc caggctgtgg    300
atcgccaccg gcggcttcga ctactggggc cagggcacca ccctgaccgt gagcagc    357

<210> SEQ ID NO 11
<211> LENGTH: 218
<212> TYPE: PRT
<213> ORGANISM: Artificial Sequence
<220> FEATURE:
<223> OTHER INFORMATION: Light chain of SG003

<400> SEQUENCE: 11

Glu Ile Val Met Thr Gln Ser Pro Ala Ser Leu Ser Ala Ser Leu Gly
1               5                   10                  15

Gln Arg Ala Thr Ile Ser Cys Arg Ala Ser Ser Val Ser Ser Ser
            20                  25                  30

Ala Phe Ser Tyr Val His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Leu Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 12

<211> LENGTH: 657
<212> TYPE: DNA
<213> ORGANISM: Artificial Sequence
<220> FEATURE:
<223> OTHER INFORMATION: Nucleic acid encoding light chain of SG003

<400> SEQUENCE: 12

```
gagatcgtga tgacccagag ccctgccagc ctgagcgcca gcctgggcca gagggccacc      60
atcagctgca gggccagcag cagcgtgagc agcagcgcct tcagctacgt gcactggtac     120
cagcagaaga gcggccagcc tcctaagctg ctgatctacc tggccagcaa cctggagagc     180
ggcgtgcctg ccaggttcag cggcagcggc agcggcaccg acttcaccct gaccatccac     240
cctgtggaga gcgaggacgt ggccacctac tactgccacc agcagggga gctgcctttc      300
accttcggca gcggcaccaa gctggagatc aagcgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgttag         657
```

<210> SEQ ID NO 13
<211> LENGTH: 449
<212> TYPE: PRT
<213> ORGANISM: Artificial Sequence
<220> FEATURE:
<223> OTHER INFORMATION: Heavy chain of SG003

<400> SEQUENCE: 13

```
Gln Val Gln Leu Leu Glu Ser Gly Gly Gly Leu Val Gln Pro Gly Gly
 1               5                  10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Asn Pro Asp Ser Ser Thr Ile Asn Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
    275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Thr Lys Asn Gln Val Ser Leu Thr
    355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
    435                 440                 445
Lys

<210> SEQ ID NO 14
<211> LENGTH: 1350
<212> TYPE: DNA
<213> ORGANISM: Artificial Sequence
<220> FEATURE:
<223> OTHER INFORMATION: Nucleic acid encoding heavy chain of SG003

<400> SEQUENCE: 14
caggtgcagc tgctggagag cggcggcggc ctggtgcagc ctggcggcag cctgaagctg      60
agctgcgtgg ccagcggctt cgacttcagc ctgtactgga tgaactgggt gaggcaggcc     120
cctggcaagg gcctggagtg gatcggcaag atcaaccctg acagcagcac catcaactac     180 accccctagcc tgaaggacaa gttcttcatc agcagggaca cgccaagaa caccctgtac     240 ctgcagatga ccaaggtgag gagcgaggac accgccctgt actactgcgc caggctgtgg     300
atcgccaccg gcggcttcga ctactggggc cagggcacca ccctgaccgt gagcagcgct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660

```
tcttgtgaca aaactcacac atgcccaccg tgcccagcac ctgaactcct ggggggaccg    720
tcagtcttcc tcttcccccc aaaacccaag acaccctca tgatctcccg gacccctgag    780
gtcacgtgcg tggtggtgga cgtgagccac gaagaccccg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

```
<210> SEQ ID NO 15
<211> LENGTH: 22
<212> TYPE: PRT
<213> ORGANISM: Artificial Sequence
<220> FEATURE:
<223> OTHER INFORMATION: Binding epitope of CD38 protein

<400> SEQUENCE: 15

Ser Thr Phe Gly Ser Val Glu Val His Asn Leu Gln Pro Glu Lys Val
1               5                   10                  15

Gln Thr Leu Glu Ala Trp
            20

<210> SEQ ID NO 16
<211> LENGTH: 218
<212> TYPE: PRT
<213> ORGANISM: Artificial Sequence
<220> FEATURE:
<223> OTHER INFORMATION: Mutant light chain 1 of SG003

<400> SEQUENCE: 16

Glu Ile Val Met Thr Gln Ser Pro Ala Ser Leu Ser Ala Ser Leu Gly
1               5                   10                  15

Gln Arg Ala Ser Ile Ser Cys Arg Ala Ser Asn Ser Val Ser Ser
            20                  25                  30

Ala Tyr Ser Tyr Val His Trp Tyr Gln Gln Lys Ser Gly Gln Pro Pro
        35                  40                  45

Lys Leu Leu Ile Tyr Leu Ala Ser Asn Ile Gln Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Gln Leu Pro Ser Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 17
<211> LENGTH: 449
<212> TYPE: PRT
<213> ORGANISM: Artificial Sequence
<220> FEATURE:
<223> OTHER INFORMATION: Mutant heavy chain 1 of SG003

<400> SEQUENCE: 17

Gln Val Gln Leu Leu Glu Ser Gly Gly Gly Leu Val Gln Pro Gly Gly
1               5                   10                  15

Ser Leu Lys Leu Ser Cys Val Ala Ser Gly Tyr Asn Phe Ser Leu Tyr
            20                  25                  30

Tyr Met Asn Trp Val Arg Gln Ala Pro Gly Lys Gly Leu Glu Trp Ile
            35                  40                  45

Gly Lys Ile Gln Pro Glu Ser Ser Thr Ile Gln Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
            85                  90                  95

Ala Arg Leu Trp Ile Gly Ser Gly Gly Phe Asp Tyr Trp Gly Gln Gly
            100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 18
<211> LENGTH: 218
<212> TYPE: PRT
<213> ORGANISM: Artificial Sequence
<220> FEATURE:
<223> OTHER INFORMATION: Mutant light chain 2 of SG003

<400> SEQUENCE: 18

Glu Ile Val Met Thr Gln Ser Pro Ala Ser Leu Ser Ala Ser Leu Gly
1               5                   10                  15

Gln Arg Ala Thr Ile Ser Cys Arg Ala Ser Ser Ser Val Ser Ser Ser
            20                  25                  30

Ala Tyr Ser Tyr Val His Trp Tyr Gln Gln Lys Ser Gly Gln Pro Pro
        35                  40                  45

Lys Leu Leu Ile Tyr Leu Ala Ser Asp Leu Gln Ser Gly Val Pro Ala
    50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Leu Pro Tyr Ser Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 19
<211> LENGTH: 449
<212> TYPE: PRT
<213> ORGANISM: Artificial Sequence
<220> FEATURE:
<223> OTHER INFORMATION: Mutant heavy chain 2 of SG003

<400> SEQUENCE: 19

Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Ser Pro Asn Ser Ser Thr Ile Asn Tyr Ser Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Tyr Ile Ala Ser Gly Gly Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 20
<211> LENGTH: 218
<212> TYPE: PRT
<213> ORGANISM: Artificial Sequence
<220> FEATURE:
<223> OTHER INFORMATION: Mutant light chain 3 of SG003

<400> SEQUENCE: 20

Glu Ile Val Met Thr Gln Ser Pro Ala Ser Leu Ser Ala Ser Leu Gly
1               5                   10                  15

Gln Arg Ala Thr Ile Ser Cys Arg Ala Ser Asn Ser Val Ser Thr Ser
            20                  25                  30

Ala Phe Ser Tyr Val His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Thr Ile His
65                  70                  75                  80

Pro Val Glu Ser Glu Asp Val Ala Thr Tyr Tyr Cys His His Ser Arg
                85                  90                  95

Glu Val Pro Phe Thr Phe Gly Ser Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 449
<212> TYPE: PRT
<213> ORGANISM: Artificial Sequence
<220> FEATURE:
<223> OTHER INFORMATION: Mutant heavy chain 3 of SG003
```

<400> SEQUENCE: 21

```
Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Ser Pro Asp Ser Ser Leu Asn Tyr Thr Pro Ser Val
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Tyr Asn Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                    405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 22
<211> LENGTH: 16
<212> TYPE: PRT
<213> ORGANISM: Artificial Sequence
<220> FEATURE:
<223> OTHER INFORMATION: LCDR1 of C6G12

<400> SEQUENCE: 22

Arg Ser Ser Arg Ser Leu Leu His Ser Asn Gly Phe Thr Tyr Leu Tyr
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: LCDR2 of C6G12

<400> SEQUENCE: 23

Gln Met Ser Asn Leu Ala Ser
1               5

<210> SEQ ID NO 24
<211> LENGTH: 9
<212> TYPE: PRT
<213> ORGANISM: Artificial Sequence
<220> FEATURE:
<223> OTHER INFORMATION: LCDR3 of C6G12

<400> SEQUENCE: 24

Gly Gln Asn Leu Glu Leu Pro Leu Thr
1               5

<210> SEQ ID NO 25
<211> LENGTH: 6
<212> TYPE: PRT
<213> ORGANISM: Artificial Sequence
<220> FEATURE:
<223> OTHER INFORMATION: HCDR1 of C6G12

<400> SEQUENCE: 25

Ser Gly Tyr Tyr Trp Asn
1               5

<210> SEQ ID NO 26
<211> LENGTH: 16
<212> TYPE: PRT
<213> ORGANISM: Artificial Sequence
<220> FEATURE:
<223> OTHER INFORMATION: HCDR2 of C6G12

<400> SEQUENCE: 26

Tyr Arg Ser Tyr Asp Gly Ser Asn Asn Tyr Asn Pro Ser Leu Lys Asn
1               5                   10                  15

<210> SEQ ID NO 27
<211> LENGTH: 10
<212> TYPE: PRT
```

<213> ORGANISM: Artificial Sequence
<220> FEATURE:
<223> OTHER INFORMATION: HCDR3 of C6G12

<400> SEQUENCE: 27

Gly Trp Leu Leu His Tyr Thr Met Asp Tyr
1               5                   10

<210> SEQ ID NO 28
<211> LENGTH: 112
<212> TYPE: PRT
<213> ORGANISM: Artificial Sequence
<220> FEATURE:
<223> OTHER INFORMATION: VL of C6G12

<400> SEQUENCE: 28

Glu Leu Val Met Thr Gln Ser Pro Phe Ser Asn Ala Val Thr Leu Gly
1               5                   10                  15

Thr Ser Ala Ser Ile Ser Cys Arg Ser Ser Arg Ser Leu Leu His Ser
            20                  25                  30

Asn Gly Phe Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Gln Gln Asn
                85                  90                  95

Leu Glu Leu Pro Leu Thr Phe Gly Ala Gly Thr Lys Leu Glu Leu Lys
            100                 105                 110

<210> SEQ ID NO 29
<211> LENGTH: 119
<212> TYPE: PRT
<213> ORGANISM: Artificial Sequence
<220> FEATURE:
<223> OTHER INFORMATION: VH of C6G12

<400> SEQUENCE: 29

Gln Val Gln Leu Lys Gln Ser Gly Pro Gly Leu Val Lys Pro Ser Gln
1               5                   10                  15

Ser Leu Ser Leu Thr Cys Ser Val Thr Gly Phe Ser Ile Ser Ser Gly
            20                  25                  30

Tyr Tyr Trp Asn Trp Ile Arg Gln Phe Pro Gly Asn Lys Leu Glu Trp
        35                  40                  45

Met Gly Tyr Arg Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Trp Leu Leu His Tyr Thr Met Asp Tyr Trp Gly Gln Gly
            100                 105                 110

Thr Ser Val Thr Val Ser Ser
        115

<210> SEQ ID NO 30
<211> LENGTH: 336
<212> TYPE: DNA
<213> ORGANISM: Artificial Sequence

```
<220> FEATURE:
<223> OTHER INFORMATION: Nucleic acid ancoding VL of C6G12

<400> SEQUENCE: 30
gagctcgtga tgacacagtc tccattctcc aatgcagtca ctcttggaac atcagcttcc      60
atctcctgca ggtctagtag gagtctccta catagtaatg gcttcactta tttgtattgg     120
tatctgcaga agccaggcca gtctcctcag ctcctgattt atcagatgtc aaccttgcc      180 tcaggagtcc cagacaggtt cagtagcagt gggtcaggaa ctgatttcac actgagaatc     240
agcagagtgg aggctgagga tgtgggtgtt tattactgtg gtcaaaatct agagcttccg     300
ctcacgttcg gtgctgggac caagctggag ctgaaa                               336

<210> SEQ ID NO 31
<211> LENGTH: 357
<212> TYPE: DNA
<213> ORGANISM: Artificial Sequence
<220> FEATURE:
<223> OTHER INFORMATION: Nucleic acid ancoding VH of C6G12

<400> SEQUENCE: 31
caggtgcagc tgaagcagtc aggacctggc ctcgtgaaac cttctcagtc tctgtctctc      60
acctgttctg tcactggctt ctccatcagc agtggttatt actggaactg gatccggcag     120
tttccaggaa acaaactgga atggatgggc tacagaagct acgacggttc caataactac     180
aacccatctc tcaaaaatcg aatctccatc actcgtgaca catctaagaa ccagtttttc     240
ctgaagttga attctgtgac aactgaggac acagctacat attactgtgc aagaggatgg     300
ttactgcatt atactatgga ctactggggt caaggaacct cagtcaccgt ctcctca        357

<210> SEQ ID NO 32
<211> LENGTH: 219
<212> TYPE: PRT
<213> ORGANISM: Artificial Sequence
<220> FEATURE:
<223> OTHER INFORMATION: Light chain of C6G12

<400> SEQUENCE: 32

Glu Leu Val Met Thr Gln Ser Pro Phe Ser Asn Ala Val Thr Leu Gly
1               5                   10                  15

Thr Ser Ala Ser Ile Ser Cys Arg Ser Ser Arg Ser Leu Leu His Ser
            20                  25                  30

Asn Gly Phe Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Gly Gln Asn
                85                  90                  95

Leu Glu Leu Pro Leu Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 33
<211> LENGTH: 660
<212> TYPE: DNA
<213> ORGANISM: Artificial Sequence
<220> FEATURE:
<223> OTHER INFORMATION: Nucleic acid ancoding light chain of C6G12

<400> SEQUENCE: 33
gagctcgtga tgacacagtc tccattctcc aatgcagtca ctcttggaac atcagcttcc     60
atctcctgca ggtctagtag gagtctccta catagtaatg cttcactta tttgtattgg    120 tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg gtcaaaatct agagcttccg    300
ctcacgttcg gtgctgggac caagctggag ctgaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

<210> SEQ ID NO 34
<211> LENGTH: 449
<212> TYPE: PRT
<213> ORGANISM: Artificial Sequence
<220> FEATURE:
<223> OTHER INFORMATION: Heavy chain of C6G12

<400> SEQUENCE: 34

Gln Val Gln Leu Lys Gln Ser Gly Pro Gly Leu Val Lys Pro Ser Gln
1               5                   10                  15

Ser Leu Ser Leu Thr Cys Ser Val Thr Gly Phe Ser Ile Ser Ser Gly
            20                  25                  30

Tyr Tyr Trp Asn Trp Ile Arg Gln Phe Pro Gly Asn Lys Leu Glu Trp
        35                  40                  45

Met Gly Tyr Arg Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Trp Leu Leu His Tyr Thr Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 35
<211> LENGTH: 1350
<212> TYPE: DNA
<213> ORGANISM: Artificial Sequence
<220> FEATURE:
<223> OTHER INFORMATION: Nucleic acid ancoding heavy chain of C6G12

<400> SEQUENCE: 35
caggtgcagc tgaagcagtc aggacctggc ctcgtgaaac cttctcagtc tctgtctctc      60
acctgttctg tcactggctt ctccatcagc agtggttatt actggaactg gatccggcag     120
tttccaggaa acaaactgga atggatgggc tacagaagct acgacggttc caataactac     180
aacccatctc tcaaaaatcg aatctccatc actcgtgaca catctaagaa ccagttttc      240

-continued

```
ctgaagttga attctgtgac aactgaggac acagctacat attactgtgc aagaggatgg    300
ttactgcatt atactatgga ctactggggt caaggaacct cagtcaccgt ctcctcagct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacgtgcg tggtggtgga cgtgagccac gaagaccccg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

<210> SEQ ID NO 36
<211> LENGTH: 11
<212> TYPE: PRT
<213> ORGANISM: Artificial Sequence
<220> FEATURE:
<223> OTHER INFORMATION: LCDR1 of SG701

<400> SEQUENCE: 36

Arg Ala Ser Gln Gly Ile Ser Ser Trp Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: LCDR2 of SG701

<400> SEQUENCE: 37

Asp Ala Ser Asn Leu Glu Ala
1               5

<210> SEQ ID NO 38
<211> LENGTH: 9
<212> TYPE: PRT
<213> ORGANISM: Artificial Sequence
<220> FEATURE:
<223> OTHER INFORMATION: LCDR3 of SG701

<400> SEQUENCE: 38

Gln Gln Tyr Gly Asp Phe Pro Leu Thr
1               5

<210> SEQ ID NO 39

```
<211> LENGTH: 5
<212> TYPE: PRT
<213> ORGANISM: Artificial Sequence
<220> FEATURE:
<223> OTHER INFORMATION: HCDR1 of SG701

<400> SEQUENCE: 39

Asn Asn Tyr Ile His
1               5

<210> SEQ ID NO 40
<211> LENGTH: 17
<212> TYPE: PRT
<213> ORGANISM: Artificial Sequence
<220> FEATURE:
<223> OTHER INFORMATION: HCDR2 of SG701

<400> SEQUENCE: 40

Met Ile Asn Pro Ser Gly Gly Ser Thr Thr Tyr Ala Gln Lys Phe Gln
1               5                   10                  15

Gly

<210> SEQ ID NO 41
<211> LENGTH: 18
<212> TYPE: PRT
<213> ORGANISM: Artificial Sequence
<220> FEATURE:
<223> OTHER INFORMATION: HCDR3 of SG701

<400> SEQUENCE: 41

Ala Ala Leu Ser Tyr Tyr Ser Ile Val Thr Ala Lys Asp Tyr Gly Met
1               5                   10                  15

Asp Val

<210> SEQ ID NO 42
<211> LENGTH: 107
<212> TYPE: PRT
<213> ORGANISM: Artificial Sequence
<220> FEATURE:
<223> OTHER INFORMATION: VL of SG701

<400> SEQUENCE: 42

Asp Ile Gln Leu Thr Gln Ser Pro Ser Ser Val Ser Ala Ser Val Gly
1               5                   10                  15

Asp Arg Val Asn Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Ala Gly Val Pro Ser Arg Phe Arg Gly
    50                  55                  60

Ser Gly Ser Gly Thr Asp Phe Thr Phe Thr Ile Thr Ser Leu Gln Pro
65                  70                  75                  80

Glu Asp Ile Ala Thr Tyr Phe Cys Gln Gln Tyr Gly Asp Phe Pro Leu
                85                  90                  95

Thr Phe Gly Gln Gly Thr Lys Leu Glu Ile Lys
            100                 105

<210> SEQ ID NO 43
<211> LENGTH: 127
<212> TYPE: PRT
<213> ORGANISM: Artificial Sequence
<220> FEATURE:
<223> OTHER INFORMATION: VH of SG701
```

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Tyr Ile His Trp Val Arg Gln Ala Pro Gly Gln Gly Leu Glu Trp Met
        35                  40                  45

Gly Met Ile Asn Pro Ser Gly Ser Thr Thr Tyr Ala Gln Lys Phe
50                  55                  60

Gln Gly Arg Leu Thr Met Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Ala Ala Leu Ser Tyr Tyr Ser Ile Val Thr Ala Lys Asp Tyr
            100                 105                 110

Gly Met Asp Val Trp Gly Gln Gly Thr Thr Val Thr Val Ser Ser
        115                 120                 125

<210> SEQ ID NO 44
<211> LENGTH: 321
<212> TYPE: DNA
<213> ORGANISM: Artificial Sequence
<220> FEATURE:
<223> OTHER INFORMATION: Nucleic acid ancoding VL of SG701

<400> SEQUENCE: 44
gacatccagc tgacccagag ccctagcagc gtgagcgcca gcgtgggcga cagggtgaac        60
atcacctgca gggccagcca gggcatcagc agctggctgg cctggtacca gcagaagcct       120
ggcaaggccc ctaagctgct gatctacgac gccagcaacc tggaggccgg cgtgcctagc       180
aggttcaggg gcagcggcag cggcaccgac ttcaccttca ccatcaccag cctgcagcct       240
gaggacatcg ccacctactt ctgccagcag tacggcgact ccctctctga cttcggccag       300
ggcaccaagc tggagatcaa g                                                 321

<210> SEQ ID NO 45
<211> LENGTH: 381
<212> TYPE: DNA
<213> ORGANISM: Artificial Sequence
<220> FEATURE:
<223> OTHER INFORMATION: Nucleic acid ancoding VH of SG701

<400> SEQUENCE: 45
caggtgcagc tggtgcagag cggcgccgag gtgaagaagc ctggcgccag cgtgaaggtg        60
agctgcaagg ccagcggcta caccttcacc aacaactaca tccactgggt gaggcaggcc       120
cctggccagg gcctggagtg gatgggcatg atcaacccta gcggcggcag caccacctac       180
gcccagaagt tccagggcag gctgaccatg accaggdaca ccagcaccag caccgtgtac       240
atggacctga gcagcctgag gagcgaggac accgccgtgt actactgcgc cagggccgcc       300
ctgagctact acagcatcgt gaccgccaag gactacggca tggacgtgtg gggccagggc       360
accaccgtga ccgtgagcag c                                                 381

<210> SEQ ID NO 46
<211> LENGTH: 214
<212> TYPE: PRT
<213> ORGANISM: Artificial Sequence
<220> FEATURE:

<223> OTHER INFORMATION: Light tchain of SG701

<400> SEQUENCE: 46

Asp Ile Gln Leu Thr Gln Ser Pro Ser Ser Val Ala Ser Val Gly
1               5                   10                  15

Asp Arg Val Asn Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Ala Gly Val Pro Ser Arg Phe Arg Gly
    50                  55                  60

Ser Gly Ser Gly Thr Asp Phe Thr Phe Thr Ile Thr Ser Leu Gln Pro
65                  70                  75                  80

Glu Asp Ile Ala Thr Tyr Phe Cys Gln Gln Tyr Gly Asp Phe Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 645
<212> TYPE: DNA
<213> ORGANISM: Artificial Sequence
<220> FEATURE:
<223> OTHER INFORMATION: Nucleic acid ancoding light chain of SG701

<400> SEQUENCE: 47
gacatccagc tgacccagag ccctagcagc gtgagcgcca gcgtgggcga cagggtgaac      60
atcacctgca gggccagcca gggcatcagc agctggctgg cctggtacca gcagaagcct     120
ggcaaggccc ctaagctgct gatctacgac gccagcaacc tggaggccgg cgtgcctagc     180
aggttcaggg gcagcggcag cggcaccgac ttcaccttca ccatcaccag cctgcagcct     240
gaggacatcg ccacctactt ctgccagcag tacggcgact ccctctgac cttcggccag      300 ggcaccaagc tggagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

-continued

```
<210> SEQ ID NO 48
<211> LENGTH: 457
<212> TYPE: PRT
<213> ORGANISM: Artificial Sequence
<220> FEATURE:
<223> OTHER INFORMATION: Heavy chain of SG701

<400> SEQUENCE: 48
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Tyr Ile His Trp Val Arg Gln Ala Pro Gly Gln Gly Leu Glu Trp Met
        35                  40                  45

Gly Met Ile Asn Pro Ser Gly Gly Ser Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Ala Ala Leu Ser Tyr Tyr Ser Ile Val Thr Ala Lys Asp Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 49
<211> LENGTH: 1374
<212> TYPE: DNA
<213> ORGANISM: Artificial Sequence
<220> FEATURE:
<223> OTHER INFORMATION: Nucleic acid ancoding heavy chain of SG701

<400> SEQUENCE: 49
caggtgcagc tggtgcagag cggcgccgag gtgaagaagc tggcgccag cgtgaaggtg      60 agctgcaagg ccagcggcta caccttcacc aacaactaca tccactgggt gaggcaggcc     120
cctggccagg gcctggagtg gatgggcatg atcaaccctac gcggcggcag caccacctac    180
gcccagaagt tccagggcag gctgaccatg accagggaca ccagcaccag caccgtgtac    240
atggacctga gcagcctgag gagcgaggac accgccgtgt actactgcgc cagggccgcc    300
ctgagctact acagcatcgt gaccgccaag gactacggca tggacgtgtg gggccagggc    360
accaccgtga ccgtgagcag cgctagcacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagcc caaatcttgt gacaaaactc acacatgccc accgtgccca    720
gcacctgaac tcctggggggg accgtcagtc ttcctcttcc cccaaaaacc caaggacacc    780
ctcatgatct cccggacccc tgaggtcacg tgcgtggtgg tggacgtgag ccacgaagac    840
cccgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gatgcatgag   1320
gctctgcaca accactacac gcagaagagc ctctccctgt ctccgggtaa atga         1374

<210> SEQ ID NO 50
<211> LENGTH: 117
<212> TYPE: PRT
<213> ORGANISM: Artificial Sequence
<220> FEATURE:

<223> OTHER INFORMATION: Truncated domain of human SIRP alpha variant 1

<400> SEQUENCE: 50

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
                20                  25                  30

Pro Ile Gln Trp Phe Arg Gly Ala Gly Pro Gly Arg Glu Leu Ile Tyr
            35                  40                  45

Asn Gln Lys Glu Gly His Phe Pro Arg Val Thr Thr Val Ser Asp Leu
        50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
            115

<210> SEQ ID NO 51
<211> LENGTH: 117
<212> TYPE: PRT
<213> ORGANISM: Artificial Sequence
<220> FEATURE:
<223> OTHER INFORMATION: M1

<400> SEQUENCE: 51

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
                20                  25                  30

Pro Ile Gln Trp Phe Arg Gly Ala Gly Pro Gly Arg Ile Leu Ile Tyr
            35                  40                  45

Asn Gln Lys Lys Gly His Phe Pro Arg Val Thr Thr Leu Ser Asp Ser
        50                  55                  60

Thr Arg Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
            115

<210> SEQ ID NO 52
<211> LENGTH: 117
<212> TYPE: PRT
<213> ORGANISM: Artificial Sequence
<220> FEATURE:
<223> OTHER INFORMATION: M5

<400> SEQUENCE: 52

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
                20                  25                  30

Pro Ile Gln Trp Phe Arg Gly Ala Gly Pro Gly Arg Asn Leu Ile Tyr

```
                35                  40                  45
Asn Ser Arg His Gly His Phe Pro Arg Val Thr Thr Val Ser Asp Leu
         50                  55                  60
Thr Lys Arg Asn Asn Met Asp Phe Ser Ile Arg Ile Gly Asn Ile Thr
 65                  70                  75                  80
Pro Ala Asp Ala Gly Thr Tyr Tyr Cys Val Lys Phe Arg Lys Gly Ser
                 85                  90                  95
Pro Asp Asp Val Glu Phe Lys Ser Gly Ala Gly Thr Glu Leu Ser Val
                100                 105                 110
Arg Ala Lys Pro Ser
            115

<210> SEQ ID NO 53
<211> LENGTH: 117
<212> TYPE: PRT
<213> ORGANISM: Artificial Sequence
<220> FEATURE:
<223> OTHER INFORMATION: M12

<400> SEQUENCE: 53

Glu Leu Gln Val Ile Gln Pro Asp Lys Ser Val Leu Val Ala Ala Gly
 1               5                  10                  15
Glu Thr Ala Thr Leu Arg Cys Thr Ala Thr Ser Leu Phe Pro Ile Gly
                20                  25                  30
Pro Ile Gln Trp Phe Arg Gly Ala Gly Pro Gly Arg Glu Leu Ile Tyr
                35                  40                  45
Asn Gln Arg Lys Gly His Phe Pro Arg Val Thr Thr Val Ser Asp Leu
         50                  55                  60
Thr Lys Arg Asn Asn Met Asp Phe Ser Ile Arg Ile Gly Asn Ile Thr
 65                  70                  75                  80
Pro Ala Asp Ala Gly Thr Tyr Tyr Cys Val Lys Phe Arg Lys Gly Ser
                 85                  90                  95
Pro Asp Asp Ile Glu Phe Lys Ser Gly Ala Gly Thr Glu Leu Ser Val
                100                 105                 110
Arg Ala Lys Pro Ser
            115

<210> SEQ ID NO 54
<211> LENGTH: 117
<212> TYPE: PRT
<213> ORGANISM: Artificial Sequence
<220> FEATURE:
<223> OTHER INFORMATION: M35

<400> SEQUENCE: 54

Glu Leu Gln Val Ile Gln Pro Asp Lys Ser Val Leu Val Ala Ala Gly
 1               5                  10                  15
Glu Thr Ala Thr Leu Arg Cys Thr Ala Thr Ser Leu Leu Pro Val Gly
                20                  25                  30
Pro Ile Gln Trp Phe Arg Gly Ala Gly Pro Gly Arg Gln Leu Ile Tyr
                35                  40                  45
Asn Gln Lys Asp Gly His Phe Pro Arg Val Thr Thr Val Ser Asp Leu
         50                  55                  60
Thr Lys Arg Asn Asn Met Asp Phe Ser Ile Asn Ile Gly Asn Ile Thr
 65                  70                  75                  80
Pro Ala Asp Ala Gly Thr Tyr Tyr Cys Val Lys Phe Arg Lys Gly Ser
                 85                  90                  95
```

Pro Asp Asp Ile Glu Phe Lys Ser Gly Ala Gly Thr Glu Leu Ser Val
            100                 105                 110

Arg Ala Lys Pro Ser
        115

<210> SEQ ID NO 55
<211> LENGTH: 117
<212> TYPE: PRT
<213> ORGANISM: Artificial Sequence
<220> FEATURE:
<223> OTHER INFORMATION: M37

<400> SEQUENCE: 55

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Lys Leu Ile Tyr
        35                  40                  45

Asn Gln Arg Asp Gly His Phe Pro Arg Val Thr Thr Val Ser Asp Leu
    50                  55                  60

Thr Lys Arg Gly Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 56
<211> LENGTH: 117
<212> TYPE: PRT
<213> ORGANISM: Artificial Sequence
<220> FEATURE:
<223> OTHER INFORMATION: M41

<400> SEQUENCE: 56

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

Pro Ile Gln Trp Phe Arg Gly Ala Gly Pro Gly Arg His Leu Ile Tyr
        35                  40                  45

Asn Arg Arg His Gly His Phe Pro Arg Val Thr Thr Val Ser Asp Leu
    50                  55                  60

Thr Lys Arg Asn Asn Met Asp Phe Ser Ile Ser Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
        115

<210> SEQ ID NO 57
<211> LENGTH: 117
<212> TYPE: PRT
<213> ORGANISM: Artificial Sequence -continued

```
<220> FEATURE:
<223> OTHER INFORMATION: M57

<400> SEQUENCE: 57

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30

Pro Ile Gln Trp Phe Arg Gly Ala Gly Pro Gly Arg Ile Leu Ile Tyr
            35                  40                  45

Asn Gly Lys Arg Gly His Phe Pro Arg Val Thr Thr Leu Ser Asp Thr
    50                  55                  60

Thr Lys Arg Gly Asn Met Asp Phe Ser Ile Ser Ile Arg Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Arg Glu Phe Lys Ser Gly Ala Gly Thr Glu Leu Ser Val
            100                 105                 110

Arg Ala Lys Pro Ser
        115

<210> SEQ ID NO 58
<211> LENGTH: 117
<212> TYPE: PRT
<213> ORGANISM: Artificial Sequence
<220> FEATURE:
<223> OTHER INFORMATION: M67

<400> SEQUENCE: 58

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30

Pro Ile Gln Trp Phe Arg Gly Ala Gly Pro Gly Arg Met Leu Ile Tyr
            35                  40                  45

Asn Gly Arg Asp Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
        115

<210> SEQ ID NO 59
<211> LENGTH: 117
<212> TYPE: PRT
<213> ORGANISM: Artificial Sequence
<220> FEATURE:
<223> OTHER INFORMATION: M81

<400> SEQUENCE: 59

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
                20                  25                  30
```

-continued

Pro Ile Gln Trp Phe Arg Gly Ala Gly Pro Gly Arg Glu Leu Ile Tyr
            35                  40                  45

Asn Gln Lys Glu Gly His Phe Pro Arg Val Thr Thr Val Ser Asp Leu
 50                      55                      60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                 85                  90                  95

Pro Asp Asp Val Glu Phe Lys Ser Gly Ala Gly Thr Glu Leu Ser Val
                100                 105                 110

Arg Ala Lys Pro Ser
            115

<210> SEQ ID NO 60
<211> LENGTH: 117
<212> TYPE: PRT
<213> ORGANISM: Artificial Sequence
<220> FEATURE:
<223> OTHER INFORMATION: M82

<400> SEQUENCE: 60

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Phe Pro Val Gly
                20                  25                  30

Pro Ile Gln Trp Phe Arg Gly Ala Gly Pro Gly Arg Glu Leu Ile Tyr
            35                  40                  45

Asn Gln Lys Glu Gly His Phe Pro Arg Val Thr Thr Val Ser His Ser
 50                      55                      60

Thr Lys Arg Asn Asn Met Asp Phe Ser Ile Arg Ile His Asn Ile Thr
 65                  70                  75                  80

Pro Ala Asp Ala Gly Thr Tyr Tyr Cys Val Lys Phe Arg Lys Gly Ser
                 85                  90                  95

Pro Asp Asp Ser Glu Phe Lys Ser Gly Ala Gly Thr Glu Leu Ser Val
                100                 105                 110

Arg Ala Lys Pro Ser
            115

<210> SEQ ID NO 61
<211> LENGTH: 117
<212> TYPE: PRT
<213> ORGANISM: Artificial Sequence
<220> FEATURE:
<223> OTHER INFORMATION: M84

<400> SEQUENCE: 61

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Phe Pro Val Gly
                20                  25                  30

Pro Ile Gln Trp Phe Arg Gly Ala Gly Pro Gly Arg Glu Leu Ile Tyr
            35                  40                  45

Asn Gln Lys Glu Gly His Phe Pro Arg Val Thr Thr Val Ser His Ser
 50                      55                      60

Thr Arg Arg Asn Asn Met Asp Phe Ser Ile Arg Ile His Asn Ile Thr
 65                  70                  75                  80

Pro Ala Asp Ala Gly Thr Tyr Tyr Cys Val Lys Phe Arg Lys Gly Ser
                 85                  90                  95

```
Pro Asp Asp Ser Glu Phe Lys Ser Gly Ala Gly Thr Glu Leu Ser Val
            100                 105                 110

Arg Ala Lys Pro Ser
        115

<210> SEQ ID NO 62
<211> LENGTH: 117
<212> TYPE: PRT
<213> ORGANISM: Artificial Sequence
<220> FEATURE:
<223> OTHER INFORMATION: M91

<400> SEQUENCE: 62

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Gln Leu Ile Tyr
        35                  40                  45

Asn Gln Lys Asp Gly His Phe Pro Arg Val Thr Thr Ala Ser Asp Leu
    50                  55                  60

Thr Lys Arg Asn Asn Met Asp Phe Ser Ile Asn Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115

<210> SEQ ID NO 63
<211> LENGTH: 117
<212> TYPE: PRT
<213> ORGANISM: Artificial Sequence
<220> FEATURE:
<223> OTHER INFORMATION: M99

<400> SEQUENCE: 63

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Lys Leu Ile Tyr
        35                  40                  45

Asn Gln Lys Gly Gly His Phe Pro Arg Val Thr Thr Val Ser Asp Ser
    50                  55                  60

Thr Lys Arg Lys Asn Met Asp Phe Ser Ile Arg Ile His Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
        115

<210> SEQ ID NO 64
<211> LENGTH: 117
<212> TYPE: PRT
```

<213> ORGANISM: Artificial Sequence
<220> FEATURE:
<223> OTHER INFORMATION: M102

<400> SEQUENCE: 64

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Glu Leu Ile Tyr
        35                  40                  45

Asn Gly Lys Gly Gly His Phe Pro Arg Val Thr Thr Val Ser Arg Ser
    50                  55                  60

Thr Lys Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Ile Glu Phe Lys Ser Gly Ala Gly Thr Glu Leu Ser Val
            100                 105                 110

Arg Ala Lys Pro Ser
        115

<210> SEQ ID NO 65
<211> LENGTH: 117
<212> TYPE: PRT
<213> ORGANISM: Artificial Sequence
<220> FEATURE:
<223> OTHER INFORMATION: M111

<400> SEQUENCE: 65

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Leu Pro Val Gly
            20                  25                  30

Pro Ile Gln Trp Phe Arg Gly Ala Gly Pro Gly Arg Arg Leu Ile Tyr
        35                  40                  45

Asn Asn Arg Gly Gly His Phe Pro Arg Val Thr Thr Leu Ser Glu Thr
    50                  55                  60

Thr Arg Arg Asp Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Leu Glu Phe Lys Ser Gly Ala Gly Thr Glu Leu Ser Val
            100                 105                 110

Arg Ala Lys Pro Ser
        115

<210> SEQ ID NO 66
<211> LENGTH: 117
<212> TYPE: PRT
<213> ORGANISM: Artificial Sequence
<220> FEATURE:
<223> OTHER INFORMATION: M122

<400> SEQUENCE: 66

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Val Pro Val Gly
            20                  25                  30

```
Pro Ile Gln Trp Phe Arg Gly Ala Gly Pro Gly Arg Asn Leu Ile Tyr
            35                  40                  45

Asn Ser Arg His Gly His Phe Pro Arg Val Thr Thr Ala Ser Asp Leu
        50                  55                  60

Thr Lys Arg Asn Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
            115

<210> SEQ ID NO 67
<211> LENGTH: 117
<212> TYPE: PRT
<213> ORGANISM: Artificial Sequence
<220> FEATURE:
<223> OTHER INFORMATION: M126

<400> SEQUENCE: 67

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Val Pro Ile Gly
            20                  25                  30

Pro Ile Gln Trp Phe Arg Gly Ala Gly Pro Gly Arg Val Leu Ile Tyr
            35                  40                  45

Asn Gln Arg Asp Gly His Phe Pro Arg Val Thr Thr Val Ser Glu Thr
        50                  55                  60

Thr Arg Arg Glu Asn Met Asp Phe Ser Ile Arg Ile Gly Asn Ile Thr
 65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser
            115

<210> SEQ ID NO 68
<211> LENGTH: 117
<212> TYPE: PRT
<213> ORGANISM: Artificial Sequence
<220> FEATURE:
<223> OTHER INFORMATION: M130

<400> SEQUENCE: 68

Glu Leu Gln Val Ile Gln Pro Asp Lys Ser Val Leu Val Ala Ala Gly
 1               5                  10                  15

Glu Thr Ala Thr Leu Arg Cys Thr Ala Thr Ser Leu Leu Pro Ile Gly
            20                  25                  30

Pro Ile Gln Trp Phe Arg Gly Ala Gly Pro Gly Arg Val Leu Ile Tyr
            35                  40                  45

Asn Gln Arg Glu Gly His Phe Pro Arg Val Thr Thr Val Ser Glu Ser
        50                  55                  60

Thr Arg Arg Asp Asn Met Asp Phe Ser Ile Arg Ile Arg Asn Ile Thr
 65                  70                  75                  80

Pro Ala Asp Ala Gly Thr Tyr Tyr Cys Val Lys Phe Arg Lys Gly Ser
```

```
                85                  90                  95
Pro Asp Asp Val Glu Phe Lys Ser Gly Ala Gly Thr Glu Leu Ser Val
            100                 105                 110
Arg Ala Lys Pro Ser
        115

<210> SEQ ID NO 69
<211> LENGTH: 117
<212> TYPE: PRT
<213> ORGANISM: Artificial Sequence
<220> FEATURE:
<223> OTHER INFORMATION: M135

<400> SEQUENCE: 69

Glu Leu Gln Val Ile Gln Pro Asp Lys Ser Val Leu Val Ala Ala Gly
1               5                   10                  15
Glu Thr Ala Thr Leu Arg Cys Thr Ala Thr Ser Leu Val Pro Val Gly
            20                  25                  30
Pro Ile Gln Trp Phe Arg Gly Ala Gly Pro Gly Arg Leu Leu Ile Tyr
        35                  40                  45
Asn Gly Lys Gly Gly His Phe Pro Arg Val Thr Thr Leu Ser Glu Thr
    50                  55                  60
Thr Arg Arg Gly Asn Met Asp Phe Ser Ile Arg Ile Gly Asn Ile Thr
65                  70                  75                  80
Pro Ala Asp Ala Gly Thr Tyr Tyr Cys Val Lys Phe Arg Lys Gly Ser
                85                  90                  95
Pro Asp Asp Val Glu Phe Lys Ser Gly Ala Gly Thr Glu Leu Ser Val
            100                 105                 110
Arg Ala Lys Pro Ser
        115

<210> SEQ ID NO 70
<211> LENGTH: 117
<212> TYPE: PRT
<213> ORGANISM: Artificial Sequence
<220> FEATURE:
<223> OTHER INFORMATION: M145

<400> SEQUENCE: 70

Glu Leu Gln Val Ile Gln Pro Asp Lys Ser Val Leu Val Ala Ala Gly
1               5                   10                  15
Glu Thr Ala Thr Leu Arg Cys Thr Ala Thr Ser Leu Leu Pro Ile Gly
            20                  25                  30
Pro Ile Gln Trp Phe Arg Gly Ala Gly Pro Gly Arg Asn Leu Ile Tyr
        35                  40                  45
Asn Gly Lys Gly Gly His Phe Pro Arg Val Thr Thr Val Ser Asp Leu
    50                  55                  60
Thr Lys Arg Asn Asn Met Asp Phe Ser Ile Arg Ile Gly Asn Ile Thr
65                  70                  75                  80
Pro Ala Asp Ala Gly Thr Tyr Tyr Cys Val Lys Phe Arg Lys Gly Ser
                85                  90                  95
Pro Asp Asp Val Glu Phe Lys Ser Gly Ala Gly Thr Glu Leu Ser Val
            100                 105                 110
Arg Ala Lys Pro Ser
        115

<210> SEQ ID NO 71
<211> LENGTH: 233
```

```
<212> TYPE: PRT
<213> ORGANISM: Artificial Sequence
<220> FEATURE:
<223> OTHER INFORMATION: IgG1-FC

<400> SEQUENCE: 71
```

| Leu | Glu | Pro | Lys | Ser | Cys | Asp | Lys | Thr | His | Thr | Cys | Pro | Pro | Cys | Pro |
|---|---|---|---|---|---|---|---|---|---|---|---|---|---|---|---|
| 1 | | | | 5 | | | | | 10 | | | | | 15 | |

| Ala | Pro | Glu | Leu | Leu | Gly | Gly | Pro | Ser | Val | Phe | Leu | Phe | Pro | Pro | Lys |
|---|---|---|---|---|---|---|---|---|---|---|---|---|---|---|---|
| | | 20 | | | | | 25 | | | | | 30 | | | |

| Pro | Lys | Asp | Thr | Leu | Met | Ile | Ser | Arg | Thr | Pro | Glu | Val | Thr | Cys | Val |
|---|---|---|---|---|---|---|---|---|---|---|---|---|---|---|---|
| | | | 35 | | | | | 40 | | | | | 45 | | |

| Val | Val | Asp | Val | Ser | His | Glu | Asp | Pro | Glu | Val | Lys | Phe | Asn | Trp | Tyr |
|---|---|---|---|---|---|---|---|---|---|---|---|---|---|---|---|
| | 50 | | | | | 55 | | | | | 60 | | | | |

| Val | Asp | Gly | Val | Glu | Val | His | Asn | Ala | Lys | Thr | Lys | Pro | Arg | Glu | Glu |
|---|---|---|---|---|---|---|---|---|---|---|---|---|---|---|---|
| 65 | | | | | 70 | | | | | 75 | | | | | 80 |

| Gln | Tyr | Asn | Ser | Thr | Tyr | Arg | Val | Val | Ser | Val | Leu | Thr | Val | Leu | His |
|---|---|---|---|---|---|---|---|---|---|---|---|---|---|---|---|
| | | | | 85 | | | | | 90 | | | | | 95 | |

| Gln | Asp | Trp | Leu | Asn | Gly | Lys | Glu | Tyr | Lys | Cys | Lys | Val | Ser | Asn | Lys |
|---|---|---|---|---|---|---|---|---|---|---|---|---|---|---|---|
| | | | 100 | | | | | 105 | | | | | 110 | | |

| Ala | Leu | Pro | Ala | Pro | Ile | Glu | Lys | Thr | Ile | Ser | Lys | Ala | Lys | Gly | Gln |
|---|---|---|---|---|---|---|---|---|---|---|---|---|---|---|---|
| | | 115 | | | | | 120 | | | | | 125 | | | |

| Pro | Arg | Glu | Pro | Gln | Val | Tyr | Thr | Leu | Pro | Pro | Ser | Arg | Asp | Glu | Leu |
|---|---|---|---|---|---|---|---|---|---|---|---|---|---|---|---|
| | 130 | | | | | 135 | | | | | 140 | | | | |

| Thr | Lys | Asn | Gln | Val | Ser | Leu | Thr | Cys | Leu | Val | Lys | Gly | Phe | Tyr | Pro |
|---|---|---|---|---|---|---|---|---|---|---|---|---|---|---|---|
| 145 | | | | | 150 | | | | | 155 | | | | | 160 |

| Ser | Asp | Ile | Ala | Val | Glu | Trp | Glu | Ser | Asn | Gly | Gln | Pro | Glu | Asn | Asn |
|---|---|---|---|---|---|---|---|---|---|---|---|---|---|---|---|
| | | | | 165 | | | | | 170 | | | | | 175 | |

| Tyr | Lys | Thr | Thr | Pro | Pro | Val | Leu | Asp | Ser | Asp | Gly | Ser | Phe | Phe | Leu |
|---|---|---|---|---|---|---|---|---|---|---|---|---|---|---|---|
| | | | 180 | | | | | 185 | | | | | 190 | | |

| Tyr | Ser | Lys | Leu | Thr | Val | Asp | Lys | Ser | Arg | Trp | Gln | Gln | Gly | Asn | Val |
|---|---|---|---|---|---|---|---|---|---|---|---|---|---|---|---|
| | | 195 | | | | | 200 | | | | | 205 | | | |

| Phe | Ser | Cys | Ser | Val | Met | His | Glu | Ala | Leu | His | Asn | His | Tyr | Thr | Gln |
|---|---|---|---|---|---|---|---|---|---|---|---|---|---|---|---|
| | 210 | | | | | 215 | | | | | 220 | | | | |

| Lys | Ser | Leu | Ser | Leu | Ser | Pro | Gly | Lys |
|---|---|---|---|---|---|---|---|---|
| 225 | | | | | 230 | | | |

```
<210> SEQ ID NO 72
<211> LENGTH: 350
<212> TYPE: PRT
<213> ORGANISM: Artificial Sequence
<220> FEATURE:
<223> OTHER INFORMATION: SS002M91

<400> SEQUENCE: 72
```

| Glu | Leu | Gln | Val | Ile | Gln | Pro | Asp | Lys | Ser | Val | Leu | Val | Ala | Ala | Gly |
|---|---|---|---|---|---|---|---|---|---|---|---|---|---|---|---|
| 1 | | | | 5 | | | | | 10 | | | | | 15 | |

| Glu | Thr | Ala | Thr | Leu | Arg | Cys | Thr | Ala | Thr | Ser | Leu | Leu | Pro | Val | Gly |
|---|---|---|---|---|---|---|---|---|---|---|---|---|---|---|---|
| | | | 20 | | | | | 25 | | | | | 30 | | |

| Pro | Ile | Gln | Trp | Phe | Arg | Gly | Ala | Gly | Pro | Gly | Arg | Gln | Leu | Ile | Tyr |
|---|---|---|---|---|---|---|---|---|---|---|---|---|---|---|---|
| | | | 35 | | | | | 40 | | | | | 45 | | |

| Asn | Gln | Lys | Asp | Gly | His | Phe | Pro | Arg | Val | Thr | Thr | Ala | Ser | Asp | Leu |
|---|---|---|---|---|---|---|---|---|---|---|---|---|---|---|---|
| | 50 | | | | | 55 | | | | | 60 | | | | |

| Thr | Lys | Arg | Asn | Asn | Met | Asp | Phe | Ser | Ile | Asn | Ile | Gly | Asn | Ile | Thr |
|---|---|---|---|---|---|---|---|---|---|---|---|---|---|---|---|
| 65 | | | | | 70 | | | | | 75 | | | | | 80 |

| Pro | Ala | Asp | Ala | Gly | Thr | Tyr | Tyr | Cys | Val | Lys | Phe | Arg | Lys | Gly | Ser |
|---|---|---|---|---|---|---|---|---|---|---|---|---|---|---|---|
| | | | | 85 | | | | | 90 | | | | | 95 | |

```
Pro Asp Asp Ile Glu Phe Lys Ser Gly Ala Gly Thr Glu Leu Ser Val
            100                 105                 110
Arg Ala Lys Pro Ser Leu Glu Pro Lys Ser Cys Asp Lys Thr His Thr
            115                 120                 125
Cys Pro Pro Cys Pro Ala Pro Glu Leu Leu Gly Gly Pro Ser Val Phe
130                 135                 140
Leu Phe Pro Pro Lys Pro Lys Asp Thr Leu Met Ile Ser Arg Thr Pro
145                 150                 155                 160
Glu Val Thr Cys Val Val Val Asp Val Ser His Glu Asp Pro Glu Val
                165                 170                 175
Lys Phe Asn Trp Tyr Val Asp Gly Val Glu Val His Asn Ala Lys Thr
            180                 185                 190
Lys Pro Arg Glu Glu Gln Tyr Asn Ser Thr Tyr Arg Val Val Ser Val
            195                 200                 205
Leu Thr Val Leu His Gln Asp Trp Leu Asn Gly Lys Glu Tyr Lys Cys
210                 215                 220
Lys Val Ser Asn Lys Ala Leu Pro Ala Pro Ile Glu Lys Thr Ile Ser
225                 230                 235                 240
Lys Ala Lys Gly Gln Pro Arg Glu Pro Gln Val Tyr Thr Leu Pro Pro
                245                 250                 255
Ser Arg Asp Glu Leu Thr Lys Asn Gln Val Ser Leu Thr Cys Leu Val
            260                 265                 270
Lys Gly Phe Tyr Pro Ser Asp Ile Ala Val Glu Trp Glu Ser Asn Gly
            275                 280                 285
Gln Pro Glu Asn Asn Tyr Lys Thr Thr Pro Pro Val Leu Asp Ser Asp
290                 295                 300
Gly Ser Phe Phe Leu Tyr Ser Lys Leu Thr Val Asp Lys Ser Arg Trp
305                 310                 315                 320
Gln Gln Gly Asn Val Phe Ser Cys Ser Val Met His Glu Ala Leu His
                325                 330                 335
Asn His Tyr Thr Gln Lys Ser Leu Ser Leu Ser Pro Gly Lys
            340                 345                 350

<210> SEQ ID NO 73
<211> LENGTH: 10
<212> TYPE: PRT
<213> ORGANISM: Artificial Sequence
<220> FEATURE:
<223> OTHER INFORMATION: Linker 1

<400> SEQUENCE: 73

Gly Gly Gly Gly Ser Gly Gly Gly Gly Ser
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Linker 2

<400> SEQUENCE: 74

Gly Gly Gly Ser Ala Ala Ala
1               5

<210> SEQ ID NO 75
<211> LENGTH: 576
<212> TYPE: PRT
```

<213> ORGANISM: Artificial Sequence
<220> FEATURE:
<223> OTHER INFORMATION: The second polypeptide chain of SG3847L1

<400> SEQUENCE: 75

```
Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
            20                  25                  30

Trp Met Asn Trp Val Arg Gln Ala Pro Gly Lys Gly Leu Glu Trp Ile
        35                  40                  45

Gly Lys Ile Asn Pro Asp Ser Ser Thr Ile Asn Tyr Thr Pro Ser Leu
    50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Phe Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

```
                385                 390                 395                 400
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys Gly Gly Gly Ser Gly Gly Gly Ser Glu Leu Gln Val Ile
450                 455                 460

Gln Pro Asp Lys Ser Val Leu Ala Ala Gly Glu Thr Ala Thr Leu
465                 470                 475                 480

Arg Cys Thr Ala Thr Ser Leu Leu Pro Val Gly Pro Ile Gln Trp Phe
                485                 490                 495

Arg Gly Ala Gly Pro Gly Arg Gln Leu Ile Tyr Asn Gln Lys Asp Gly
                500                 505                 510

His Phe Pro Arg Val Thr Thr Ala Ser Asp Leu Thr Lys Arg Asn Asn
                515                 520                 525

Met Asp Phe Ser Ile Asn Ile Gly Asn Ile Thr Pro Ala Asp Ala Gly
                530                 535                 540

Thr Tyr Tyr Cys Val Lys Phe Arg Lys Gly Ser Pro Asp Asp Ile Glu
545                 550                 555                 560

Phe Lys Ser Gly Ala Gly Thr Glu Leu Ser Val Arg Ala Lys Pro Ser
                565                 570                 575

<210> SEQ ID NO 76
<211> LENGTH: 573
<212> TYPE: PRT
<213> ORGANISM: Artificial Sequence
<220> FEATURE:
<223> OTHER INFORMATION: The second polypeptide chain of SG3847L2

<400> SEQUENCE: 76

Gln Val Gln Leu Leu Glu Ser Gly Gly Gly Leu Val Gln Pro Gly Gly
1               5                   10                  15

Ser Leu Lys Leu Ser Cys Val Ala Ser Gly Phe Asp Phe Ser Leu Tyr
                20                  25                  30

Trp Met Asn Trp Val Arg Gln Ala Pro Gly Lys Gly Leu Glu Trp Ile
                35                  40                  45

Gly Lys Ile Asn Pro Asp Ser Ser Thr Ile Asn Tyr Thr Pro Ser Leu
                50                  55                  60

Lys Asp Lys Phe Phe Ile Ser Arg Asp Asn Ala Lys Asn Thr Leu Tyr
65                  70                  75                  80

Leu Gln Met Thr Lys Val Arg Ser Glu Asp Thr Ala Leu Tyr Tyr Cys
                85                  90                  95

Ala Arg Leu Trp Ile Ala Thr Gly Gly Phe Asp Tyr Trp Gly Gln Gly
                100                 105                 110

Thr Thr Leu Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180             185             190
Ser Ser Leu Gly Thr Gln Thr Tyr Ile Cys Asn Val Asn His Lys Pro
        195             200             205
Ser Asn Thr Lys Val Asp Lys Val Glu Pro Lys Ser Cys Asp Lys
    210             215             220
Thr His Thr Cys Pro Pro Cys Pro Ala Pro Glu Leu Leu Gly Gly Pro
225             230             235             240
Ser Val Phe Leu Phe Pro Pro Lys Pro Lys Asp Thr Leu Met Ile Ser
            245             250             255
Arg Thr Pro Glu Val Thr Cys Val Val Val Asp Val Ser His Glu Asp
        260             265             270
Pro Glu Val Lys Phe Asn Trp Tyr Val Asp Gly Val Glu Val His Asn
    275             280             285
Ala Lys Thr Lys Pro Arg Glu Glu Gln Tyr Asn Ser Thr Tyr Arg Val
290             295             300
Val Ser Val Leu Thr Val Leu His Gln Asp Trp Leu Asn Gly Lys Glu
305             310             315             320
Tyr Lys Cys Lys Val Ser Asn Lys Ala Leu Pro Ala Pro Ile Glu Lys
            325             330             335
Thr Ile Ser Lys Ala Lys Gly Gln Pro Arg Glu Pro Gln Val Tyr Thr
        340             345             350
Leu Pro Pro Ser Arg Asp Glu Leu Thr Lys Asn Gln Val Ser Leu Thr
    355             360             365
Cys Leu Val Lys Gly Phe Tyr Pro Ser Asp Ile Ala Val Glu Trp Glu
370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
            405             410             415
Ser Arg Trp Gln Gln Gly Asn Val Phe Ser Cys Ser Val Met His Glu
        420             425             430
Ala Leu His Asn His Tyr Thr Gln Lys Ser Leu Ser Leu Ser Pro Gly
    435             440             445
Lys Gly Gly Gly Ser Ala Ala Ala Glu Leu Gln Val Ile Gln Pro Asp
450             455             460
Lys Ser Val Leu Val Ala Ala Gly Glu Thr Ala Thr Leu Arg Cys Thr
465             470             475             480
Ala Thr Ser Leu Leu Pro Val Gly Pro Ile Gln Trp Phe Arg Gly Ala
            485             490             495
Gly Pro Gly Arg Gln Leu Ile Tyr Asn Gln Lys Asp Gly His Phe Pro
        500             505             510
Arg Val Thr Thr Ala Ser Asp Leu Thr Lys Arg Asn Asn Met Asp Phe
    515             520             525
Ser Ile Asn Ile Gly Asn Ile Thr Pro Ala Asp Ala Gly Thr Tyr Tyr
530             535             540
Cys Val Lys Phe Arg Lys Gly Ser Pro Asp Asp Ile Glu Phe Lys Ser
545             550             555             560
Gly Ala Gly Thr Glu Leu Ser Val Arg Ala Lys Pro Ser
            565             570
```

<210> SEQ ID NO 77
<211> LENGTH: 573
<212> TYPE: PRT
<213> ORGANISM: Artificial Sequence
<220> FEATURE:
<223> OTHER INFORMATION: The second polypeptide chain of SGAXL47

<400> SEQUENCE: 77

```
Gln Val Gln Leu Lys Gln Ser Gly Pro Gly Leu Val Lys Pro Ser Gln
1               5                   10                  15

Ser Leu Ser Leu Thr Cys Ser Val Thr Gly Phe Ser Ile Ser Ser Gly
            20                  25                  30

Tyr Tyr Trp Asn Trp Ile Arg Gln Phe Pro Gly Asn Lys Leu Glu Trp
        35                  40                  45

Met Gly Tyr Arg Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Trp Leu Leu His Tyr Thr Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Ser Ala Ala Ala Glu Leu Gln Val Ile Gln Pro Asp
    450                 455                 460

Lys Ser Val Leu Val Ala Ala Gly Glu Thr Ala Thr Leu Arg Cys Thr
465                 470                 475                 480

Ala Thr Ser Leu Leu Pro Val Gly Pro Ile Gln Trp Phe Arg Gly Ala
                485                 490                 495

Gly Pro Gly Arg Gln Leu Ile Tyr Asn Gln Lys Asp Gly His Phe Pro
            500                 505                 510

Arg Val Thr Thr Ala Ser Asp Leu Thr Lys Arg Asn Asn Met Asp Phe
        515                 520                 525

Ser Ile Asn Ile Gly Asn Ile Thr Pro Ala Asp Ala Gly Thr Tyr Tyr
    530                 535                 540

Cys Val Lys Phe Arg Lys Gly Ser Pro Asp Asp Ile Glu Phe Lys Ser
545                 550                 555                 560

Gly Ala Gly Thr Glu Leu Ser Val Arg Ala Lys Pro Ser
                565                 570

<210> SEQ ID NO 78
<211> LENGTH: 581
<212> TYPE: PRT
<213> ORGANISM: Artificial Sequence
<220> FEATURE:
<223> OTHER INFORMATION: The second polypeptide chain of SGTrop247

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Tyr Ile His Trp Val Arg Gln Ala Pro Gly Gln Gly Leu Glu Trp Met
        35                  40                  45

Gly Met Ile Asn Pro Ser Gly Gly Ser Thr Thr Tyr Ala Gln Lys Phe
    50                  55                  60

Gln Gly Arg Leu Thr Met Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Ala Ala Leu Ser Tyr Tyr Ser Ile Val Thr Ala Lys Asp Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190
```

```
Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys Gly Gly Gly Ser Ala Ala Ala
    450                 455                 460

Glu Leu Gln Val Ile Gln Pro Asp Lys Ser Val Leu Val Ala Ala Gly
465                 470                 475                 480

Glu Thr Ala Thr Leu Arg Cys Thr Ala Thr Ser Leu Leu Pro Val Gly
                485                 490                 495

Pro Ile Gln Trp Phe Arg Gly Ala Gly Pro Gly Arg Gln Leu Ile Tyr
            500                 505                 510

Asn Gln Lys Asp Gly His Phe Pro Arg Val Thr Thr Ala Ser Asp Leu
        515                 520                 525

Thr Lys Arg Asn Asn Met Asp Phe Ser Ile Asn Ile Gly Asn Ile Thr
    530                 535                 540

Pro Ala Asp Ala Gly Thr Tyr Tyr Cys Val Lys Phe Arg Lys Gly Ser
545                 550                 555                 560

Pro Asp Asp Ile Glu Phe Lys Ser Gly Ala Gly Thr Glu Leu Ser Val
                565                 570                 575

Arg Ala Lys Pro Ser
            580
```

FUSION PROTEIN AND USE THEREOF

FIELD OF THE INVENTION

The present application relates to the field of biomedicine, and particularly to a multi specific fusion protein, and further to a use thereof in the treatment of a tumor and/or an autoimmune disease.

BACKGROUND OF THE INVENTION

At present, in the field of tumor therapy, there are two major methods of administering targeted drugs and immunotherapy. There may be an interaction between these two therapies, causing a stronger cytotoxic effect, thus alleviating the tumors steadily and sustainably. However, the interaction between targeted drugs and immunotherapy is very complicated, and the overall antitumor effect and the toxicity profile of the combined therapy may be affected by various factors such as species, dosages, order, dosage forms and the like.

CD47 protein is a kind of transmembrane glycoprotein, which is a member belonging to the immunoglobulin superfamily. In addition to being expressed by normal tissue cells, CD47 is over-expressed by many tumor cells. CD47 on the surface of tumors cells binds with SIRPα on the surface of macrophages, which prevents the phagocytosis of tumors cells by macrophages, this is considered as one mechanism by which tumors evade from surveillance of immune system. Blocking the interaction between CD47 protein and SIRPα can inhibit the tumor growth.

However, the current reagents used to block the interaction between CD47 protein and SIRPα have limited recognition activity, their affinities with CD47 protein are always insufficient, so they have limited capacity on inhibiting the tumors. In addition, the current antibody drugs targeting CD47 may cause side effects such as anemia reactions or thrombocytopenia. Therefore, it is urgent to obtain an effective therapy which specifically target both CD47 protein and associated tumor antigens.

SUMMARY OF THE INVENTION

The present application provides a fusion protein, including a first binding domain that specifically binds a tumor-associated antigen and a second binding domain that specifically binds a CD47 protein. The present application also provides an immunoconjugate including the fusion protein; a nucleic acid molecule encoding the fusion protein; a vector, a composition and a cell capable of including and/or expressing the fusion protein; and a method for preparing the fusion protein. The fusion protein, the immunoconjugate, the nucleic acid molecule, the vector, the composition and the cell of the present application have one or more of the following properties: 1) capable of specifically binding both CD47 protein and the tumor-associated antigen; 2) capable of specifically blocking the interaction between CD47 protein and SIRPα; 3) capable of effectively inhibiting the growth and/or proliferation of tumors or tumor cells.

In one aspect, the present application provides a fusion protein, including: a first binding domain that specifically binds a tumor-associated antigen; and a second binding domain that specifically binds a CD47 protein; wherein the second binding domain comprises a mutant of a human SIRPα variant 1, the mutant comprises substitution, deletion or additions of an amino acid residue at one or more positions from site 33 to site 149 compared to the sequence as shown in SEQ ID NO: 50.

In some embodiments, the mutant comprises amino acid substitutions at one or more amino acid residues selected from the group consisting of: R22, I29, I61, V63, E77, Q82, K83, E84, V93, D95, D96, K98, N100, R107, G109 and V132.

In some embodiments, the mutant comprises amino acid substitutions at amino acid residues selected from the group consisting of: (1) I61, V63, E77, E84, V93, L96, K98, N100 and V132; (2) I61, E77, Q82, K83 and E84; (3) I61, V63, K83, E84 and V132; (4) I61, E77, E84, R107 and V132; (5) I61, V63, E77, K83, E84 and N100; (6) I61, E77, Q82, K83, E84 and R107; (7) I61, E77, Q82, E84, V93, L96, N100, R107, G109 and V132; (8) I61, E77, Q82, K83, E84 and V132; (9) I61; (10) I61, D95, L96, G109 and V132; (11) I61, D95, L96, K98, G109 and V132; (12) I61, E77, E84, V93, R107 and V132; (13) E77, L96, N100, G109 and V132; (14) I61, V63, Q82, E84, D95, L96, N100 and V132; (15) I61, E77, Q82, K83, E84, V93, D95, L96, K98, N100 and V132; (16) I61, E77, Q82, K83, E84 and V93; (17) I61, V63, E77, K83, E84, D95, L96, K98 and N100; (18) I61, V63, E77, K83, D95, L96, K98, N100 and G109; (19) I61, E77, Q82, E84, V93, D95, L96, K98 and N100; and (20) I61, V63, E77, Q82 and E84.

In some embodiments, the mutant comprises one or more amino acid substitutions selected from the group consisting of: R22C, I29L, I61L/V/F, V63I, E77I/N/Q/K/H/M/R/N/V/L, Q82S/R/G/N, K83R, E84K/H/D/R/G, V93L/A, D95H/R/E, D96S/T, K98R, N100G/K/D/E, R107N/S, G109R/H and V132L/R/I/S.

In some embodiments, the mutant comprises amino acid substitutions selected from the group consisting of: (1) I61L, V63I, E77I, E84K, V93L, L96S, K98R, N100G and V132L; (2) I61V, E77N, Q82S, K83R and E84H; (3) I61F, V63I, K83R, E84K and V132I; (4) I61L, E77Q, E84D, R107N and V132I; (5) I61L, V63I, E77K, K83D and N100G; (6) I61V, E77H, Q82R, K83R, E84H and R107S; (7) I61L, E77I, Q82G, E84R, V93L, L96T, N100G, R107S, G109R and V132R; (8) I61L, E77M, Q82G, K83R, E84D and V132L; (9) I61L; (10) I61F, D95H, L96S, G109H and V132S; (11) I61F, D95H, L96S, K98R, G109H and V132S; (12) I61L, E77Q, E84D, V93A, R107N and V132I; (13) E77K, L96S, N100K, G109H and V132L; (14) I61L, V63I, Q82G, E84G, D95R, L96S, N100D and V132I; (15) I61L, E77R, Q82N, K83R, E84G, V93L, D95E, L96T, K98R, N100D and V132L; (16) I61V, E77N, Q82S, K83R, E84H and V93A; (17) I61V, V63I, E77V, K83R, E84D, D95E, L96T, K98R and N100E; (18) I61L, V63I, E77V, K83R, D95E, L96S, K98R, N100D and G109R; (19) I61V, E77L, Q82G, E84G, V93L, D95E, L96T, K98R and N100G; and (20) I61L, V63I, E77N, Q82G and E84G.

In some embodiments, the mutant comprises an amino acid sequence as shown in any one of SEQ ID NOs: 51-70.

In some embodiments, the first binding domain comprises an antibody or an antigen-binding fragment or a variant thereof. In some embodiments, the antibody is selected from the group consisting of: a monoclonal antibody, a single-chain antibody, a chimeric antibody, a humanized antibody and a fully human antibody. In some embodiments, the antigen-binding fragment is selected from the group consisting of: Fab, Fab', F(ab')2, F(ab)2, dAb, an isolated complementary determining regions CDR, Fv and scFv.

In some embodiments, the variant of the antibody or the antigen-binding fragment thereof is selected from the group consisting of:

a) a protein or polypeptide with substitution, deletion or addition of one or more amino acids in the antibody or the antigen-binding fragment thereof; and b) a protein or polypeptide with a sequence homology of at least 90% with the antibody or the antigen-binding fragment thereof.

In some embodiments, the tumor-associated antigen comprises a tumor-associated antigen associated with a non-solid tumor and/or a solid tumor. In some embodiments, the tumor-associated antigen is selected from the group consisting of: CD38, AXL and Trop2.

In some embodiments, the first binding domain comprises a CD38 antibody or an antigen-binding fragment or a variant thereof. In some embodiments, the CD38 is a human CD38.

In some embodiments, the antibody comprises a heavy chain of the antibody or a fragment thereof, the heavy chain of the antibody or the fragment thereof comprises HCDR1-3, the amino acid sequences of the HCDR1-3 are SEQ ID NO: 4, SEQ ID NO: 5 and SEQ ID NO: 6, successively. In some embodiments, the heavy chain of the antibody or the fragment thereof comprises a heavy chain variable region VH, and the heavy chain variable region VH comprises an amino acid sequence selected from the group consisting of: SEQ ID NO: 8. In some embodiments, the heavy chain of the antibody or the fragment thereof comprises a heavy chain constant region, and the heavy chain constant region comprises IgG. In some embodiments, the IgG is selected from the group consisting of: IgG1 and IgG4. In some embodiments, the heavy chain of the antibody comprises any one of the amino acid sequences selected from those as shown in the group consisting of: SEQ ID NO: 13, SEQ ID NO: 17, SEQ ID NO: 19 and SEQ ID NO: 21.

In some embodiments, the antibody comprises a light chain of the antibody or a fragment thereof, the light chain of the antibody or the fragment thereof comprises LCDR1-3, the amino acid sequences of the LCDR1-3 are SEQ ID NO: 1, SEQ ID NO: 2 and SEQ ID NO: 3, successively. In some embodiments, the light chain of the antibody or the fragment thereof comprises a light chain variable region VL, and the light chain variable region VL comprises an amino acid sequence selected from the group consisting of: SEQ ID NO: 7. In some embodiments, the light chain of the antibody or the fragment thereof comprises a light chain constant region, and the light chain constant region comprises Igκ. In some embodiments, the light chain of the antibody comprises any one of the amino acid sequences selected from those as shown in the group consisting of: SEQ ID NO: 11, SEQ ID NO: 16, SEQ ID NO: 18 and SEQ ID NO: 20.

In some embodiments, the first binding domain comprises an AXL antibody or an antigen-binding fragment or a variant thereof. In some embodiments, the AXL is a human AXL.

In some embodiments, the antibody comprises a heavy chain of the antibody or a fragment thereof, the heavy chain of the antibody or the fragment thereof comprises HCDR1-3, the amino acid sequences of the HCDR1-3 are SEQ ID NO: 25, SEQ ID NO: 26 and SEQ ID NO: 27, successively. In some embodiments, the heavy chain of the antibody or the fragment thereof comprises a heavy chain variable region VH, and the heavy chain variable region VH comprises an amino acid sequence selected from the group consisting of: SEQ ID NO: 29. In some embodiments, the heavy chain of the antibody or the fragment thereof comprises a heavy chain constant region, and the heavy chain constant region comprises IgG. In some embodiments, the IgG is selected from the group consisting of: IgG1 and IgG4. In some embodiments, the heavy chain of the antibody comprises an amino acid sequence selected from the group consisting of: SEQ ID NO: 34.

In some embodiments, the antibody comprises a light chain of the antibody or a fragment thereof, the light chain of the antibody or the fragment thereof comprises LCDR1-3, the amino acid sequences of the LCDR1-3 are SEQ ID NO: 22, SEQ ID NO: 23 and SEQ ID NO: 24, successively. In some embodiments, the light chain of the antibody or the fragment thereof comprises a light chain variable region VL, and the light chain variable region VL comprises an amino acid sequence selected from the group consisting of: SEQ ID NO: 28. In some embodiments, the light chain of the antibody or the fragment thereof comprises a light chain constant region, and the light chain constant region comprises Igκ. In some embodiments, the light chain of the antibody comprises an amino acid sequence selected from the group consisting of: SEQ ID NO: 32.

In some embodiments, the first binding domain comprises a Trop2 antibody or an antigen-binding fragment or a variant thereof. In some embodiments, the Trop2 is a human Trop2.

In some embodiments, the antibody comprises a heavy chain of the antibody or a fragment thereof, the heavy chain of the antibody or the fragment thereof comprises HCDR1-3, the amino acid sequences of the HCDR1-3 are SEQ ID NO: 39, SEQ ID NO: 40 and SEQ ID NO: 41, successively. In some embodiments, the heavy chain of the antibody or the fragment thereof comprises a heavy chain variable region VH, and the heavy chain variable region VH comprises an amino acid sequence selected from the group consisting of: SEQ ID NO: 43. In some embodiments, the heavy chain of the antibody or the fragment thereof comprises a heavy chain constant region, and the heavy chain constant region comprises IgG. In some embodiments, the IgG is selected from the group consisting of: IgG1 and IgG4. In some embodiments, the heavy chain of the antibody comprises an amino acid sequence selected from the group consisting of: SEQ ID NO: 48. In some embodiments, the antibody comprises a light chain of the antibody or a fragment thereof, the light chain of the antibody or the fragment thereof comprises LCDR1-3, the amino acid sequences of the LCDR1-3 are SEQ ID NO: 36, SEQ ID NO: 37 and SEQ ID NO: 38, successively. In some embodiments, the light chain of the antibody or the fragment thereof comprises a light chain variable region VL, and the light chain variable region VL comprises an amino acid sequence selected from the group consisting of: SEQ ID NO: 42. In some embodiments, the light chain of the antibody or the fragment thereof comprises a light chain constant region, and the light chain constant region comprises Igκ. In some embodiments, the light chain of the antibody comprises an amino acid sequence selected from the group consisting of: SEQ ID NO: 46.

In some embodiments, the first binding domain is located at N-terminal of the second binding domain. In some embodiments, the fusion protein further comprises a linker, the linker is located at C-terminal of the first binding domain and located at N-terminal of the second binding domain. In some embodiments, the linker comprises an amino acid sequence as shown in any one of SEQ ID NOs: 73-74.

In some embodiments, the fusion protein comprises at least two of the second binding domains. In some embodiments, each of the second binding domains is located at C-terminal of the first binding domain respectively.

In another aspect, the present application provides an immunoconjugate, which comprises the fusion protein.

In another aspect, the present application provides one or more isolated nucleic acid molecules, which encode the fusion protein or the immunoconjugate.

In another aspect, the present application provides one or more vectors, which comprises the nucleic acid molecules.

In another aspect, the present application provides a composition, which comprises the fusion protein, the immunoconjugate, or the nucleic acid molecules, and optionally, pharmaceutically acceptable excipients.

In another aspect, the present application provides a cell, which comprises the fusion protein, the immunoconjugate, the nucleic acid molecules, or the vectors.

In another aspect, the present application provides a method for preparing the fusion protein, which comprises culturing the cell under a condition enabling the expression of the fusion protein.

In another aspect, the present application provides a use of the fusion protein, the immunoconjugate, the nucleic acid molecules, the vectors, the composition, or the cell in the preparation of a medicament, wherein the medicament is used for treating a tumor or an autoimmune disease.

In some embodiments, the tumor comprises a non-solid tumor and a solid tumor.

In some embodiments, the tumor comprises multiple myeloma, leukemia, Non-Hodgkin lymphoma, Hodgkin's lymphoma, neuroglioma, germinoma, sarcoma, mesothelioma, placentoma, cerebral cancer, bone cancer, skin cancer, nasopharynx cancer, lung cancer, oral cancer, esophagus cancer, gastric cancer, liver cancer, pancreatic cancer, prostate cancer, intestinal cancer, breast cancer, cervical cancer, ovarian cancer and testicular cancer.

In some embodiments, the autoimmune disease comprises chronic lymphocytic thyroiditis, hyperthyroidism, insulin-dependent diabetes mellitus, myasthenia gravis, chronic ulcerative colitis, pernicious anemia with chronic atrophic gastritis, goodpasture syndrome, pemphigus vulgaris, pemphigoid, primary biliary cirrhosis, multiple sclerosis, acute idiopathic polyneuritis, systemic lupus erythematosus, rheumatoid arthritis, scleroderma and polyarteritis nodosa.

In another aspect, the present application provides the fusion protein, the immunoconjugate, the nucleic acid molecules, the vectors, the composition, or the cell, which are used for treating tumors or autoimmune diseases.

In another aspect, the present application provides a method for blocking the interaction between CD47 protein and SIRPα, including administering to a subject in need thereof an effective amount of the fusion protein, the immunoconjugate, the nucleic acid molecules, the vectors, the composition, or the cell.

In another aspect, the present application provides a method for inhibiting the growth and/or proliferation of tumors or tumor cells, including administering to a subject in need thereof an effective amount of the fusion protein, the immunoconjugate, the nucleic acid molecules, the vectors, the composition, or the cell.

Other aspects and advantages of the present application can be conceived easily by those skilled in the art from the following detailed description. The following detailed description only shows and describes exemplary embodiments of the present application. As will be recognized by those skilled in the art, the content of the present application enables those skilled in the art to make changes to the disclosed specific embodiments without departing from the spirit and scope of the invention to which the present application is related. Correspondingly, the attached drawings of the present application and the description of the specification are only exemplary, but not restrictive.

BRIEF DESCRIPTION OF THE DRAWINGS

The specific features related to the present application are shown in the accompanying claims. The characteristics and advantages related to the present application will be better understood with reference to the exemplary embodiments and the attached drawings described in detail below. The attached drawings are illustrated briefly as below:

DETAILED DESCRIPTION OF THE INVENTION

Figure 1:
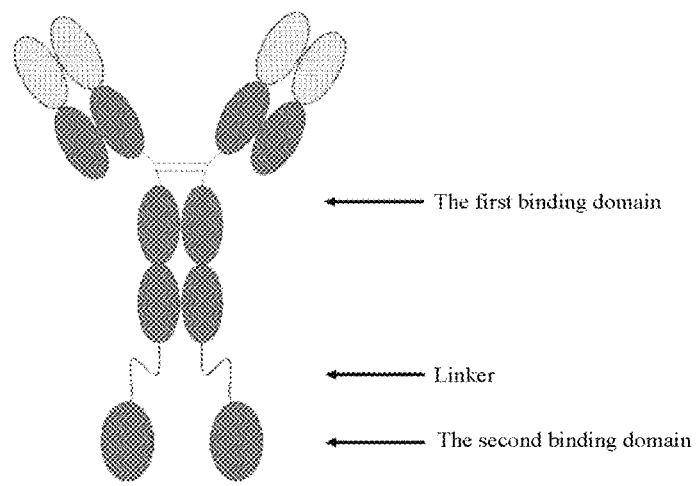
FIG. 1 shows an exemplary structure of the fusion protein according to the present application.

The implementation of the present application will be illustrated in the following specific embodiments, and other advantages and effects of the present application will be easily known by persons familiar with the technology from the disclosures in the specification.

In the present application, the term "fusion protein" generally refers to a protein obtained from the fusion of two or more proteins or polypeptides. The fusion protein can be prepared artificially through a recombinant DNA technology. For example, the genes or nucleic acid molecules encoding the two or more proteins or polypeptides can be linked with each other to form fusion genes or fused nucleic acid molecules, which can encode the fusion protein. The translation of the fusion genes can produce single polypeptide, which can possess the properties of at least one, or even each of the two or more proteins or polypeptides before fusion.

In the present invention, the term "specifically binds" generally refers to the non-random binding reaction between two molecules, such as the reaction between an antibody and an antigen producing the antibody. One antibody specific to a certain antigen means binding to the antigen with an affinity (KD)≤$10^{-5}$ M (e.g., $10^{-6}$ M, $10^{-7}$ M, $10^{-8}$ M, $10^{-9}$ M, $10^{-10}$ M, etc.), wherein KD refers to the ratio of dissociation rate to binding rate ($k_{off}/k_{on}$), which can be determined by a method familiar to technicians in the field.

In the present application, the term "binding domain" generally means a domain that can specifically bind and/or recognize a specific epitope on a target (e.g., an antigen). In the present application, the term "domain" generally refers to a closely spherical structural region that is clearly separated in the subunit structure of a protein. For example, a polypeptide chain firstly can be a regular secondary structure formed from adjacent amino acid residues in some regions, then can also be a super-secondary structure formed by assembling adjacent secondary structural fragments together, on such a basis, the polypeptide chain can be folded into a tertiary structure that is almost spherical. For larger protein molecules or subunits, the polypeptide chain often may be a tertiary structure that is formed by the association of two or more relatively independent regional structures which can be clearly distinguished in space, and such a relatively independent regional structure can be referred as a domain.

In the present application, "the first", "the second" as used in the terms "the first binding domain" and "the second binding domain" are only used for distinction in description.

In the present application, the term "CD47 protein" generally refers to an integrin-associated protein (TAP), which is a multiple transmembrane receptor belonging to the immunoglobulin superfamily. For example, CD47 protein can bind to membrane integrins, and also bind to their ligands thrombospondin-1 (TSP-1) and signal-regulatory protein alpha (SIRPα). CD47 protein is widely expressed on the surface of cell membrane. In the present application, CD47 protein may comprise any variants, isotypes and species homologues of a human CD47. The amino acid sequence of the human CD47 protein is listed as CEJ95640.1 in the GenBank. CD47 protein can be expressed naturally by cells or expressed on cells tranfected with CD47 genes.

In the present application, the term "SIRPα" generally refers to a regulatory membrane glycoprotein from the SIRP family, which can be used as the ligand of CD47 protein. In the present application, the SIRPα may comprise human SIRPα, for example, SIRPα variant 1 and SIRPα variant 2. The SIRPα variant 2 is different from the SIRPα variant 1 in 13 amino acids, and its amino acid sequence is listed as CAA71403.1 in GenBank. In the present application, the term "SIRPα variant 1" generally refers to a SIRPα protein of which the amino acid sequence is listed as NCBI RefSeq NP_542970.1 (residues 31-504 constitute a mature type), then the amino acid sequence of the SIRPα variant 1 is shown in SEQ ID NO: 50.

In the present application, the term "variant" generally refers to a proteinous molecule that has sequence homology with a protein without any mutations/modifications, which retains at least a part of therapeutic and/or biological activity of the bioactive protein. For example, the variant protein can share at least 60%, 65%, 70%, 75%, 80%, 85%, 90%, 95%, 96%, 97%, 98% or 99% of amino acid sequence identity compared to the reference bioactive protein. In some embodiments, "the variant" may comprise proteins which have been intentionally modified (e.g., through site-directed mutagenesis, the synthesis, insertion or occasionally mutation of encoding genes).

The term "antibody" generally refers to a protein including one or more polypeptides essentially encoded by immunoglobulin genes or immunoglobulin gene fragments. For example, immunoglobulin genes may comprise κ, λ, α, γ, δ, ε and μ constant region genes, as well as numerous variable region genes of immunoglobulin. For example, the light chain can be classified into κ or λ, which can define the types of immunoglobulin respectively: Igκ and Igλ. The heavy chain can be classified into γ, α, δ or ε, which, in turn, define the types of immunoglobulin respectively: IgG, IgM, IgA, IgD and IgE. For example, the antibody may have structural units including tetramers, each of the tetramers can be composed of two pairs of the same polypeptide chains, and each pair has a "light chain" (about 25 kD) and a "heavy chain" (about 50-70 kD), the N-terminal of each member can define a variable region of about 100 to 110 or more amino acids, which is mainly responsible for the recognization of antigens. For example, the terms "light chain variable region (VL)" and "heavy chain variable region (VH)" generally refer to the variable region of a light chain and a heavy chain respectively. The antibody may exist as a complete immunoglobulin or as many fully characterized fragments produced by digestion with various peptidases or de novo expression.

In the present invention, the term "antigen-binding fragment" generally refers to one or more parts of a full-length antibody, in which the parts substantially maintain the capacity of binding the same antigen (e.g., CD38) that the antibody binds, and they can compete with the full-length antibody for specifically binding to the antigen. In general, with reference to Fundamental Immunology, Ch. 7 (Paul, W., ed., Edition 2, Raven Press, N.Y. (1989), the entire contents of which are incorporated herein by reference. Antigen-binding fragments can be produced by a recombinant DNA technology or through the enzymatic or chemical cleavage of a complete antibody. In some cases, the antigen-binding fragment comprise Fab, Fab', F(ab')2, (Fab)2, Fd, Fv, dAb and complementary determining region (CDR) fragments, single-chain antibodies (e.g., scFv), chimeric antibodies, diantibodies and a polypeptide that comprises at least a portion of an antibody sufficient to confer specific antigen binding capacity to the polypeptide. Conventional technologies known to technicians in the field (e.g., a recombinant DNA technology or an enzymatic or chemical cleavage process) can be used to obtain the antigen-binding fragments of an antibody from a given antibody, and screen the antigen-binding fragments of the antibody in terms of specificity in the same way as for complete antibodies. For example, pepsin can digest the antibodies in the hinge region below the disulfide bond so as to produce F(ab')2.

In the present application, the term "Fab" generally refers to antibody fragments composed of VL, VH, CL and CH1 domains.

In the present application, the term "Fab'" generally refers to antibody fragments with several additional residues at the carboxyl terminal of CH1 domain compared to Fab fragments. For example, Fab' may comprise one or more cysteine coming from the hinge region of the antibody.

In the present application, the term "F(ab)2" generally refers to antigen-binding fragments obtained from paired Fab fragments linked with cysteine.

In the present application, the term "dAb fragments" generally refers to antibody fragments composed of VH domains (Ward et al, Nature 341:544-546 (1989)).

In the present application, the term "complementary determining regions CDR" generally refers to the 3 hypervariable regions (HVRs) of the light chain variable region (VL) and the heavy chain variable region (VH), and the hypervariable regions are also known as complementary determining regions because these regions may form precise spatial complementarity with antigenic determinants.

In the present application, the term "Fv fragments" generally refers to antibody fragments composed of single-armed VL and VH domains of the antibody.

In the present application, the term "scFv" generally refers to molecules composed of the heavy chain variable region and the light chain variable region of the antibody linked by a short peptide linker, which is also known as a single-chain antibody.

In the present application, the term "monoclonal antibody" generally refers to a group of antibodies which are substantially homologous, and various antibodies contained in this group may be identical except for the possible presence of naturally occurring mutations in trace amounts. The monoclonal antibodies are highly specific, directly with respect to a single antigenic site. In addition, as opposed to a polyclonal antibody preparation that comprise different antibodies with respect to different determinants (epitopes), the modifier "monoclonal" of each monoclonal antibody with respect to the single determinant on the antigen is not interpreted as requiring the production of antibodies by any particular methods. For example, monoclonal antibodies may be prepared by a hybridoma technique or monoclonal antibodies may be produced in bacterial, eukaryotic animal or plant cells by a recombinant DNA process, and can also be obtained from phage antibody library, for example, using the technology described in Clackson et al., Nature, 352: 624-628(1991) and Marks et al., Mol. Biol., 222:581-597 (1991).

In the present application, the term "chimeric antibody" generally refers to such antibody, wherein a part of each heavy chain or light chain amino acid sequence is homologous to a corresponding amino acid sequence in an antibody from a particular species, or belongs to a particular category, and the remaining segments of the chain are homologous to the corresponding sequences of another species. For example, the variable regions of the light chain and the heavy chain are derived from the variable regions of an antibody in one animal species (e.g., mice, rats, etc.), while the constant part is homologous to the sequence of an antibody from another species (e.g., human). For example, to obtain chimeric antibodies, non-human B cells or hybridoma cells can be utilized to produce variable regions, and the constant regions combined with them are derived from human. The variable regions have the advantage of easy preparation, and their specificity is not affected by the source of the constant regions combined with them. Meanwhile, because the constant regions of chimeric antibodies may be derived from human, so chimeric antibodies are less likely to elicit an immune response at the time of injection than using antibodies with non-human derived constant regions.

In the present application, the term "humanized antibody" generally refers to a modified antibody which reduce the immunogenicity of an antibody, immunoglobulin binding protein and polypeptide derived from non-human species (e.g., mice or rats) to humans, and still retain the antigen-binding properties of the original antibody. For example, humanized antibody can be prepared by the genetic engineering technology, and non-human binding domains can be humanized using CDR grafting (Jones et al., Nature 321:522 (1986)) and the variant thereof by technical means including reshaping (Verhoeyen, et al., 1988 Science 239:1534-1536; Riechmann, et al., 1988 Nature 332:323-337; Tempest, et al., Bio/Technol 1991 9:266-271), hyperchimerization (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154) and veneering (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If other regions, for example, the hinge region and the constant region domains, are also derived from non-human sources, these regions may also be humanized.

In the present application, the term "fully human antibody" generally refers to an antibody obtained by expressing genes encoding human antibody in genetically engineered animal with antibody gene deletion. For example, by means of a transgenic or trans-chromosomal technology, all the genes that encode human antibody can be transferred into genetically engineered animal with antibody gene deletion so that the animal can express the human antibody.

As used in the present application, the term "sequence homology" generally refers to the sequence similarity or exchangeability between two or more polynucleotide sequences or between two or more polypeptide sequences. When a program (e.g., Emboss Needle or BestFit) is used to determine the sequence identity, similarity or homology between two different amino acid sequences, a default setting can be used, or a suitable rating matrix (such as blosum 45 or blosum 80) could be selected to optimize the scores of identity, similarity or homology. In some embodiments, homologous polynucleotides are those sequences which are hybridized under strict conditions, and they have a sequence identity of at least 60%, at least 65%, at least 70%, at least 80%, at least 90%, at least 95%, at least 97%, at least 98%, at least 99%, or even 100% compared with those sequences. When aligning sequences of equivalent length, the homologous polypeptides have a sequence identity of at least 80%, or at least 90%, or at least 95%, or at least 97%, or at least 98%, or may have a sequence identity of at least 99%.

In the present application, the terms "CD38", "CD38 protein" and "CD38 antigen" can be used interchangeably in the present application, and comprise any variants, isotypes and species homologues of human CD38, which can be expressed naturally by cells or expressed on the cells transfected with CD38 genes. The synonyms of CD38 well known in the art comprise ADP ribosyl cyclase 1, cADPr hydrolase 1, Cd38-rs1, cyclic ADP-ribose hydrolase 1, I-19 and NIM-R5 antigen. CD38 can be highly expressed on the surface of myeloma cells.

In the present application, the terms "AXL", "AXL protein" and "AXL antigen" can be used interchangeably in the present application, and generally refer to a kind of protein belonging to the tyrosine kinase family, which shares a common ligand Gash. In the present application, the high expression of AXL may be strongly associated with tumor formation, and AXL can be used as a marker of cancer progression. In the present application, the AXL may be a human AXL, the amino acid sequence of which is listed as AAH32229 in GenBank.

In the present application, the term "Trop2" generally refers to tumor-associated calcium signal transducer 2, which can be known as TACSTD2, EGP-1, GA733-1 or GP50, etc. Trop2 in cells may be localized in the cell membrane, and its positive staining sites may be mainly on the cell membrane. In normal tissues, Trop2 is minimally expressed, but it is overexpressed in tumor cells, so it can be used as the target of tumor therapy. In the present application, the Trop2 may be a human Trop2, the amino acid sequence of which is listed as NP_002344 in GenBank.

Generally, in a polypeptide chain, an amino group is linked with another carboxyl group in the polypeptide chain so as to become one chain, but at the two terminals of the protein, there remain amino acid residues that do not form peptide bonds respectively, which are a polypeptide chain terminal carrying free amino groups and a polypeptide chain terminal carrying carboxyl groups respectively. In the present application, the term "N-terminal" generally refers to the polypeptide chain terminal with an amino acid residue carrying free amino groups. In the present application, the term "C-terminal" generally refers to the polypeptide chain terminal with an amino acid residue carrying free carboxyl groups.

In the present application, the term "nucleic acid molecules" generally refers to nucleotides, deoxyribonucleotides or ribonucleotides or analogues thereof in isolated forms of any length which are isolated from natural environment or synthesized artificially.

In the present application, the term "immunoconjugate" generally refers to a polypeptide molecule with immune function in which one or more heterogenous molecules (including, but not limited to, cytotoxin) are conjugated. In the present application, "conjugate" and "link", "fusion" can be used interchangeably in the present application, and generally refers to that two or more chemical elements, sequences or components are linked together, for example by means including chemical conjugation or recombination. The heterogenous molecule may be a cytotoxin, a chemotherapeutic agent, etc. For example, the fusion protein of the present application can be conjugated with one or more heterogenous molecules (e.g., cytotoxin) to get the immunoconjugate.

In the present invention, the term "vector" refers to a nucleic acid delivery vehicle into which a polynucleotide encoding a certain protein can be inserted so that the protein can be expressed. The vector makes the genetic material element it carries be expressed in a host cell through transforming, transducing or transfecting the host cell. For example, the vectors comprise: plasmid; phagemid; cosmid; artificial chromosomes, such as yeast artificial chromosome (YAC), bacterial artificial chromosome (BAC) or P1-derived artificial chromosome (PAC); phages, such as λ phage or M13 phage; and animal viruses and the like. The variaties of animal viruses used as the vectors comprise retrovirus (including lentivirus), adenovirus, adeno-associated virus, herpes virus (e.g., herpes simplex virus), poxvirus, baculovirus, papilloma virus, papovavirus (e.g., SV40). A vector may contain various elements for controlling the expression, including a promoter sequence, a transcription initiation sequence, an enhancer sequence, a selection element and a reporter gene. In addition, the vector may also contain replication origin. The vector could also comprise a component that help it get into cell, such as a virion, a liposome or a protein coat, but not just these substances.

In the present application, the term "tumor" generally refers to neoplasms formed from the proliferation of local histocytes in the organisms of mammals (e.g., cells or parts thereof) under the action of various tumorigenic factors. In the present application, the tumor may comprise a solid tumor and s non-solid tumor. The solid tumor may comprise neuroglioma, germinoma, sarcoma, mesothelioma, placentoma, cerebral cancer, bone cancer, skin cancer, nasopharynx cancer, lung cancer, oral cancer, esophagus cancer, gastric cancer, liver cancer, pancreatic cancer, prostate cancer, intestinal cancer, breast cancer, cervical cancer, ovarian cancer and testicular cancer. In the present application, the non-solid tumor may comprise multiple myeloma, leukemia, Non-Hodgkin lymphoma, Hodgkin's lymphoma.

In the present application, the term "lymphoma" generally refers to a malignant tumor of the lymph system. The occurrence of lymphoma may be due to that lymph node cells or lymphocytes begin to reproduce uncontrollably and produce cancer cells with abnormal abilities which can invade other tissues throughout the body. The signs and symptoms of patients may comprise lymphadenectasis, fever, night sweating, emaciation or pruritus, as well as constantly feeling tired. There are various subtypes of lymphoma, in which the two main types are Hodgkin's lymphoma and Non-Hodgkin lymphoma. In the present application, the term "Hodgkin's lymphoma (HL)" generally refers to a lymphoma produced from lymphocytic white blood cells. About half of Hodgkin's lymphoma cases are caused by Epstein-Barr viruses. In the present application, the term "Non-Hodgkin lymphoma (NHL)" generally refers to other types of lymphoma except for Hodgkin's lymphoma.

In the present application, the term "leukemia" generally refers to a malignant proliferative disease of the hematopoietic system, and generally refers to a type of disease caused by massive proliferation or accumulation of leukemia cells. Clonal leukemia cells proliferate and accumulate in bone marrow and other hematopoietic tissues massively due to the mechanisms such as uncontrolled proliferation, dysdifferentiation, and blocked apoptosis, and infiltrater other non-hematopoietic tissues and organs, and at the same time inhibit normal hematopoietic function. Different degrees of anemia, bleeding, infective fever as well as swollen liver, spleen, lymph nodes and skeletal pain can be seen clinically.

In the present application, the term "multiple myeloma" generally refers to a malignant tumor invading the bone marrow caused by abnormal proliferation of plasmacytes. Multiple myeloma causes cancer cells to accumulate in the bone marrow, resulting in that healthy haemocytes are eliminated. Cancer cells produce abnormal proteins that may cause complications, rather than normal antibodies. The incidence of multiple myeloma may be increased in elderly population. Its chemotherapy regimen has low cell proliferation rate and strong drug resistance, thereby limiting the chemotherapeutic efficacy. Over 90% of multiple myeloma patients have chemotherapeutic resistance.

In the present application, the term "Raji cell" generally refers to continuous human cell lines which can produce Epstein-Barr viral strains. The viruses will transform umbilical cord lymphocytes and induce early antigens in Raji cells. Raji cells may be widely used as transfection hosts, and may also be used to know hematopoietic cells and other cell malignancies. In addition, Raji cells have and express several receptors of some complement components and Fc receptors of immunoglobulin G, so they can also be used to detect immune complexes.

In the present application, the term "autoimmune disease" generally refers to a disease caused by the immune response of the body to the autoantigens leading to damages to its own tissues. Autoimmune diseases can be divided into two major classes, i.e., organ specific autoimmune diseases and systemic autoimmune diseases. The organ specific autoimmune diseases may refer to pathological damages and dysfunctions of tissues and organs, but the organs are only limited to a certain organ targeted by an antibody or sensitized lymphocytes, and they may comprise chronic lymphocytic thyroiditis, hyperthyroidism, insulin-dependent diabetes mellitus, myasthenia gravis, chronic ulcerative colitis, pernicious anemia with chronic atrophic gastritis, goodpasture syndrome, pemphigus vulgaris, pemphigoid, primary biliary cirrhosis, multiple sclerosis and acute idiopathic polyneuritis. The systemic autoimmune diseases may be multiple organ damages throughout the body because of the extensive deposition of antigen-antibody complexes in the vascular wall, or may be caused by cellulose-like necrotizing inflammation of vascular wall and interstitium and subsequent proliferation of collagen fibers in multiple organs caused by immune injury; and the systemic autoimmune diseases may comprise systemic lupus erythematosus, rheumatoid arthritis, scleroderma and polyarteritis nodosa.

In the present application, the term "ADCC" is referred as antibody-dependent cell-mediated cytotoxicity (ADCC), and generally refers to that cells with killing activity recognize Fc segments coated on the target antigen by Fc receptors (FcR) expressed on the surface, thereby the effector cells of the immune system actively lyse target cells in which the membrane surface antigen has been bound by a specific antibody.

In the present application, the term "comprise" generally means including definitely specified features, but not excluding other factors.

In the present application, the term "about" generally refers to variations in a range of 0.5%-10% above or below a specified value, for example, variations in a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below a specified value.

Fusion Protein

In one aspect, the present application provides a fusion protein, the fusion protein may comprise a first binding domain and a second binding domain. The first binding domain can specifically bind a tumor-associated antigen; the second binding domain can specifically bind a CD47 protein, the second binding domain may comprise a mutant of a human SIRPα variant 1, and the mutant comprises substitution, deletion or addition of amino acid residues at one or more (e.g., 1-2, 1-3, 1-4, 1-5, 1-6, 1-7, 1-8, 1-9, 1-10 or more) positions from site 33 to site 149 compared to the sequence as shown in SEQ ID NO: 50. The fusion protein of the present application can specifically binds both the tumor-associated antigen and CD47 protein, thereby playing a role in the treatment of tumors and/or autoimmune diseases.

In the present application, the term "the first binding domain" generally refers to a domain that can specifically bind a tumor-associated antigen. The term "the second binding domain" generally refers to a domain that can specifically bind a CD47 protein.

In the present application, the tumor-associated antigen may comprise a tumor-associated antigen associated with a non-solid tumor and/or a solid tumor. For example, the tumor-associated antigen may be selected from the group consisting of: CD38, AXL and Trop2.

The Second Binding Domain that Specifically Binds CD47

In the present application, the mutant (e.g., a mutant of a human SIRPα variant 1 that specifically binds a CD47 protein) comprises amino acid substitutions at one or more (e.g., 1-2, 1-3, 1-4, 1-5, 1-6, 1-7, 1-8, 1-9, 1-10 or more) amino acid residues selected from the group consisting of: R22, I29, I61, V63, E77, Q82, K83, E84, V93, D95, D96, K98, N100, R107, G109 and V132.

In the present application, the positions of amino acid residues in the amino acid substitutions mean the numbers of the residues determined based on the amino acid sequence as shown in SEQ ID NO: 50.

In the present application, "amino acid substitution Xn" means that an amino acid substitution occurs at the residue X of site n in the corresponding amino acid sequence as shown in SEQ ID NO: 50, in which n is a positive integer, X is the abbreviation of any one amino acid residue. For example, "amino acid substitution I61" indicates that an amino acid substitution occurs at the residue I of site 61 in the corresponding amino acid sequence as shown in SEQ ID NO: 50.

In the present application, the amino acid substitutions may be nonconservative substitutions. The nonconservative substitutions may comprise changing amino acid residues in target proteins or polypeptides in a nonconservative form, for example, changing an amino acid residue with a certain side chain size or certain property (e.g., hydrophilic) into another amino acid residue with different side chain size or different property (e.g., hydrophobic).

In the present application, the amino acid substitutions may also be conservative substitutions. The conservative substitutions may comprise changing amino acid residues in target proteins or polypeptides in a conservative form, for example, changing an amino acid residue with a certain side chain size or certain property (e.g., hydrophilic) into another amino acid residue with the same or similar side chain size or the same or similar property (e.g., still hydrophilic). Such conservative substitutions generally do not greatly affect the structure or function of the resulting protein. In the present application, the amino acid sequence variant of the fusion protein or a fragment thereof may comprise conservative amino acid substitutions which do not significantly change the structure or function of the protein (e.g., a mutant of a human SIRPα variant 1 that blocks CD47 and specifically binds a CD47 protein).

As an example, the mutual substitutions of various amino acids in each group of the following groups can be considered as conservative substitutions in the present application: a group of amino acids with nonpolar side chains: alanine, valine, leucine, isoleucine, proline, phenylalanine, tryptophan and methionine; a group of uncharged amino acids with polar side chains: glycine, serine, threonine, cysteine, tyrosine, asparagine and glutamine; a group of negatively charged amino acids with polar side chains: aspartic acid and glutamic acid; positively charged basic amino acids: lysine, arginine and histidine; and amino acids carrying phenyl groups: phenylalanine, tryptophan and tyrosine.

In the present application, the mutant may comprise amino acid substitutions at amino acid residues selected from the group consisting of: (1) I61, V63, E77, E84, V93, L96, K98, N100 and V132; (2) I61, E77, Q82, K83 and E84; (3) I61, V63, K83, E84 and V132; (4) I61, E77, E84, R107 and V132; (5) I61, V63, E77, K83, E84 and N100; (6) I61, E77, Q82, K83, E84 and R107; (7) I61, E77, Q82, E84, V93, L96, N100, R107, G109 and V132; (8) I61, E77, Q82, K83, E84 and V132; (9) I61; (10) I61, D95, L96, G109 and V132; (11) I61, D95, L96, K98, G109 and V132; (12) I61, E77, E84, V93, R107 and V132; (13) E77, L96, N100, G109 and V132; (14) I61, V63, Q82, E84, D95, L96, N100 and V132; (15) I61, E77, Q82, K83, E84, V93, D95, L96, K98, N100 and V132; (16) I61, E77, Q82, K83, E84 and V93; (17) I61, V63, E77, K83, E84, D95, L96, K98 and N100; (18) I61, V63, E77, K83, D95, L96, K98, N100 and G109; (19) I61, E77, Q82, E84, V93, D95, L96, K98 and N100; and (20) I61, V63, E77, Q82 and E84.

In the present application, the mutant may comprise one or more (e.g., 1-2, 1-3, 1-4, 1-5, 1-6, 1-7, 1-8, 1-9, 1-10 or more) amino acid substitutions selected from the group consisting of: R22C, I29L, I61L/V/F, V63I, E77I/N/Q/K/H/M/R/N/V/L, Q82S/R/G/N, K83R, E84K/H/D/R/G, V93L/A, D95H/R/E, D96S/T, K98R, N100G/K/D/E, R107N/S, G109R/11 and V132L/R/I/S.

In the present application, the amino acid substitution "XnY/Z" means that the residue X of site n in the corresponding amino acid sequence as shown in SEQ ID NO: 50 is substituted by an amino acid residue Y or an amino acid residue Z, in which n is a positive integer, X, Y and Z are the abbreviations of any amino acid residues independently, and X is different from Y or Z. For example, the amino acid substitution "I61L/V/F" means that the residue I of site 61 in the corresponding amino acid sequence as shown in SEQ ID NO: 50 is substituted by an amino acid residue L, V or F.

In the present application, the mutant may comprise amino acid substitutions selected from the group consisting of: (1) I61L, V63I, E77I, E84K, V93L, L96S, K98R, N100G and V132L; (2) I61V, E77N, Q82S, K83R and E84H; (3) I61F, V63I, K83R, E84K and V132I; (4) I61L, E77Q, E84D, R107N and V132I; (5) I61L, V63I, E77K, K83R, E84D and N100G; (6) I61V, E77H, Q82R, K83R, E84H and R107S; (7) I61L, E77I, Q82G, E84R, V93L, L96T, N100G, R107S, G109R and V132R; (8) I61L, E77M, Q82G, K83R, E84D and V132L; (9) I61L; (10) I61F, D95H, L96S, G109H and V132S; (11) I61F, D95H, L96S, K98R, G109H and V132S; (12) I61L, E77Q, E84D, V93A, R107N and V132I; (13) E77K, L96S, N100K, G109H and V132L; (14) I61L, V63I, Q82G, E84G, D95R, L96S, N100D and V132I; (15) I61L, E77R, Q82N, K83R, E84G, V93L, D95E, L96T, K98R, N100D and V132L; (16) I61V, E77N, Q82S, K83R, E84H and V93A; (17) I61V, V63I, E77V, K83R, E84D, D95E, L96T, K98R and N100E; (18) I61L, V63I, E77V, K83R, D95E, L96S, K98R, N100D and G109R; (19) I61V, E77L, Q82G, E84G, V93L, D95E, L96T, K98R and N100G; and (20) I61L, V63I, E77N, Q82G and E84G.

In the present application, based on the human SIRPα variant 1 (the amino acid sequence as shown in SEQ ID NO: 50, i.e., residues at sites 33 to site 149 in the amino acid sequence of a human SIRPα), the mutants of the SIRPα variant 1 which comprise the amino acid substitutions of the above groups (1)-(20) respectively are named as M1, M5, M12, M35, M37, M41, M57, M67, M81, M82, M84, M91, M99, M102, M111, M122, M126, M130, M135 and M145 successively. The mutants of the SIRPα variant 1 can successively comprise the amino acid sequences as shown in SEQ ID NO: 51 to SEQ ID NO: 70.

In some embodiments, the mutant of the SIRPα variant 1 is M91, and the mutant of the SIRPα variant 1 comprises the amino acid sequence as shown in SEQ ID NO: 62.

The First Binding Domain that Specifically Binds a Tumor-Associated Antigen

In the present application, the first binding domain may comprise an antibody or an antigen-binding fragment or a variant thereof. For example, the antibody may be selected from the group consisting of: monoclonal antibodies, single-chain antibodies, chimeric antibodies, humanized antibodies and fully human antibodies. For example, the antigen-binding fragment is selected from the group consisting of: Fab, Fab', (Fab')2, F(ab)2, dAb, an isolated complementary determining regions CDR, Fv and scFv.

In the present application, the variant of the antibody or the antigen-binding fragment thereof may be a protein or polypeptide with substitution, deletion or addition of one or more (e.g., 1-2, 1-3, 1-4, 1-5, 1-6, 1-7, 1-8, 1-9, 1-10 or more) amino acids in the antibody or the antigen-binding fragment thereof. Alternatively, the variant of the antibody or the antigen-binding fragment thereof may be a protein or polypeptide with a sequence homology of at least 90% (e.g., at least 90%, at least 91%, at least 92%, at least 93%, at least 94%, at least 95%, at least 96%, at least 97%, at least 98%, at least 99%, or at least 100%) with the antibody or the antigen-binding fragment thereof.

The First Binding Domain that Specifically Binds CD38

The antibody or the antigen-binding fragment or the variant thereof in the present application may kill tumor cells and/or inhibit the tumor growth by specifically binding the CD38 protein. For example, the tumor may comprise a CD38 positive tumor. For example, the CD38 positive tumor may be selected from the group consisting of: myeloma, lymphoma and leukemia. Further for example, the tumor is selected from the group consisting of: Non-Hodgkin lymphoma and Hodgkin's lymphoma. The tumor cells may be selected from the group consisting of: Raji cells, Daudi cells, Ramos cells and RPMI8226 cells. In the present application, the antibody, the antigen-binding fragment or the variant thereof may kill the cells of multiple myeloma, lymphoma, leukemia, Non-Hodgkin lymphoma and Hodgkin's lymphoma or inhibit the growth of multiple myeloma, lymphoma, leukemia, Non-Hodgkin lymphoma and Hodgkin's lymphoma.

The CD38 protein of the present application may be a human CD38 protein or a functional fragment thereof. For example, the CD38 protein may not be a mouse CD38 protein, or may not be a rat CD38 protein. In some embodiments, the antibody, the antigen-binding fragment or the variant thereof in the present application substantially does not bind the mouse CD38 protein or the rat CD38 protein.

The antibody, the antigen-binding fragment or the variant thereof in the present application can compete with the reference antibody to bind the CD38 protein. The reference antibody may comprise a light chain variable region and a heavy chain variable region. For example, the light chain variable region of the reference antibody may comprise LCDR1-3, the amino acid sequences of the LCDR1-3 are SEQ ID NO: 1, SEQ ID NO: 2 and SEQ ID NO: 3, successively. The heavy chain variable region of the reference antibody may comprise HCDR1-3, the amino acid sequences of the HCDR1-3 are SEQ ID NO: 4, SEQ ID NO: 5 and SEQ ID NO: 6, successively.

For example, the amino acid sequence of the light chain variable region of the reference antibody may be: SEQ ID NO: 7, and the amino acid sequence of the heavy chain variable region of the reference antibody may be: SEQ ID NO: 8. Further for example, the light chain of the reference antibody may comprise any one of the amino acid sequences selected from those as shown in the group consisting of: SEQ ID NO: 11, SEQ ID NO: 16, SEQ ID NO: 18 and SEQ ID NO: 20; and the heavy chain of the reference antibody may comprise any one of the amino acid sequences selected from those as shown in the group consisting of: SEQ ID NO: 13, SEQ ID NO: 17, SEQ ID NO: 19 and SEQ ID NO: 21. For example, the light chain of the reference antibody may comprise the amino acid sequence as shown in SEQ ID NO: 11, and the heavy chain of the reference antibody may comprise the amino acid sequence as shown in SEQ ID NO: 13. For example, the light chain of the reference antibody may comprise the amino acid sequence as shown in SEQ ID NO: 16, and the heavy chain of the reference antibody may comprise the amino acid sequence as shown in SEQ ID NO: 17. For example, the light chain of the reference antibody may comprise the amino acid sequence as shown in SEQ ID NO: 18, and the heavy chain of the reference antibody may comprise the amino acid sequence as shown in SEQ ID NO: 19. For example, the light chain of the reference antibody may comprise the amino acid sequence as shown in SEQ ID NO: 20, and the heavy chain of the reference antibody may comprise the amino acid sequence as shown in SEQ ID NO: 21.

The antibody, the antigen-binding fragment or the variant thereof in the present application may comprise a light chain of the antibody or a fragment thereof. For example, the light chain of the antibody or the fragment thereof may comprise an Igκ constant region, for example, may comprise a human Igκ constant region.

For example, the light chain of the antibody or the fragment thereof may comprise LCDR1, and the LCDR1 may comprise an amino acid sequence as below: SEQ ID NO: 1. The light chain of the antibody or the fragment thereof may comprise LCDR2, and the LCDR2 may comprise an amino acid sequence as below: SEQ ID NO: 2. The light chain of the antibody or the fragment thereof may comprise LCDR3, and the LCDR3 may comprise an amino acid sequence as below: SEQ ID NO: 3.

The light chain of the antibody or the fragment thereof in the present application may comprise a light chain variable region VL, and the amino acid sequence of the light chain variable region VL may be: SEQ ID NO: 7. In some embodiments, the light chain of the antibody or the fragment thereof may comprise any one of the amino acid sequences selected from those as shown in the group consisting of: SEQ ID NO: 11, SEQ ID NO: 16, SEQ ID NO: 18 and SEQ ID NO: 20.

The antibody or the antigen-binding fragment thereof in the present application may comprise a heavy chain of the antibody or a fragment thereof. For example, the heavy chain of the antibody or the fragment thereof further comprises a human constant region. Where, the human constant region may comprise a human IgG constant region. Where, the IgG constant region may comprise a human IgG1 constant region or IgG4.

For example, the heavy chain of the antibody or the fragment thereof may comprise HCDR1, and the HCDR1 may comprise an amino acid sequence as below: SEQ ID NO: 4. The heavy chain of the antibody or the fragment thereof may comprise HCDR2, and the HCDR2 may comprise an amino acid sequence as below: SEQ ID NO: 5. Further for example, the heavy chain of the antibody or the fragment thereof may comprise HCDR3, and the HCDR3 may comprise an amino acid sequence as below: SEQ ID NO: 6.

The heavy chain of the antibody or the fragment thereof may comprise a heavy chain variable region VH, and the heavy chain variable region VH may comprise an amino acid sequence as below: SEQ ID NO: 8. In some embodiments, the heavy chain of the antibody may comprise any one of the amino acid sequences selected from those as shown in the group consisting of: SEQ ID NO: 13, SEQ ID NO: 17, SEQ ID NO: 19 and SEQ ID NO: 21.

In some embodiments, in the antibody or the antigen-binding fragment thereof in the present application, the amino acid sequence of LCDR1 may comprise SEQ ID NO: 1; the amino acid sequence of LCDR2 may comprise SEQ ID NO: 2; the amino acid sequence of LCDR3 may comprise SEQ ID NO: 3; and the amino acid sequence of HCDR1 may comprise SEQ ID NO: 4; or the amino acid sequence of HCDR2 may comprise SEQ ID NO: 5; the amino acid sequence of HCDR3 may comprise SEQ ID NO: 6. For example, the antibody or the antigen-binding fragment thereof may comprise an antibody SG003 or an antibody having the same LCDR1-3 and HCDR1-3 as the antibody SG003. In some embodiments, the light chain of the antibody or the antigen-binding fragment thereof in the present application may comprise a light chain variable region, the amino acid sequence of which may comprise SEQ ID NO: 7; and the heavy chain thereof may comprise a heavy chain variable region, the amino acid sequence of which may comprise SEQ ID NO: 8. For example, the antibody or the antigen-binding fragment thereof may comprise an antibody SG003 or an antibody having the same light chain variable region and heavy chain variable region as the antibody SG003. In some embodiments, the antibody or the antigen-binding fragment thereof in the present application may comprise a light chain and a heavy chain, the amino acid sequence of the light chain is shown in SEQ ID NO: 11 and the amino acid sequence of the heavy chain is shown in SEQ ID NO: 13. For example, the antibody or the antigen-binding fragment thereof may comprise an antibody SG003 or have the same amino acid sequences for the light chain and the heavy chain as the antibody SG003.

In some embodiments, the antibody of the present application may be SG003. The amino acid sequences of LCDR1-3 in the antibody SG003 are shown in SEQ ID NO: 1, SEQ ID NO: 2 and SEQ ID NO: 3, respectively; the amino acid sequence of VL is shown in SEQ ID NO: 7; the amino acid sequences of HCDR1-3 are shown in SEQ ID NO: 4, SEQ ID NO: 5 and SEQ ID NO: 6, respectively; the amino acid sequence of VH is shown in SEQ ID NO: 8; the amino acid sequence of the light chain is shown in SEQ ID NO: 11; and the amino acid sequence of the heavy chain is shown in SEQ ID NO: 13.

The antibody or the antigen-binding fragment or the variant thereof in the present application may also comprise one or more random mutations (e.g., one or more, e.g. one or several amino acid substitutions) in the amino acid sequence of the light chain and/or the heavy chain of SG003. For example, the antibody, the antigen-binding fragment or the variant thereof may comprise one or more random mutations (e.g., one or more, e.g. one or several amino acid substitutions) at one or more sites of framework regions L-FR1-4 in the light chain variable region of SG003, and/or comprise one or more random mutations (e.g., one or more, e.g. one or several amino acid substitutions) at one or more sites of framework regions H-FR1-4 in the heavy chain variable region of SG003. For example, after the random mutations, the light chain of the antibody or the antigen-binding fragment or the variant thereof may comprise any one of the amino acid sequences selected from those as shown in the group consisting of: SEQ ID NO: 16, SEQ ID NO: 18 and SEQ ID NO: 20; and/or the heavy chain of the antibody or the antigen-binding fragment or the variant thereof may comprise any one of the amino acid sequences selected from those as shown in the group consisting of: SEQ ID NO: 17, SEQ ID NO: 19 and SEQ ID NO: 21. The CD38 antibody or the antigen-binding fragment or the variant thereof after random mutations still have the ability of specifically binding the human CD38 protein.

In some embodiments, in the, the amino acid sequence of the light chain of the antibody or the antigen-binding fragment thereof in the present application comprises SEQ ID NO: 11, and the amino acid sequence of the heavy chain comprises SEQ ID NO: 13; alternatively, in the antibody or the antigen-binding fragment thereof in the present application, the amino acid sequence of the light chain comprises SEQ ID NO: 16, and the amino acid sequence of the heavy chain comprises SEQ ID NO: 17; alternatively, the amino acid sequence of the light chain of the antibody or the antigen-binding fragment thereof in the present application comprises SEQ ID NO: 18, and the amino acid sequence of the heavy chain comprises SEQ ID NO: 19; alternatively, in the antibody or the antigen-binding fragment thereof in the present application, the amino acid sequence of the light chain comprises SEQ ID NO: 20, and the amino acid sequence of the heavy chain comprises SEQ ID NO: 21.

The First Binding Domain that Specifically Binds AXL

The antibody or the antigen-binding fragment or the variant thereof in the present application may kill tumor cells and/or inhibit the tumor growth by specifically binding AXL. For example, the AXL may be a human AXL.

The antibody, the antigen-binding fragment or the variant thereof in the present application can compete with the reference antibody to bind the AXL protein. The reference antibody may comprise a light chain variable region and a heavy chain variable region. For example, the light chain variable region of the reference antibody may comprise LCDR1-3, the amino acid sequences of the LCDR1-3 are SEQ ID NO: 22, SEQ ID NO: 23 and SEQ ID NO: 24, successively. The heavy chain variable region of the reference antibody may comprise HCDR1-3, the amino acid sequences of the HCDR1-3 are SEQ ID NO: 25, SEQ ID NO: 26 and SEQ ID NO: 27, successively.

For example, the amino acid sequence of the light chain variable region of the reference antibody may be: SEQ ID NO: 28, and the amino acid sequence of the heavy chain variable region of the reference antibody may be: SEQ ID NO: 29. Further for example, the amino acid sequence of the light chain of the reference antibody may be: SEQ ID NO: 32; and the amino acid sequence of the heavy chain of the reference antibody may be: SEQ ID NO: 34.

The antibody, the antigen-binding fragment or the variant thereof in the present application may comprise a light chain of the antibody or a fragment thereof. For example, the light chain of the antibody or the fragment thereof may comprise an Igκ constant region, for example may comprise a human Igκ constant region.

For example, the light chain of the antibody or the fragment thereof may comprise LCDR1, and the LCDR1 may comprise an amino acid sequence as below: SEQ ID NO: 22. The light chain of the antibody or the fragment thereof may comprise LCDR2, and the LCDR2 may comprise an amino acid sequence as below: SEQ ID NO: 23. The light chain of the antibody or the fragment thereof may comprise LCDR3, and the LCDR3 may comprise an amino acid sequence as below: SEQ ID NO: 24.

The light chain of the antibody of the present application or the fragment thereof may comprise a light chain variable region VL, and the amino acid sequence of the light chain variable region VL may be: SEQ ID NO: 28. In some embodiments, the amino acid sequence of the light chain of the antibody or the fragment thereof may be: SEQ ID NO: 32.

The antibody or the antigen-binding fragment thereof in the present application may comprise a heavy chain of the antibody or a fragment thereof. For example, the heavy chain of the antibody or the fragment thereof further comprises a human constant region. Where, the human constant region may comprise a human IgG constant region. Where, the IgG constant region may comprise a human IgG1 constant region or IgG4.

For example, the heavy chain of the antibody or the fragment thereof may comprise HCDR1, and the HCDR1 may comprise an amino acid sequence as below: SEQ ID NO: 25. The heavy chain of the antibody or the fragment thereof may comprise HCDR2, and the HCDR2 may comprise an amino acid sequence as below: SEQ ID NO: 26. Further for example, the heavy chain of the antibody or the fragment thereof may comprise HCDR3, and the HCDR3 may comprise an amino acid sequence as below: SEQ ID NO: 27.

The heavy chain of the antibody or the fragment thereof may comprise a heavy chain variable region VH, and the amino acid sequence of the heavy chain variable region VH may be: SEQ ID NO: 29. In some embodiments, the amino acid sequence of the heavy chain of the antibody or the fragment thereof may be: SEQ ID NO: 34.

In some embodiments, the amino acid sequence of LCDR1 of the antibody or the antigen-binding fragment thereof in the present application may comprise SEQ ID NO: 22 or a variant thereof; the amino acid sequence of LCDR2 may comprise SEQ ID NO: 23 or a variant thereof; the amino acid sequence of LCDR3 may comprise SEQ ID NO: 24 or a variant thereof; and the amino acid sequence of HCDR1 may comprise SEQ ID NO: 25 or a variant thereof; the amino acid sequence of HCDR2 may comprise SEQ ID NO: 26 or a variant thereof; the amino acid sequence of HCDR3 may comprise SEQ ID NO: 27 or a variant thereof. For example, the antibody or the antigen-binding fragment thereof may comprise an antibody C6G12 or an antibody having the same LCDR1-3 and HCDR1-3 as the antibody C6G12. In some embodiments, the light chain of the antibody or the antigen-binding fragment thereof in the present application may comprise a light chain variable region, and the amino acid sequence of the light chain variable region may comprise SEQ ID NO: 28 or a variant thereof; and the heavy chain thereof may comprise a heavy chain variable region, and the amino acid sequence of the heavy chain variable region may comprise SEQ ID NO: 29 or a variant thereof. For example, the antibody or the antigen-binding fragment thereof may comprise an antibody C6G12 or an antibody having the same light chain variable region and heavy chain variable region as the antibody C6G12. In some embodiments, the antibody or the antigen-binding fragment thereof in the present application may comprise a light chain and a heavy chain, the amino acid sequence of the light chain is shown in SEQ ID NO: 32 and the amino acid sequence of the heavy chain is shown in SEQ ID NO: 34. For example, the antibody or the antigen-binding fragment thereof may comprise an antibody C6G12 or have the same amino acid sequences for the light chain and the heavy chain as the antibody C6G12.

In some embodiments, the antibody of the present application may be C6G12. the amino acid sequences of LCDR1-3 of the antibody C6G12 are shown in SEQ ID NO: 22, SEQ ID NO: 23 and SEQ ID NO: 24, respectively; the amino acid sequence of VL is shown in SEQ ID NO: 28; the amino acid sequences of HCDR1-3 are shown in SEQ ID NO: 25, SEQ ID NO: 26 and SEQ ID NO: 27, respectively; the amino acid sequence of VH is shown in SEQ ID NO: 29; the amino acid sequence of the light chain is shown in SEQ ID NO: 32; and the amino acid sequence of the heavy chain is shown in SEQ ID NO: 34.

The First Binding Domain that Specifically Binds Trop2

The antibody or the antigen-binding fragment or the variant thereof in the present application may kill tumor cells and/or inhibit the tumor growth by specifically binding Trop2. For example, the Trop2 may be a human Trop2.

The antibody, the antigen-binding fragment or the variant thereof in the present application can compete with the reference antibody to bind the Trop2 protein. The reference antibody may comprise a light chain variable region and a heavy chain variable region. For example, the light chain variable region of the reference antibody may comprise LCDR1-3, the amino acid sequences of the LCDR1-3 are SEQ ID NO: 36, SEQ ID NO: 37 and SEQ ID NO: 38, successively. The heavy chain variable region of the reference antibody may comprise HCDR1-3, the amino acid sequences of the HCDR1-3 are SEQ ID NO: 39, SEQ ID NO: 40 and SEQ ID NO: 41, successively.

For example, the amino acid sequence of the light chain variable region of the reference antibody may be: SEQ ID NO: 42, and the amino acid sequence of the heavy chain variable region of the reference antibody may be: SEQ ID NO: 43. Further for example, the amino acid sequence of the light chain of the reference antibody may be: SEQ ID NO: 46; and the amino acid sequence of the heavy chain of the reference antibody may be: SEQ ID NO: 48. For example, the light chain of the reference antibody may comprise an amino acid sequence as shown in SEQ ID NO: 46, and the heavy chain of the reference antibody may comprise an amino acid sequence as shown in SEQ ID NO: 48.

The antibody, the antigen-binding fragment or the variant thereof in the present application may comprise a light chain of the antibody or a fragment thereof. For example, the light chain of the antibody or the fragment thereof may comprise an Igκ constant region, for example may comprise a human Igκ constant region.

For example, the light chain of the antibody or the fragment thereof may comprise LCDR1, and the LCDR1 may comprise an amino acid sequence as below: SEQ ID NO: 36. The light chain of the antibody or the fragment thereof may comprise LCDR2, and the LCDR2 may comprise an amino acid sequence as below: SEQ ID NO: 37. The light chain of the antibody or the fragment thereof may comprise LCDR3, and the LCDR3 may comprise an amino acid sequence as below: SEQ ID NO: 38.

The light chain of the antibody or the fragment thereof in the present application may comprise a light chain variable region VL, and the light chain variable region VL may comprise an amino acid sequence as below: SEQ ID NO: 42. In some embodiments, the amino acid sequence of the light chain of the antibody or the fragment thereof may be: SEQ ID NO: 46.

The antibody or the antigen-binding fragment thereof in the present application may comprise a heavy chain of the antibody or a fragment thereof. For example, the heavy chain of the antibody or the fragment thereof further comprises a human constant region. Where, the human constant region may comprise a human IgG constant region. Where, the IgG constant region may comprise a human IgG1 constant region or IgG4.

For example, the heavy chain of the antibody or the fragment thereof may comprise HCDR1, and the HCDR1 may comprise an amino acid sequence as below: SEQ ID NO: 39. The heavy chain of the antibody or the fragment thereof may comprise HCDR2, and the HCDR2 may comprise an amino acid sequence as below: SEQ ID NO: 40. Further for example, the heavy chain of the antibody or the fragment thereof may comprise HCDR3, and the HCDR3 may comprise an amino acid sequence as below: SEQ ID NO: 41.

The heavy chain of the antibody or the fragment thereof may comprise a heavy chain variable region VH, and the heavy chain variable region VH may comprise an amino acid sequence as below: SEQ ID NO: 43. In some embodiments, the amino acid sequence of the heavy chain of the antibody or the fragment thereof may be: SEQ ID NO: 48.

In some embodiments, in the antibody or the antigen-binding fragment thereof in the present application, the amino acid sequence of LCDR1 may comprise SEQ ID NO: 36 or a variant thereof; the amino acid sequence of LCDR2 may comprise SEQ ID NO: 37 or a variant thereof; the amino acid sequence of LCDR3 may comprise SEQ ID NO: 38 or a variant thereof; and the amino acid sequence of HCDR1 may comprise SEQ ID NO: 39 or a variant thereof; the amino acid sequence of HCDR2 may comprise SEQ ID NO: 40 or a variant thereof; the amino acid sequence of HCDR3 may comprise SEQ ID NO: 41 or a variant thereof. For example, the antibody or the antigen-binding fragment thereof may comprise an antibody SG701 or an antibody having the same LCDR1-3 and HCDR1-3 as the antibody SG701. In some embodiments, the light chain of the antibody or the antigen-binding fragment thereof in the present application may comprise a light chain variable region, the amino acid sequence of the light chain variable region may comprise SEQ ID NO: 42 or a variant thereof, and the heavy chain thereof may comprise a heavy chain variable region, the amino acid sequence of the heavy chain variable region may comprise SEQ ID NO: 43 or a variant thereof. For example, the antibody or the antigen-binding fragment thereof may comprise an antibody SG701 or an antibody having the same light chain variable region and heavy chain variable region as the antibody SG701. In some embodiments, the antibody or the antigen-binding fragment thereof in the present application may comprise a light chain and a heavy chain, the amino acid sequence of the light chain is shown in SEQ ID NO: 46 and the amino acid sequence of the heavy chain is shown in SEQ ID NO: 48. For example, the antibody or the antigen-binding fragment thereof may comprise an antibody SG701 or have the same amino acid sequences for the light chain and the heavy chain as the antibody SG701.

In some embodiments, the antibody of the present application may be SG701. The amino acid sequences of LCDR1-3 of the antibody SG701 are shown in SEQ ID NO: 36, SEQ ID NO: 37 and SEQ ID NO: 38, respectively; the amino acid sequence of VL is shown in SEQ ID NO: 42; the amino acid sequences of HCDR1-3 are shown in SEQ ID NO: 39, SEQ ID NO: 40 and SEQ ID NO: 41, respectively; the amino acid sequence of VH is shown in SEQ ID NO: 43; the amino acid sequence of the light chain is shown in SEQ ID NO: 46; and the amino acid sequence of the heavy chain is shown in SEQ ID NO: 48.

The Linkage Between the First Binding Domain and the Second Binding Domain

In the present application, the first binding domain may be located at the N-terminal of the second binding domain. For example, the C-terminal of the first binding domain may be linked to the N-terminal of the second binding domain indirectly by a linker. In some instances, the C-terminal of the first binding domain may also be linked to the N-terminal of the second binding domain directly (e.g., in-frame).

In the present application, the fusion protein may also comprise a linker, which may be located at the C-terminal of the first binding domain and located at the N-terminal of the second binding domain. For example, in the fusion protein, the C-terminal of the first binding domain may be linked to the N-terminal of the linker, and the C-terminal of the linker may be linked to the N-terminal of the second binding domain. For example, the first binding domain, the linker and the second binding domain can be comprised in the fusion protein successively from N-terminal to C-terminal.

In the present application, the linker may comprise an amino acid sequence as shown in any one of SEQ ID NOs: 73-74.

In some instances, the fusion protein may comprise at least 2 (e.g., at least 2, at least 3, at least 4, at least 5, at least 6, at least 7, at least 8, at least 9, at least 10, or more) of the second binding domain. In the present application, each of the second binding domains can be located at the C-terminal of the first binding domain respectively. In the present application, the more than two second binding domains can be linked to the C-terminal of the first binding domain directly or indirectly.

In the present application, the fusion protein may comprise a first binding domain that specifically binds a CD38 antigen, and a second binding domain that specifically binds a CD47 protein, in which the first binding domain may comprise an antibody that specifically binds a CD38 antigen or an antigen-binding fragment or a variant thereof, the second binding domain may comprise a mutant of a human SIRPα variant 1, the C-terminal of the antibody that specifically binds the CD38 antigen or the antigen-binding fragment or the variant thereof can be directly or indirectly linked to the N-terminal of the mutant of the human SIRPα variant 1. For example, the second binding domain may comprise at least two mutants of the human SIRPα variant 1, and the N-terminals of the two mutants of the human SIRPα variant 1 are linked to the C-terminals of the antibody that specifically binds the CD38 antigen or the antigen-binding fragment or the variant thereof, respectively.

For example, as shown in FIG. 1, the first binding domain of the fusion protein (SG3847L1) may comprise SG003, and the second binding domain thereof may comprise two mutants M91 of the SIRPα variant 1, the sequence of the used linker 1 is shown in SEQ ID NO: 73, the N-terminals of the two M91 are linked to the C-terminals of two heavy chains of SG003 through the linker 1 respectively. In the fusion protein, M91 is linked to the C-terminal of the heavy chain of SG003 to get the second polypeptide chain, and the light chain of SG003 may be named as the first polypeptide chain. The amino acid sequences of the second polypeptide chain and the first polypeptide chain of SG3847L1 are shown in SEQ ID NO: 75 and SEQ ID NO: 11 respectively.

For example, as shown in FIG. 1, the first binding domain of the fusion protein (SG3847L2) may comprise SG003, the second binding domain thereof may comprise two mutants M91 of the SIRPα variant 1, the sequence of the used linker 2 is shown in SEQ ID NO: 74, the N-terminals of the two M91 are linked to the C-terminals of two heavy chains of SG003 through the linker 2 respectively. In the fusion protein, M91 is linked to the C-terminal of the heavy chain of SG003 to get the second polypeptide chain, and the light chain of SG003 may be named as the first polypeptide chain. The amino acid sequences of the second polypeptide chain and the first polypeptide chain of SG3847L2 are shown in SEQ ID NO: 76 and SEQ ID NO: 11 respectively.

In the present application, the fusion protein may comprise a first binding domain that specifically binds a Trop2 antigen, and a second binding domain that specifically binds a CD47 protein, in which the first binding domain may comprise an antibody that specifically binds a Trop2 antigen or an antigen-binding fragment or a variant thereof, the second binding domain may comprise a mutant of a human SIRPα variant 1, and the C-terminal of the antibody that specifically binds a Trop2 antigen or the antigen-binding fragment or the variant thereof can be directly or indirectly linked to the N-terminal of the mutant of the human SIRPα variant 1. In the present application, the second binding domain may comprise at least two mutants of a human SIRPα variant 1, and the N-terminals of the two mutants of the human SIRPα variant 1 are linked to the C-terminals of an antibody that specifically binds an AXL antigen or an antigen-binding fragment or a variant thereof, respectively.

For example, as shown in FIG. 1, the first binding domain of the fusion protein (SGTrop247) may comprise an antibody SG701, the second binding domain thereof may comprise two mutants M91 of the SIRPα variant 1, the sequence of the used linker is shown in SEQ ID NO: 74, the N-terminals of the two M91 are linked to the C-terminals of two heavy chains of SG701 through the linker respectively. In the fusion protein, M91 is linked to the C-terminal of the heavy chain of SG701 to get the second polypeptide chain, and the light chain of SG701 may be named as the first polypeptide chain. The amino acid sequences of the second polypeptide chain and the first polypeptide chain of SGTrop247 are shown in SEQ ID NO: 78 and SEQ ID NO: 46 respectively.

In the present application, the fusion protein may comprise a first binding domain that specifically binds an AXL antigen, and a second binding domain that specifically binds a CD47 protein, wherein the first binding domain may comprise an antibody that specifically binds an AXL antigen or an antigen-binding fragment or a variant thereof, the second binding domain may comprise a mutant of a human SIRPα variant 1, the C-terminal of the antibody that specifically binds the AXL antigen or the antigen-binding fragment or the variant thereof can be directly or indirectly linked to the N-terminal of the mutant of the human SIRPα variant 1. In the present application, the second binding domain may comprise at least two mutants of the human SIRPα variant 1, and the N-terminals of the two mutants of the human SIRPα variant 1 are linked to the C-terminals of the antibody that specifically binds the AXL antigen or the antigen-binding fragment or the variant thereof, respectively.

For example, as shown in FIG. 1, the first binding domain of the fusion protein (SGAXL47) may comprise an antibody C6G12, the second binding domain thereof may comprise two mutants M91 of the SIRPα variant 1, the sequence of the used linker is shown in SEQ ID NO: 74, the N-terminals of the two M91 are linked to the C-terminals of two heavy chains of C6G12 through the linker respectively. In the fusion protein, M91 is linked to the C-terminal of the heavy chain of C6G12 to get the second polypeptide chain, and the light chain of C6G12 may be named as the first polypeptide chain. The amino acid sequences of the second polypeptide chain and the first polypeptide chain of SGAXL47 are shown in SEQ ID NO: 77 and SEQ ID NO: 32 respectively.

Nucleic Acid Molecules, Vectors and Cells as Well as Preparation Methods

In another aspect, the present application provides one or more isolated nucleic acid molecules, which encode the fusion protein or the immunoconjugate. For example, each nucleic acid molecule of the one or more nucleic acid molecules may encode the whole antibody or the antigen-binding fragment thereof, and may also encode a part thereof (e.g., one or more of HCDR1-3, LCDR1-3, VL, VH, light chains or heavy chains).

The nucleic acid molecules of the present application may be isolated. For example, they can be produced or synthesized by the processes below: (i) amplification in vitro, for example being produced by amplification through polymerase chain reaction (PCR), (ii) being produced by cloning recombination, (iii) being purified, for example fractioned by enzymatic digestion and gel electrophoresis, or, (iv) being synthesized, for example through chemical synthesis. In some embodiments, the isolated nucleic acids are nucleic acid molecules prepared by a recombinant DNA technology.

Recombinant DNA and molecular cloning techniques comprise those described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan and L. W. Enquist, Experiments with Gene Fusions, Cold Spring Harbor Laboratory, Cold Spring Harbor, N.Y. (1984) as well as by Ausubel, F. M. et al, Current Protocols in Molecular Biology, pub. by Greene Publishing Assoc. and Wiley-Interscience (1987). In brief, the nucleic acids can be prepared from genomic DNA fragments, cDNA and RNA, and all of these nucleic acid can be extracted from cells directly or produced by recombination through various amplification methods (including, but not limited to, PCR and RT-PCR).

The direct chemical synthesis of nucleic acids generally involves sequentially adding 3'-capped and 5'-capped nucleotide monomers into the terminal 5'-hydroxyl of the growing nucleotide polymer chain, in which each addition is realized by nucleophilic attacking the terminal 5'-hydroxyl of the growth chain at 3'-position of the added monomers, and the monomers are generally phosphorus derivatives, such as phosphotriester, phosphoramidite, etc. See, for example, Matteuci et al, Tet. Lett. 521:719 (1980); U.S. Pat. No. 4,500,707 to Caruthers et al; and U.S. Pat. Nos. 5,436,327 and 5,700,637 to Southern et al. In another aspect, the present application provides vectors including the isolated polynucleotide of the present application. The vectors may be any linear nucleic acids, plasmids, phagemids, cosmids, RNA vectors, viral vectors, etc. Non-limiting examples of the viral vectors may comprise retroviruses, adenoviruses and adeno-associated viruses. In some embodiments, the vectors are expression vectors, for example, phage display vectors.

In another aspect, the present application provides one or more vectors including the nucleic acid molecules. For example, the vector may comprise the one or more nucleic acid molecules of the present application. Each vector may comprise one or more of the nucleic acid molecules. In addition, the vector may further comprise other genes, such as marker genes which allow to select the vector in appropriate host cells and under appropriate conditions. In addition, the vector may further include expression control elements allowing the correct expression of the coding regions in an appropriate host. Such control elements are well known to those of ordinary skill in the art. For example, they may comprise promoters, ribosome bind sites, enhancers and other control elements for regulating gene transcription or mRNA translation, and the like. In some embodiments, the expression control sequences are tunable elements. The specific structures of the expression control sequences may change depending on the species or the functions of cell types, but generally include 5'-non-transcribed sequences and 5' and 3'-non-translated sequences which participate in the initiation of transcription and translation respectively, e.g., TATA cassettes, capped sequences, CAAT sequences, etc. For example, 5'-non-transcribed expression control sequence may comprise a promoter region, which may comprise a promoter sequence for transcribing and controlling functionally linked nucleic acids. The expression control sequence may further include an enhancer sequence or an upstream activator sequence. In the present application, suitable promoters may comprise, for example, promoters for SP6, T3 and T7 polymerases, human U6RNA promoter, CMV promoter and artificial hybrid promoters (e.g., CMV), in which a certain part of the promoter may be fused with a certain part of the gene promoter of other cell proteins (e.g., human GAPDH, glyceraldehyde-3-phosphate dehydrogenase), and it may comprise or not comprise additional introns. The one or more nucleic acid molecules of the present application can be linked with the expression control elements operably.

The vectors may comprise, for example, plasmids, cosmids, viruses, phages or other vectors commonly used in genetic engineering for example. In some embodiments, the vectors may be expression vectors.

The vectors can also contain one or more selective marker genes, which, after the expression, can confer one or more phenotypic traits that can be used to select or identify host cells carrying the vectors in other ways. Non-limiting examples of suitable selective markers for eukaryocytes comprise dihydrofolate reductase and neomycin resistance.

In another aspect, the present application provides a cell, which comprises the fusion protein, the immunoconjugate, the nucleic acid molecules, or the vectors. The cell may be a host cell. For example, the cell may comprise various cell types as below: prokaryotic cells such as *Escherichia coli* or *Bacillus subtilis*, fungal cells such as yeast cells or *Aspergillus*, insect cells such as S2 *Drosophila* cells or Sf9, or animal cells such as fibroblasts, CHO cells, COS cells, NSO cells, HeLa cells, BHK cells, HEK 293 cells or human cells.

For example, the vectors can be introduced into the host cells stably or transiently through a variety of established technologies. For example, one method involves calcium chloride treatment, in which the vectors are introduced through calcium precipitation. Other salts can also be used following similar methods, for example calcium phosphate. In addition, electroporation (i. e., applying electric current to increase the permeability of cells to nucleic acids) can be used. Other examples of transformation methods comprise microinjection, DEAE dextran-mediated transformation and heat shock in the presence of lithium acetate. Lipid complexes, liposomes and dendrimers can also be used to transfect host cells.

When heterogenous sequences are introduced into the host cells, a variety of methods can be applied to identify host cells into which the vectors have been introduced. One examplary selection method comprises subculturing a single cell to form a single colony, then testing the expression of the desired protein product. Another method requires the selection of host cells containing heterogenous sequences based on the phenotypic traits conferred by the expression of selective marker genes included within the vectors.

For example, the introduction of various heterogenous sequences of the present application into the host cells can be confirmed by the following methods such as PCR, Southern blot or Northern blot. For example, nucleic acids can be prepared from the obtained host cells, and specific target sequences can be amplified by PCR using primers that are specific to the target sequences. The amplified products are subjected to agarose gel electrophoresis, polyacrylamide gel electrophoresis or capillary electrophoresis, then stained with ethidium bromide, SYBR Green solution or the like, or detected for DNA by means of UV detection. Alternatively, nucleic acid probes that are specific to the target sequences can be used in hybridization reactions. The expression of specific gene sequences can be determined by hybridization with PCR or Northern blot or by the reverse transcription detection of corresponding mRNA using immunoassays of antibodies that react with the encoded gene products. Exemplary immunoassays comprise, but not limited to, ELISA, radioimmunoassay and sandwich immunoassay.

In addition, the introduction of various heterogenous sequences of the present application into the host cells can be confirmed by the enzymatic activity of enzymes (e.g., enzymatic markers) that are encoded with heterogenous sequences. Enzymes can be determined by various methods known in the art. Generally, enzymatic activity can be determined by the formation of the products or by the transformation of the substrate of the enzymatic reaction under investigation. The reaction can be performed in vitro or in vivo.

In another aspect, the present application provides a method of preparing the fusion protein, which may comprise culturing the cell under a condition enabling the expression of the fusion protein. For example, suitable culture media, suitable temperature and culture time could be used, all these methods are known to those of ordinary skill in the art.

In some instances, the method may further comprise steps of separating and/or purifying the fusion protein. For example, the fusion protein of the present application can be purified and separated by affinity chromatography using protein G-agarose or protein A-agarose, or by gel electrophoresis and/or high performance liquid chromatography.

Immunoconjugate, Composition and Application

In another aspect, the present application provides a immunoconjugate including the fusion protein. For example, the immunoconjugate may be fusion protein-drug conjugate (ADC), in which the fusion protein of the present application is conjugated with one or more therapeutic agents, and the therapeutic agents comprise, but not limited to, cytotoxic agents, radiotoxic agents (e.g., radioisotopes) and/or immune inhibitors (e.g., any agents that kill cells by means of inhibiting immune responses) and the like. In some embodiments, the therapeutic agents may be those capable of treating tumor-associated diseases or disorders.

The conjugation can be performed by peptide linkers (e.g., cleavable linkers) or through other ways. For example, the linkers may be acid labile linkers, peptidase sensitive linkers, photolabile linker, and the like.

In another aspect, the present application provides a composition including the fusion protein, the immunoconjugate, or the nucleic acid molecules, and optionally, pharmaceutically acceptable excipients.

For example, the pharmaceutically acceptable excipients may comprise buffering agents, antioxidants, preservatives, low molecular weight polypeptides, proteins, hydrophilic polymers, amino acids, sugar, chelating agents, counter ions, metal complexes and/or nonionic surfactants and the like.

In the present application, the composition can be formulated with pharmaceutically acceptable carrier or diluent and any other known auxiliary agents and excipients by conventional technical means in this field, for example following the technology disclosed in Remington: The Science and Practice of Pharmacy, Edition 19, Gennaro ed., Mack Publishing Co., Easton, PA, 1995.

In the present application, the composition can be formulated for oral administration, intravenous administration, intramuscular administration, in situ administration at tumor sites, inhalation, rectal administration, vaginal administration, transdermal administration or administration by subcutaneous reservoir.

For example, the composition can be used to inhibit the tumor growth. For example, the composition of the present application can inhibit or delay the development or progress of diseases, reduce the sizes of tumors (even essentially eliminating tumors), and/or relieve and/or stabilize the status of diseases.

For example, the composition of the present application may be suitable forms for oral administration, such as tablets, capsules, pills, powders, sustained release preparations, solutions, suspensions; or for parenteral injection, such as sterile solutions, suspensions or emulsions; or for local administration as ointment or cream; or for rectal administration as suppositories. The composition may be unit dose forms suitable for single dose at precise dosages.

The composition may further comprise conventional drug carriers or excipients. In addition, the composition may comprise other drugs or agents, carriers, adjuvants, etc.

The composition of the present application may comprise a therapeutically effective amount of the fusion protein. The therapeutically effective amount is a dosage required for preventing and/or treating (at least partially treating) diseases or disorders (e.g., tumors) and/or any complications thereof in subjects suffering from or being at risk of these diseases or disorders. The specific amount/concentration of the dosage may change depending on the administration method and the demand of patients, and can determined, for example, based on the sizes of patients, the viscosity and/or the body weights. For example, a suitable dosage may be about 0.1 mg or 1 mg/kg/day to about 50 mg/kg/day; sometimes, the dosage may be higher. It should be understood that these specific dosages can be adjusted conveniently by the persons skilled in the art (e.g., doctors or pharmacists) based on specific patients, preparations and/or the status of diseases.

In the present application, the terms "treating" or "curing" or "relieving" or "improving" can be used interchangeably in the present application, and refer to those methods capable of obtaining beneficial or desired results (including, but not limited to, therapeutic benefits and/or preventive benefits). In the present application, the therapeutic benefits generally refer to eradicating or reducing the severity of the underlying conditions being treated. In addition, therapeutic benefits are realized by eradicating or reducing the severity of the underlying conditions or reducing the incidence of one or more physical symptoms associated with the underlying conditions so as to observe improvements in the subjects (although the subjects may still suffer from the underlying conditions). With regard to the preventive benefits, the composition can be administered to subjects at risk of developing a specific disease or subjects with one or more physical symptoms of the reported disease, even if the disease may not have been diagnosed.

In another aspect, the present application provides a use of the fusion protein, the immunoconjugate, the nucleic acid molecules, the vectors, the composition, or the cell in the preparation of a medicament, in which the medicament may be used for treating a tumor or an autoimmune disease.

In another aspect, the fusion protein, the immunoconjugate, the nucleic acid molecules, the vectors, the composition or the cell of the present application may be used for treating a tumor or an autoimmune disease.

In another aspect, the present application provides a method of treating a tumor or an autoimmune disease, including administering to the subject the fusion protein, the immunoconjugate, the nucleic acid molecules, the vectors, the composition or the cell of the present application.

In another aspect, the present application provides a method of blocking the interaction between CD47 protein and SIRPα, including administering (for example, administering to a subject in need thereof or cells or biological samples) the fusion protein or the composition of the present application.

In another aspect, the present application provides a method of inhibiting tumor or the growth and/or proliferation of tumor cells, including contacting the fusion protein or the composition of the present application with the tumor or tumor cells. For example, the contact may be in vitro.

In some embodiments, the tumor may comprise a non-solid tumor and a solid tumor.

In some embodiments, the tumor may comprise multiple myeloma, leukemia, Non-Hodgkin lymphoma, Hodgkin's lymphoma, neuroglioma, germinoma, sarcoma, mesothelioma, placentoma, cerebral cancer, bone cancer, skin cancer, nasopharynx cancer, lung cancer, oral cancer, esophagus cancer, gastric cancer, liver cancer, pancreatic cancer, prostate cancer, intestinal cancer, breast cancer, cervical cancer, ovarian cancer and testicular cancer.

In some embodiments, the autoimmune disease may comprise chronic lymphocytic thyroiditis, hyperthyroidism, insulin-dependent diabetes mellitus, myasthenia gravis, chronic ulcerative colitis, pernicious anemia with chronic atrophic gastritis, goodpasture syndrome, pemphigus vulgaris, pemphigoid, primary biliary cirrhosis, multiple sclerosis, acute idiopathic polyneuritis, systemic lupus erythematosus, rheumatoid arthritis, scleroderma and polyarteritis nodosa.

In another aspect, the present application provides the fusion protein, the immunoconjugate, the nucleic acid molecules, the vectors, the composition, or the cell, which can be used for treating a tumor or an autoimmune disease.

In another aspect, the present application provides a method of blocking the interaction between CD47 protein and SIRPα, including administering to a subject in need thereof an effective amount of the fusion protein, the immunoconjugate, the nucleic acid molecules, the vectors, the composition, or the cell.

In the present application, the term "subject" generally refers to human or non-human animals, including, but not limited to, cat, dog, horse, pig, cow, sheep, goat, rabbit, mouse, rat or monkey.

In another aspect, the present application provides a method capable of inhibiting tumors or the growth and/or proliferation of tumor cells, which may comprise administering to a subject in need thereof an effective amount of the fusion protein, the immunoconjugate, the nucleic acid molecules, the vectors, the composition, or the cell.

Without intending to be bound by any theory, the embodiments below are only for interpreting the fusion protein, the preparation method and the use of the present application, rather than limiting the inventive scope of the present application.

EMBODIMENTS

Embodiment 1. Effect of Different Linker Selections on the Activity 1.1 Preparation of a Fusion Protein Using Different Linkers Referring to the fusion protein structure as shown in FIG. 1, taking the anti-CD38 humanized antibody SG003 and the mutant M91 (SEQ ID: NO 62) of the SIRPα variant 1 for example, different linkers are used from N terminal to C terminal to successively link SG003, the linker and two M91, in which the N-terminals of the two M91 are linked to the C-terminal of the heavy chain of SG003 respectively, so as to investigate the effect of different linkers on the biological activity of the fusion protein.

The amino acid sequences of LCDR1-3 of the antibody SG003 are shown in SEQ ID NO: 1, SEQ ID NO: 2 and SEQ ID NO: 3, respectively; the amino acid sequence of VL is shown in SEQ ID NO: 7; the nucleotide sequence encoding VL is shown in SEQ ID NO: 9; the amino acid sequences of HCDR1-3 of the antibody SG003 are shown in SEQ ID NO: 4, SEQ ID NO: 5 and SEQ ID NO: 6, respectively; the amino acid sequence of VH is shown in SEQ ID NO: 8; the nucleotide sequence encoding VH is shown in SEQ ID NO: 10. The amino acid sequence of the light chain of the antibody SG003 is shown in SEQ ID NO: 11; and the nucleotide sequence encoding it is shown in SEQ ID NO: 12. The amino acid sequence of the heavy chain of the antibody SG003 is shown in SEQ ID NO: 13; and the nucleotide sequence encoding it is shown in SEQ ID NO: 14.

Linker 1 (SEQ ID: NO 73) is selected, and the constructed fusion protein is named as SG3847L1. The SG3847L1 is composed of a first polypeptide chain and a second polypeptide chain. The first polypeptide chain is the light chain of SG003, the amino acid sequence of which is shown in SEQ ID NO: 11; the second polypeptide chain is the polypeptide chain formed from the connection between the heavy chain of SG003 and M91 through the linker 1, the amino acid sequence of which is shown in SEQ ID NO: 75.

Linker 2 (SEQ ID: NO 74) is selected, and the constructed fusion protein is named as SG3847L2. The SG3847L2 is composed of a first polypeptide chain and a second polypeptide chain. The first polypeptide chain is the light chain of SG003, the amino acid sequence of which is shown in SEQ ID NO: 11; the second polypeptide chain is the polypeptide chain formed from the connection between the heavy chain of SG003 and M91 through the linker 2, the amino acid sequence of which is shown in SEQ ID NO: 76.

1.2 Analysis on the Activity of Binding Two Antigens Respectively (1) With SG003 as the control, the binding activity between the fusion protein and CD38 was evaluated by ELISA.

Target antigen CD38-His (1 μg/ml) was coated on ELISA bars, overnight at 4° C.; after washing with PBST, 10% of fetal calf serum was added and blocked at 37° C. for 1 hour; different concentrations of SG003 antibody, SG3847L1 or SG3847L2 fusion protein were added and reacted at 37° C. for 1 hour; after washing with PBST, horseradish peroxidase-labeled goat anti-human IgG secondary antibodies (Goat Anti human IgG HRP, Thermo Fisher Scientific) were added and reacted at 37° C. for 30 minutes, and washed with PBST for 5 times; each well was added with 100 μl TMB (eBioscience), placed in dark at room temperature (20±5° C.) for 1-2 min; then each well was added with 100 μl 2N $H_2SO_4$ stop solution to terminate the reaction of the substrate, OD values were read at 450 nm on the microplate reader, and the capacity of the fusion protein to bind the target antigen CD38 was analyzed.

Figure 2:
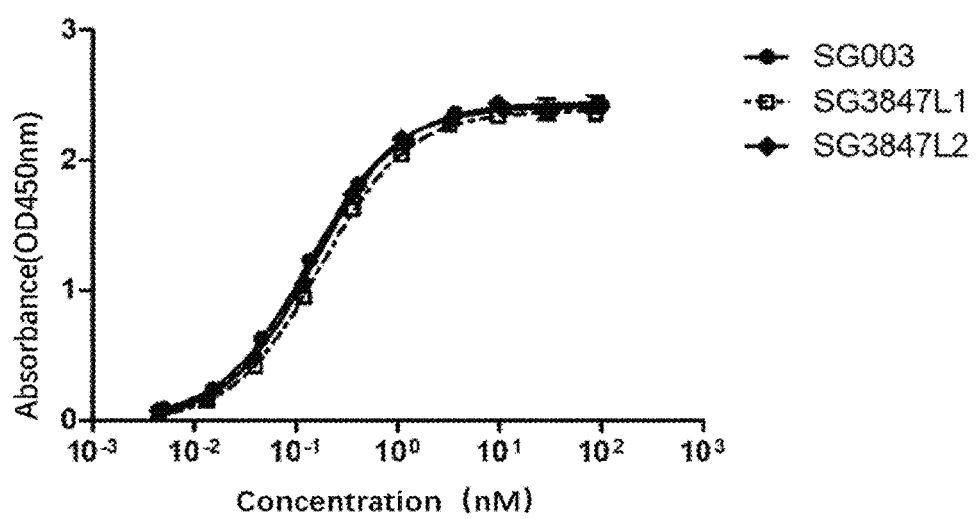
FIGS. 2 and 3 show the biological activity of the fusion protein according to the present application.

As shown in FIG. 2, compared to SG003 antibody, the binding capacity of SG3847L1, SG3847L2 with the target antigen CD38 were similar, EC50 values of SG3847L1, SG3847L2 and SG003 were 0.175 nM, 0.149 nM and 0.133 nM, respectively.

(2) With SS002M91 as the control, the binding activity between the fusion protein and CD47 was evaluated by ELISA.

M91 was fused with IgG1-FC (the sequence is shown in SEQ ID NO: 71) to get SS002M91, the amino acid sequence of which is shown in SEQ ID NO: 72.

Target antigen CD47-His (1 μg/ml) was coated on ELISA bars, overnight at 4° C.; after washing with PBST, 10% of fetal calf serum was added and blocked at 37° C. for 1 hour; different concentrations of SS002M91, SG3847L1 or SG3847L2 was added and reacted at 37° C. for 1 hour; after washing with PBST, horseradish peroxidase-labeled goat anti-human IgG secondary antibodies (Goat Anti human IgG HRP, Thermo Fisher Scientific) were added and reacted at 37° C. for 30 minutes, and washed with PBST for 5 times; each well was added with 100 TMB (eBioscience), placed in dark at room temperature (20±5° C.) for 1-2 min; then each well was added with 100 μl 2N $H_2SO_4$ stop solution to terminate the reaction of the substrate, OD values were read at 450 nm on the microplate reader, and the capacity of the fusion protein to bind the target antigen CD47 was analyzed.

Figure 3:
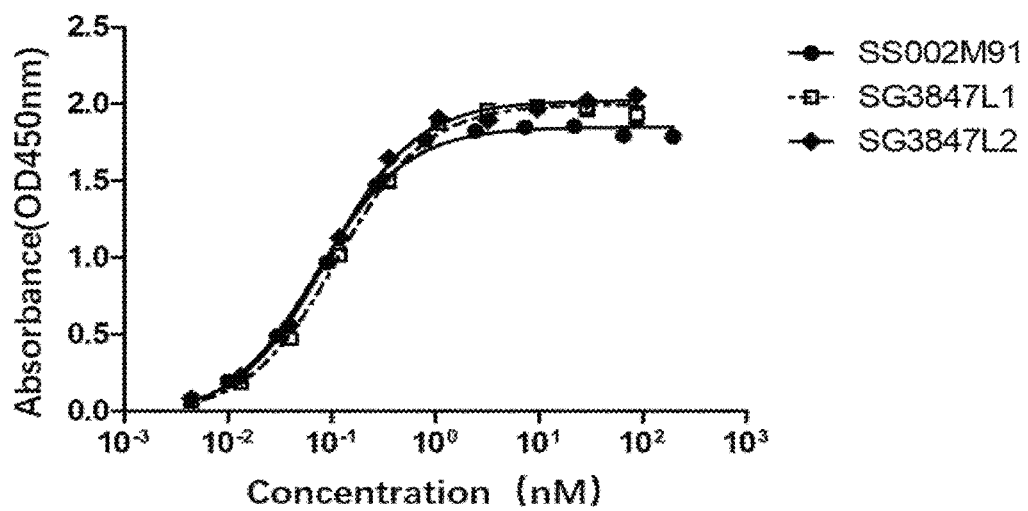

As shown in FIG. 3, compared to SS002M91, the binding capacity of SG3847L1, SG3847L2 to the target antigen CD47 were similar, EC50 values of SG3847L1, SG3847L2 and SS002M91 were 0.114 nM, 0.091 nM and 0.072 nM, respectively.

(3) With SG003 and SS002M91 respectively as the control, the binding activity between the fusion protein and CD38 and CD47 antigens was evaluated by ELISA respectively.

CHO-S cell lines which have been engineered to express human CD38 or human CD47 were used to evaluate the capacity of the fusion protein to bind antigens on the cell surface. Cells in logarithmic growth period were collected, adjusted to a cell density of $5 \times 10^6$ cells/mL, and pre-cooled on ice. SG003, SS002M91, a negative control antibody (IgG1), SG3847L1 or SG3847L2 was diluted to different concentrations with pre-cooled saline containing 2% FBS. 100 µl cells were taken and added into an equal volume of the above diluted antibody or fusion protein, and reacted in dark at 4° C. for 30 min. At the end of the reaction, the cells were washed twice. The cells were resuspended with 100 µL of the diluted PE-Goat anti-human IgG Fc Secondary Antibody (eBioscience), and reacted in dark at 4° C. for 30 min. At the end of the reaction, the cells were washed twice. The cells were resuspended with 400 µl of 1% paraformaldehyde. The binding capacity between the fusion protein and CD38 or CD47 on the cell surface was analyzed on a flow cytometer (BD Calibur).

Figure 4:
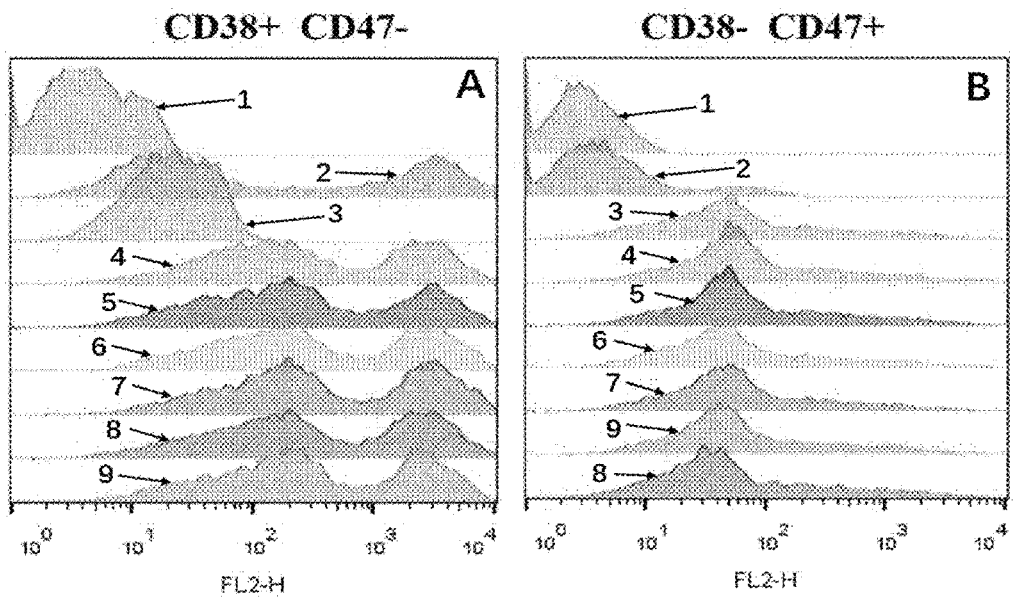
FIGS. 4A and 4B show the biological activity of the fusion protein according to the present application.

As shown in FIGS. 4A and 4B, "1", "2", "3", "4", "5", "6", "7", "8" and "9" refer to 20 µg ml$^{-1}$ IgG1, 20 µg ml$^{-1}$ SG003, 20 µg ml$^{-1}$ SS002M91, 20 µg ml$^{-1}$ SG3847L1, 10 µg ml$^{-1}$ SG3847L1, 5 µg ml$^{-1}$ SG3847L1, 20 µg ml$^{-1}$ SG3847L2, 10 µg ml$^{-1}$ SG3847L2 and 5 µg ml$^{-1}$ SG3847L2, respectively. The results showed that, the fusion proteins SG3847L1 and SG3847L2 could specifically recognize CD38 or CD47 antigen expressed on the cell surface.

Figure 5:
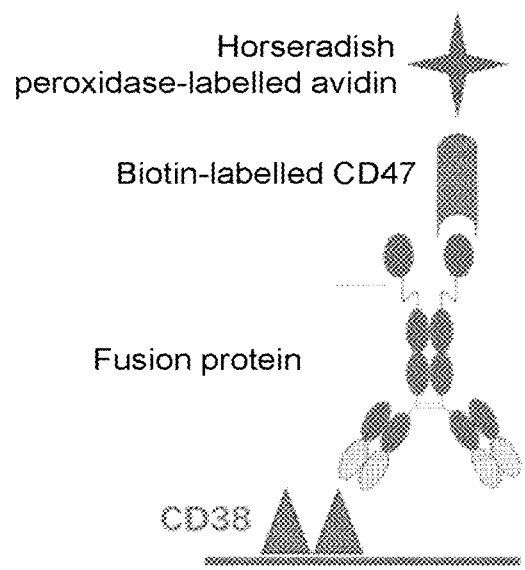
FIG. 5 shows a diagram showing the principle of the method for detecting the interaction between the fusion protein of the present application and CD38 and CD47.

1.3 Analysis on the Activity of Simultaneously Binding Two Antigens (1) Referring to the principle of FIG. 5, with the anti-CD38 humanized antibody SG003 as the control, the biological activities of the fusion proteins SG3847L1 and SG3847L2 to simultaneously bind two antigens CD38 and CD47 were analyzed by ELISA.

Target antigen CD38-His (1 µg/ml) was coated on ELISA bars, overnight at 4° C.; after washing with PBST, 10% of fetal calf serum was added and blocked at 37° C. for 1 hour; different concentrations of SG003 antibody, SG3847L1 or SG3847L2 fusion protein were added and reacted at 37° C. for 1 hour; after washing with PBST, biotin-labeled CD47 (Biotin-Fc-CD47) was added and reacted at 37° C. for 30 minutes, and washed with PBST for 5 times; horseradish peroxidase-labeled avidin (Streptavidin-HRP, Jiaxuan Bio.) was added and reacted at 37° C. for 30 minutes, and washed with PBST for 5 times; each well was added with 100 µl TMB (eBioscience), placed in dark at room temperature (20±5° C.) for 1-2 min; then each well was added with 100 µl 2N H$_2$SO$_4$ stop solution to terminate the reaction of the substrate, OD values were read at 450 nm on the microplate reader, and the capacities of the fusion proteins to simultaneously bind the target antigens CD38 and CD 47 were analyzed.

Figure 6:
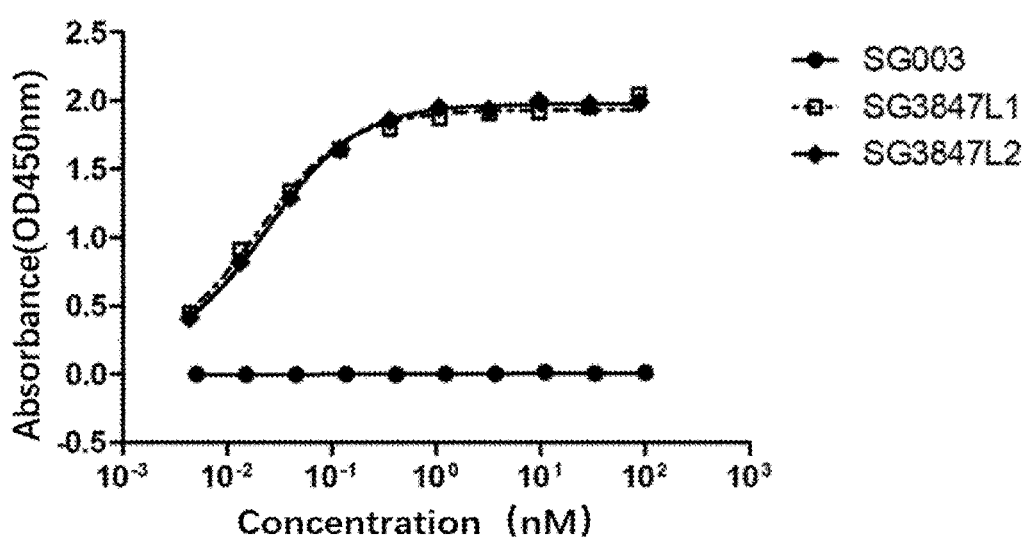
FIG. 6 shows the biological activity of the fusion protein according to the present application.

As shown in FIG. 6, compared to SG003 antibody, the fusion proteins SG3847L1, SG3847L2 could simultaneously bind the target antigens CD38 and CD47, and EC50 values of SG3847L1 and SG3847L2 were 0.020 nM and 0.024 nM, respectively.

Figure 7:
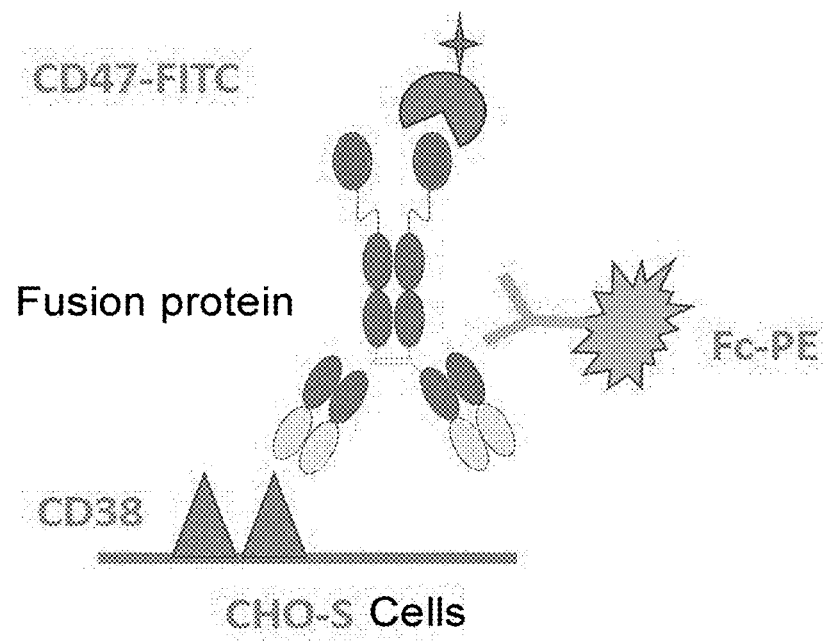
FIG. 7 shows a diagram showing the principle of the method for detecting the interaction between the fusion protein of the present application and CD38 and CD47.

(2) Referring to the principle of FIG. 7, with SG003 and SS002M91 as the control, the biological activities of the fusion proteins SG3847L1 and SG3847L2 to simultaneously bind two antigens CD38 and CD47 on the cell surface were evaluated.

CHO-S cell lines which have been engineered to express human CD38 were used to evaluate the capacity of the fusion proteins to simultaneously bind two antigens on the cell surface. Cells in logarithmic growth period were collected, adjusted to a cell density of $5 \times 10^6$ cells/mL, and pre-cooled on ice. SG003 antibody, SS002M91 fusion protein, a negative control antibody (IgG1), SG3847L1 or SG3847L2 was diluted with pre-cooled saline containing 2% FBS. 100 µl cells were taken and added into an equal volume of the above diluted antibody or fusion proteins and CD47-FITC (Jiaxuan Bio.), and reacted in dark at 4° C. for 30 min. At the end of the reaction, the cells were washed twice. The cells were resuspended with 100 µL of the diluted PE-Goat anti-human IgG Fc Secondary Antibody (eBioscience), that is Fc-PE, and reacted in dark at 4° C. for 30 min. At the end of the reaction, the cells were washed twice. The cells were resuspended with 400 µl of 1% paraformaldehyde. The capacities of the fusion proteins to simultaneously bind CD38 and CD47 on the cell surface were analyzed on a flow cytometer (BD Calibur).

Figure 8:
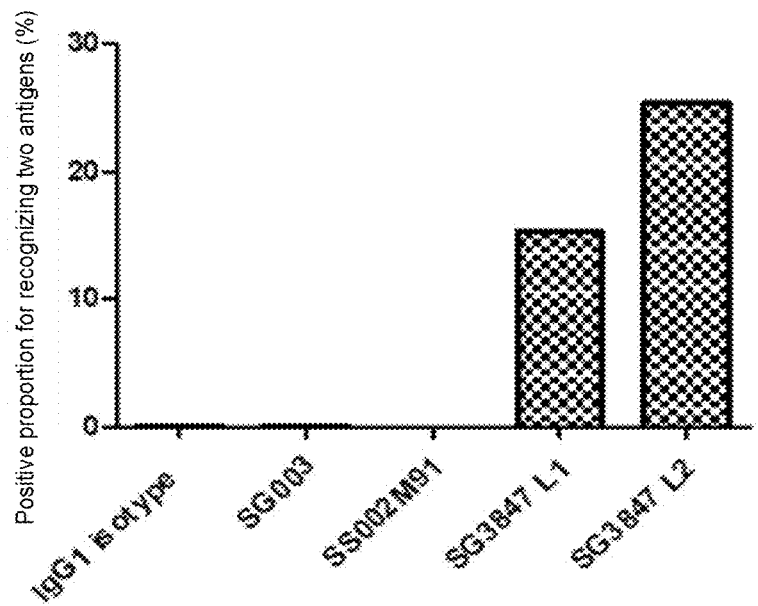
FIGS. 8 and 9 show the biological activity of the fusion protein according to the present application.

As shown in FIG. 8, the fusion proteins SG3847L1 and SG3847L2 could simultaneously recognize CD38 and CD47 antigens on the cell surface, and SG3847L2 had a higher capacity of simultaneously recognizing the two antigens.

1.4 Analysis on ADCC Activity of Killing CD38 Positive Cells

First, the target cells (Raji cells) needed for the experiment were adjusted to a density of $2 \times 10^5$ cells/mL, resuspended in an ADCC buffer solution (MEM culture solution without phenol red+1% FBS), and added into a 96-well plate (50 µL/well). 100 µL different concentrations of SG003, SG3847L1 and SG3847L2 were then added into each well, mixed uniformly and then incubated in an incubator at 37° C. and 5% CO$_2$ for 30 min. Then, effector cells NK92MI-CD16a (Huabo Bio.) needed for the experiment were adjusted to a density of $1.2 \times 10^6$ cells/mL, and added into the wells containing target cells, so that the ratio of target cells:effector cells=1:6. After mixed uniformly, they were incubated in an incubator at 37° C. and 5% CO$_2$ for 6 h. Then 100 µL/well of stock solution was removed from the 96-well plate, and 100 µL/well of LDH reaction mixture from LDH detection kit (Cytotoxicity Detection Kit, Roche) was added and reacted at 37° C. for 10 min. 50 µL/well of stop solution was additionally added and mixed gently. OD at 492 nm was determined on a microplate reader, and OD at 650 nm was also determined as the background value. The following control groups were set at the same time in the experiment, in which the control 1 was ADCC buffer solution, the control 2 was target cells+ADCC buffer solution, the control 3 was target cells+lysate+ADCC buffer solution, the control 4 was target cells+ effector cells+ADCC buffer solution. Specific kill rate %=((experimental group−control 4)/(control 3−control 2))×100%. Data analysis was performed on the dose-effect curve using GraphPad Prism Version 5.

Figure 9:
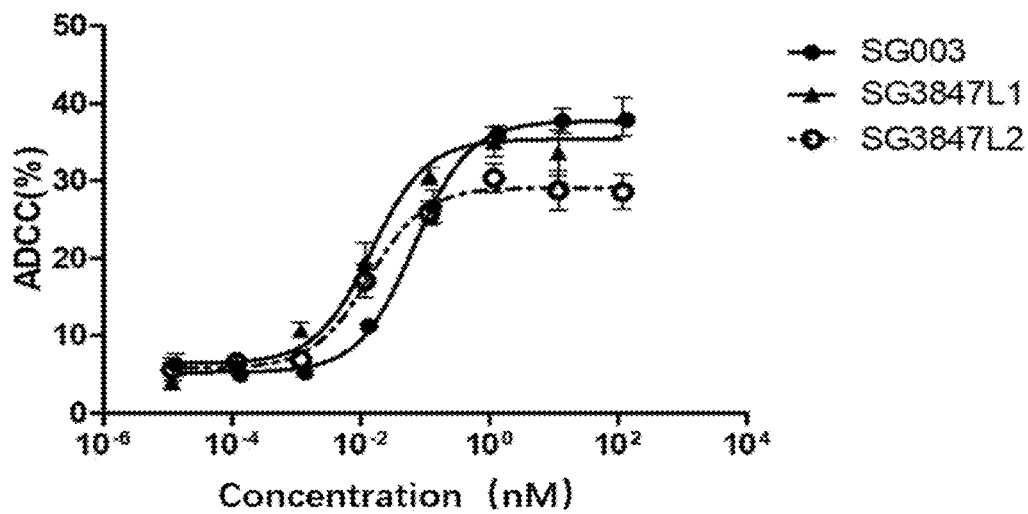

As shown in FIG. 9, when Raji target cells and NK92MI-CD16a effector cells were used for detection, the fusion proteins SG3847L1 and SG3847L2 showed better ADCC effect. EC50 values of SG003, SG3847L1 and SG3847L2 were 0.067 nM, 0.014 nM and 0.013 nM, respectively.

1.5 Analysis on the Activity of Blocking the Interaction Between CD47 Protein and SIRPα

With SS002M91 as the control, the biological activities of the fusion proteins SG3847L1 and SG3847L2 to block the interaction between CD47 protein and SIRPα were evaluated.

SIRPα-His was coated on the assay plate at 1 μg/ml overnight at 4° C.; after washing with PBST, 10% of fetal calf serum was added and blocked at 37° C. for 1 hour; SS002M91, SG3847L1 or SG3847L2 was gradiently diluted respectively with 10% of fetal bovine blood, and Biotin-Fc-CD47 was added into the samples until a final concentration of 2 μg/ml, pre-incubated at 37° C. for 30 min, as the primary antibody; after the assay plate was washed with PBST, the primary antibody was added and incubated at 37° C. for 1 hour; after washing with PBST for 5 times, horseradish peroxidase-labeled avidin (Streptavidin-HRP, Jiaxuan Bio.) was added and incubated at 37° C. for 30 minutes; after washing with PBST for 5 times, each well was added with 100 μl TMB (eBioscience), placed in dark at room temperature (20±5° C.) for 1-5 min; then each well was added with 100 μl 2N $H_2SO_4$ stop solution to terminate the reaction of the substrate, OD values were read at 450 nm on the microplate reader, and the blocking effects of SS002M91, SG3847L1, SG3847L2 on CD47/SIRPα were analyzed.

Figure 10:
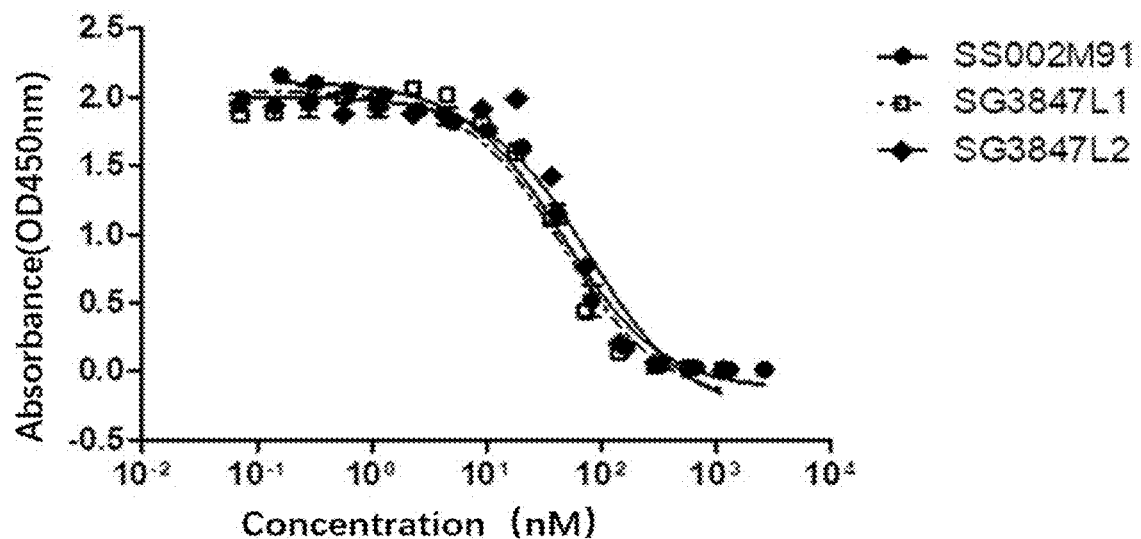
FIG. 10 shows that the fusion protein of the present application blocks the interaction between CD47 protein and SIRPα.

As can be seen from FIG. 10, similar to SS002M91, SG3847L1 and SG3847L2 could competitively block the binding between CD47 and its ligand SIRPα. IC50 value of SG3847L1 is 46.8 nM, IC50 value of SG3847L2 is 78.8 nM, and IC50 value of SS002M91 is 45.7 nM.

Embodiment 2 Employing Combinations of Different Target Antibodies and a Mutant of a Human SIRPα Variant 1

Referring to the structure of the fusion protein in FIG. 1 and the results of Embodiment 1, taking anti-AXL antibody (C6G12) and anti-Trop2 (SG701) antibody for example, the effects of different target antibodies on the biological activity of the fusion protein were investigated, in which the used linker was the linker 2.

The amino acid sequences of LCDR1-3 of the antibody C6G12 are shown in SEQ ID NO: 22, SEQ ID NO: 23 and SEQ ID NO: 24, respectively; the amino acid sequence of VL is shown in SEQ ID NO: 28; the amino acid sequences of HCDR1-3 are shown in SEQ ID NO: 25, SEQ ID NO: 26 and SEQ ID NO: 27, respectively; the amino acid sequence of VH is shown in SEQ ID NO: 29; the amino acid sequence of the light chain is shown in SEQ ID NO: 32; and the amino acid sequence of the heavy chain is shown in SEQ ID NO: 34.

The amino acid sequences of LCDR1-3 of the antibody SG701 are shown in SEQ ID NO: 37, SEQ ID NO: 38 and SEQ ID NO: 39, respectively; the amino acid sequence of VL is shown in SEQ ID NO: 42; the amino acid sequences of HCDR1-3 are shown in SEQ ID NO: 39, SEQ ID NO: 40 and SEQ ID NO: 41, respectively; the amino acid sequence of VH is shown in SEQ ID NO: 43; the amino acid sequence of the light chain is shown in SEQ ID NO: 46; the amino acid sequence of the heavy chain is shown in SEQ ID NO: 48.

A fusion protein was prepared from an anti-AXL antibody (C6G12), a mutant M91 of SIRPα variant 1 and a linker 2 (SEQ ID: NO 74). C6G12, a linker and two M91 were successively linked from N-terminal to C-terminal, wherein the N-terminals of the two M91 were linked to the C-terminal of the heavy chain of C6G12 respectively, and the resulting fusion protein was named as SGAXL47. The amino acid sequences of the second polypeptide chain and the first polypeptide chain of SGAXL47 are shown in SEQ ID NO: 77 and SEQ ID NO: 32, respectively.

A fusion protein was prepared from an anti-Trop antibody (SG701), a mutant M91 of SIRPα variant 1 and a linker 2 (SEQ ID: NO 74). SG701, a linker and two M91 were successively linked from N-terminal to C-terminal, wherein the N-terminals of the two M91 were linked to the C-terminal of the heavy chain of SG701 respectively, and the resulting fusion protein was named as SGTrop247. The amino acid sequences of the second polypeptide chain and the first polypeptide chain of SGTrop247 are shown in SEQ ID NO: 78 and SEQ ID NO: 46, respectively.

By using conventional molecular biological techniques, the expression genes of SGAXL47 and SGTrop247 fusion proteins were constructed into eukaryotic expression vectors. After the CHO-S cells were transfected, the supernatant was harvested, and then affinity purification was performed through Protein A to get the target protein, the biological activity of which was evaluated properly.

2.1 Analysis on the Activity of Binding Two Antigens (1) With humanized antibodies against different antigens as the control, the binding activity between the fusion protein and related antigens was evaluated by ELISA.

Target antigens were coated on ELISA bars, overnight at 4° C.; after washing with PBST, 10% of fetal calf serum was added and blocked at 37° C. for 1 hour; different concentrations of antibodies or fusion proteins were added and reacted at 37° C. for 1 hour; after washing with PB ST, horseradish peroxidase-labeled goat anti-human IgG secondary antibodies (Goat Anti human IgG HRP, Thermo Fisher Scientific) were added and reacted at 37° C. for 30 minutes, and washed with PBST for 5 times; each well was added with 100 μl TMB (eBioscience), placed in dark at room temperature (20±5° C.) for 1-2 min; then each well was added with 100 μl 2N $H_2SO_4$ stop solution to terminate the reaction of the substrate, OD values were read at 450 nm on the microplate reader, and the capacity of the fusion protein to bind the related target antigens was analyzed.

Figure 11A:
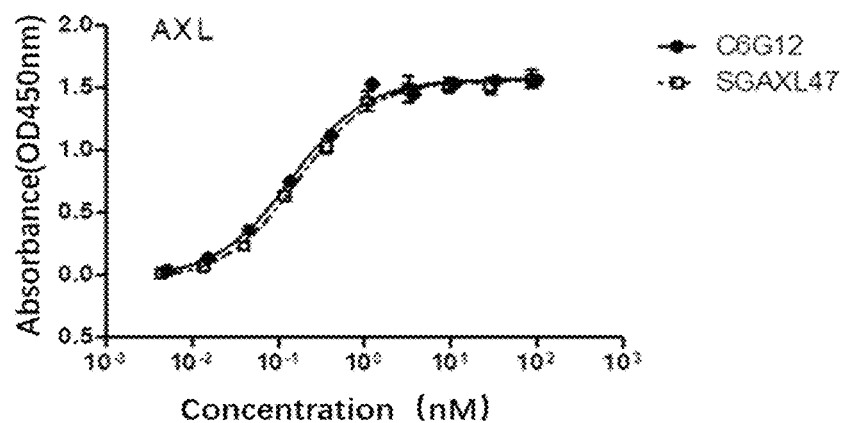
FIGS. 11A-11B, FIGS. 12A-12B and FIGS. 13A-13B show the binding activity between the fusion protein of the present application and corresponding antigens.
Figure 11B:
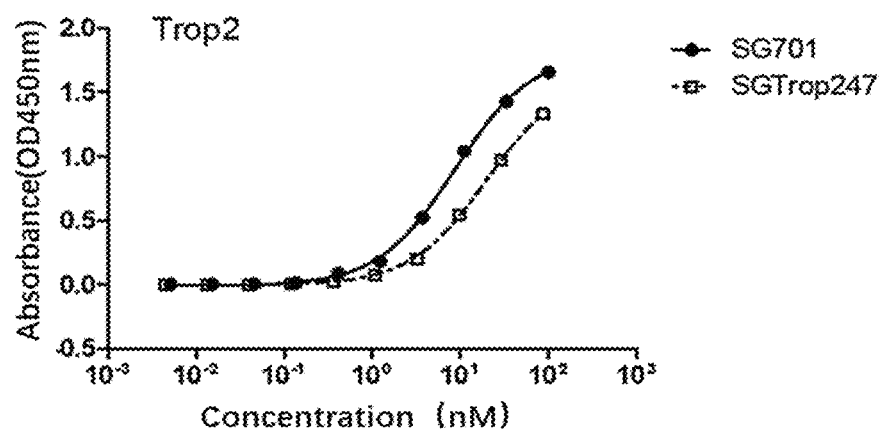

As shown in FIG. 11A, the binding capacity of SGAXL47 to the AXL antigen is close to that of C6G12. As shown in FIG. 11B, the binding capacity of SGTrop247 to the Trop2 antigen is close to that of SG701. It demonstrated that antibodies with different target sites used in the fusion protein did not affect the binding capacity of the antibody to the Trop2 antigen.

(2) With SS002M91 as the control, the binding activity between the fusion protein and CD47 was evaluated by ELISA.

Target antigen CD47 was coated on ELISA bars, overnight at 4° C.; after washing with PBST, 10% of fetal calf serum was added and blocked at 37° C. for 1 hour; different concentrations of the fusion protein SS002M91 or the fusion protein was added and reacted at 37° C. for 1 hour; after washing with PBST, horseradish peroxidase-labeled goat anti-human IgG secondary antibodies (Goat Anti human IgG HRP, Thermo Fisher Scientific) were added and reacted at 37° C. for 30 minutes, and washed with PBST for 5 times; each well was added with 100 μl TMB (eBioscience), placed in dark at room temperature (20±5° C.) for 1-2 min;

then each well was added with 100 μl 2N $H_2SO_4$ stop solution to terminate the reaction of the substrate, OD values were read at 450 nm on the microplate reader, and the capacity of the fusion protein to bind CD47 was analyzed.

Figure 12A:
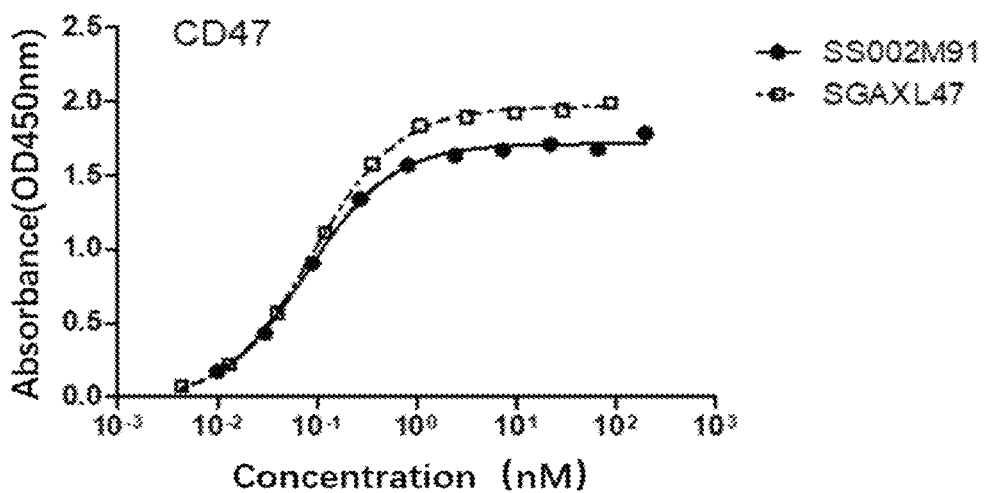
Figure 12B:
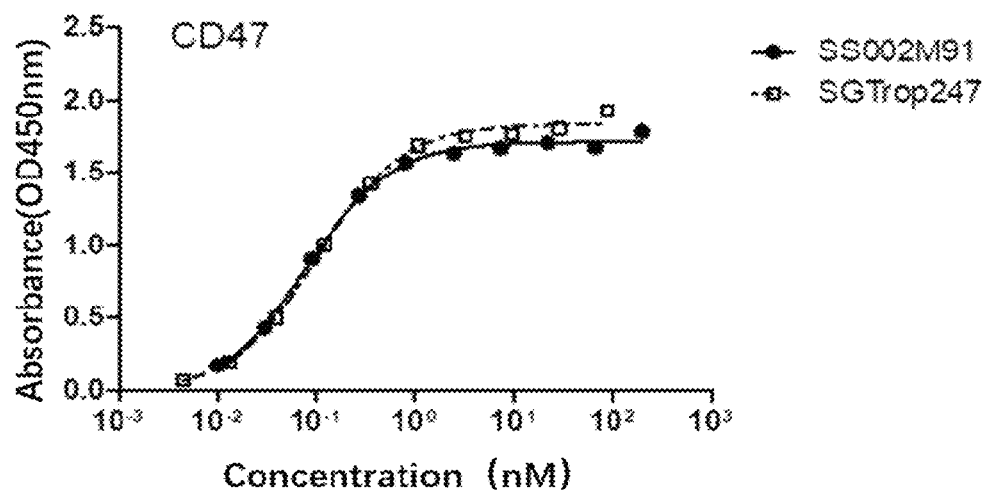

As shown in FIG. 12A, the binding capacity of SGAXL47 to the CD47 antigen is close to that of SS002M91. As shown in FIG. 12B, the binding capacity of SGTrop247 to the CD47 antigen is close to that of SS002M91. It demonstrated that antibodies with different target sites used in the fusion protein did not affect the binding capacity of the antibody to the CD47 antigen.

2.2. Analysis on the Activity of Simultaneously Binding Two Antigens

With humanized antibodies against different antigens as the control, the biological activity of the fusion protein to simultaneously bind two antigens was analyzed by ELISA.

Target antigens were coated on ELISA bars, overnight at 4° C.; after washing with PBST, 10% of fetal calf serum was added and blocked at 37° C. for 1 hour; different concentrations of antibodies or fusion proteins were added and reacted at 37° C. for 1 hour; after washing with PBST, biotin-labeled CD47 (Biotin-Fc-CD47) was added and reacted at 37° C. for 30 minutes, and washed with PBST for 5 times; horseradish peroxidase-labeled avidin (Streptavidin-HRP, Jiaxuan Bio.) was added and reacted at 37° C. for 30 minutes, and washed with PBST for 5 times; each well was added with 100 μl TMB (eBioscience), placed in dark at room temperature (20±5° C.) for 1-2 min; then each well was added with 100 μl 2N $H_2SO_4$ stop solution to terminate the reaction of the substrate, OD values were read at 450 nm on the microplate reader, and the capacities of the fusion proteins to simultaneously bind the related antigen and CD 47 were analyzed.

Figure 13A:
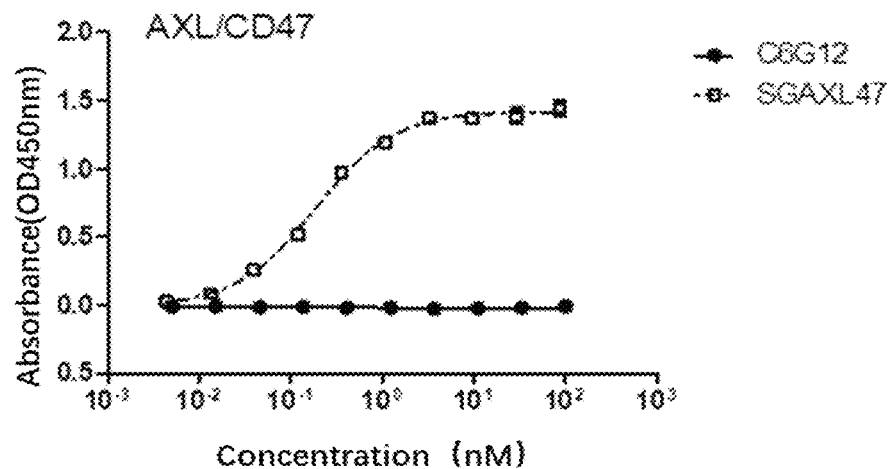
Figure 13B:
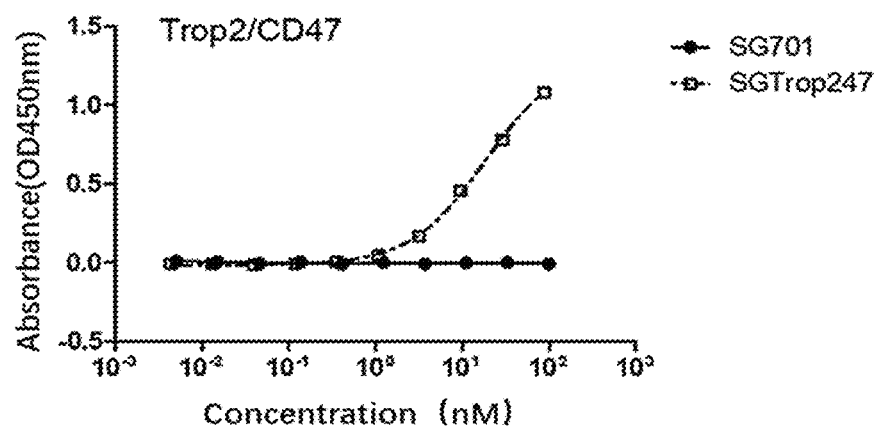

FIG. 13A showed the binding profiles of SGAXL47 and C6G12 to the double antigens AXL and CD47 respectively; FIG. 13B showed the binding profiles of SGTrop247 and SS002M91 to the double antigens Trop2 and CD47 respectively. The results of FIG. 13 showed that different antibodies replaced in the fusion protein did not affect its simultaneous binding with the double antigens.

Embodiment 3 Fusion Protein Inhibits the Tumor Activity In Vivo

CB17 SCID mice were inoculated with Raji-Luc cells by tail intravenous injection to establish tumor models, and the inhibitory effect of the fusion protein SG3847L1 on the tumor activity was evaluated.

Female CB17 SCID mice of 5-8 weeks (purchased from Beijing Biocytogen Co., Ltd) were chosen for experiment. Raji-Luc cells were stable cell lines obtained from introducing luciferase reporter gene on the basis of Raji cells by Beijing Biocytogen Co., Ltd. Raji-Luc cells were resuscitated and cultured to the desired number, then the cells in logarithmic growth period were collected and suspended to a concentration of $2.5 \times 10^7$/mL. CB17 SCID mice were inoculated by tail intravenous injection at a dose of 0.2 mL per mouse. On days 0 and 7 after inoculation, an imager for small animals was used to observe the growth profile and weight of the tumor. On day 7, 30 mice with modest tumor imaging signals were chosen and randomly assigned into 5 groups, with 6 mice per group. Then the animals were administered with drugs once, which are divided into a saline control group, an experimental group (SG003, 100 ug/kg), an experimental group (SS002M91, 50 ug/kg), a combined-dosing group (SG003+SS002M91, 100 ug/kg+50 ug/kg), an experimental group (SG3847L1, 120 ug/kg). At the same time, the mice weight and the tumor growth profiles were observed.

Figure 14:
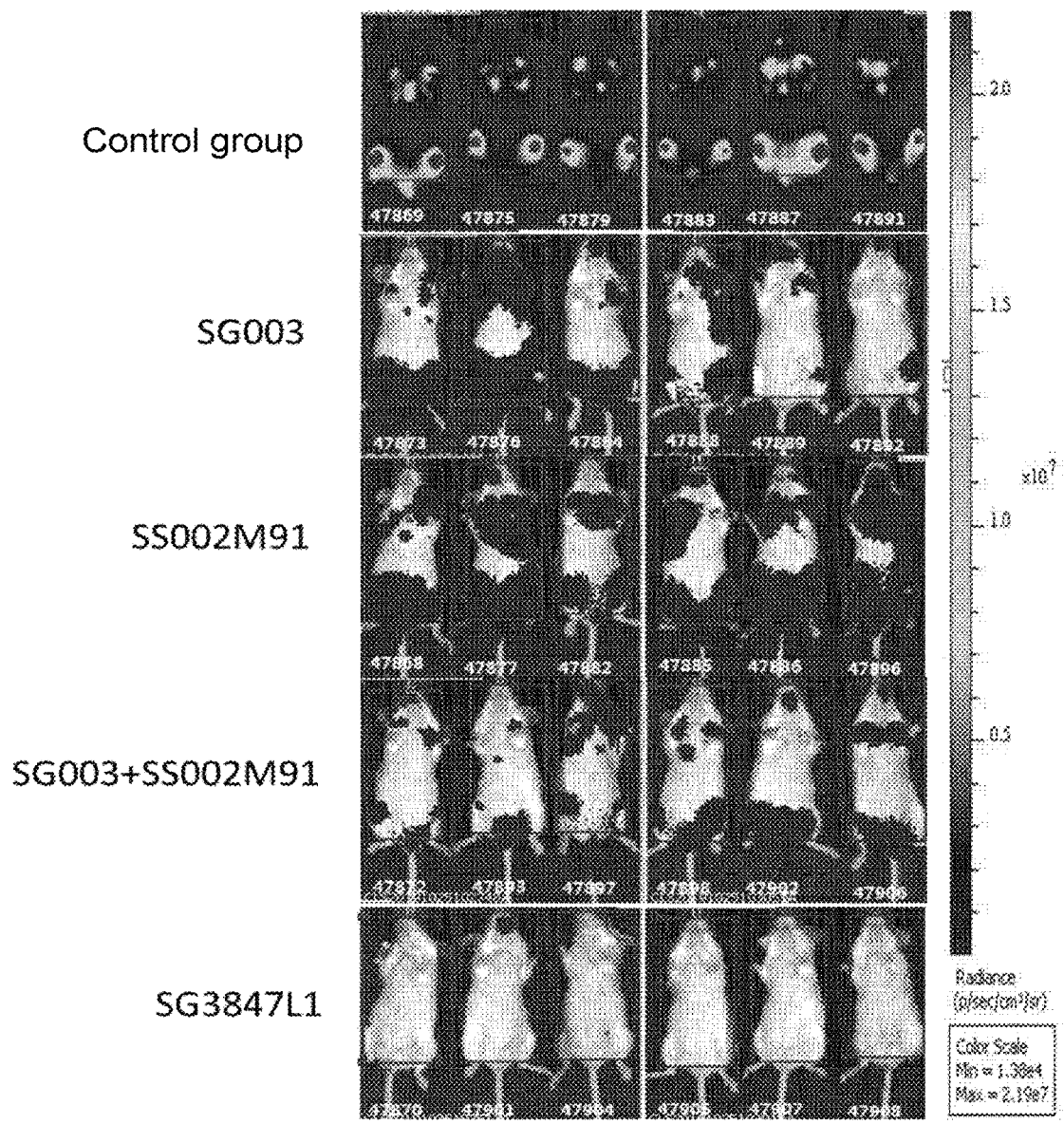
FIG. 14 shows the tumor imaging results of mice in different treatment groups.
Figure 15:
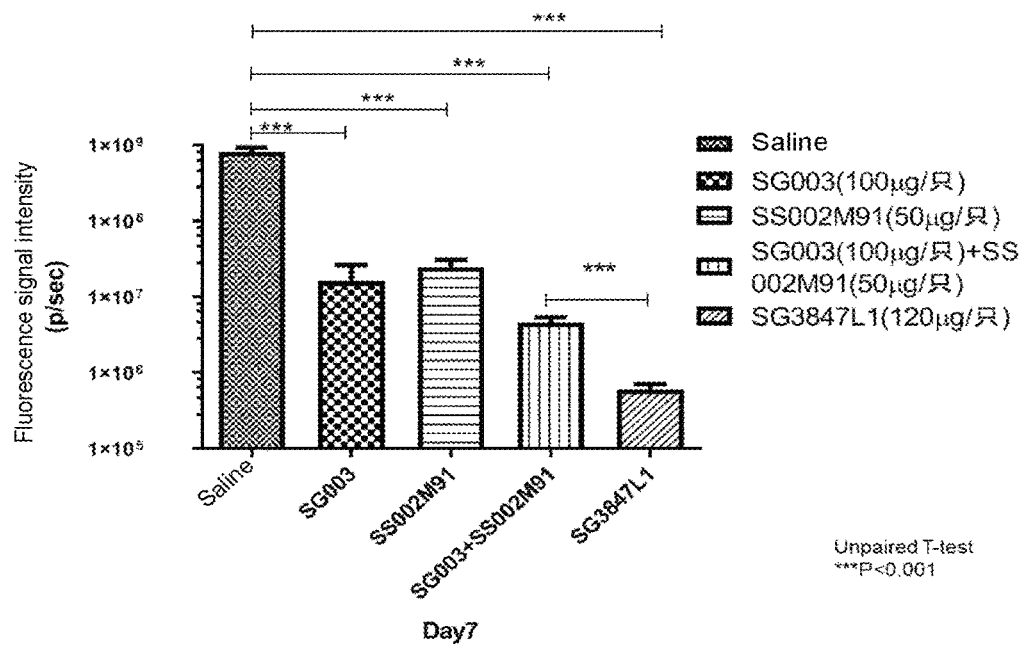
FIG. 15 shows the mean tumor fluorescence intensity of mice in different treatment groups.

The results showed that, the SG003 antibody, the SS002M91 fusion protein and the SG3847L1 fusion protein were all tolerated by experimental animals. Compared with the saline control group, there were obvious inhibitory effects on tumor growth in various groups of dosed animals (see FIG. 14). It can be seen from FIG. 15 that, on day 7 after administration, the average fluorescence intensities of the SG003 antibody treatment group, the SS002M91 fusion protein treatment group, the SG003 antibody and SS002M91 fusion protein combination treatment group and the SG3847L1 fusion protein treatment group were 1.60E+07 (standard error: 1.02E+07), 2.42E+07 (standard error: 6.70E+06), 4.61E+06 (standard error: 7.57E+05), 5.97E+05 (standard error: 1.10E+05), respectively, all of which were significantly lower than the average fluorescence intensity of the control group, that is 8.04E+08 (standard error: 1.15E+08). In addition, the inhibitory effect of the SG3847L1 fusion protein treatment group on the tumor growth is significantly superior to that of the SG003 antibody and SS002M91 fusion protein combination group.

Figure 16:
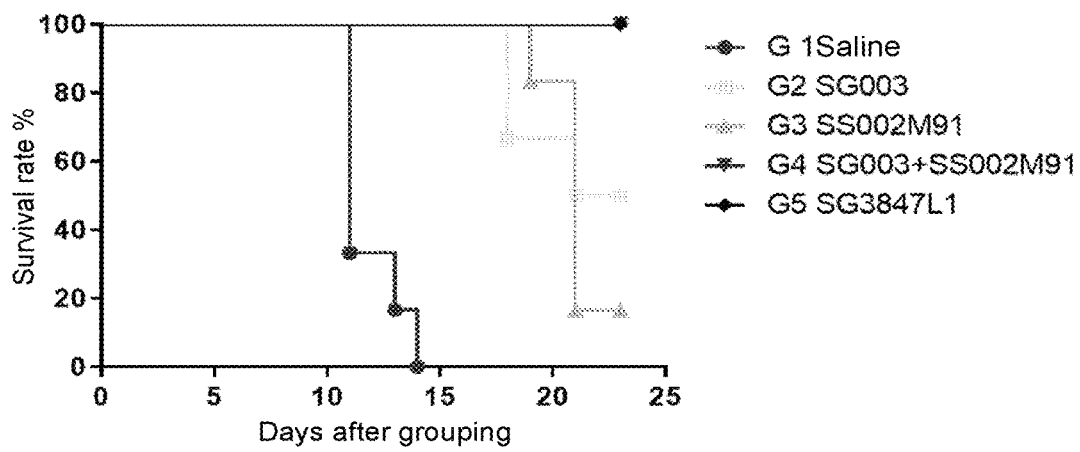
FIG. 16 shows the survival rate of mice in different treatment groups.

In addition, it can be seen from FIG. 16 that, in this drawing, "G1 saline", "G2 SG003", "G3 SS002M91", "G4 SG003+SS002M91" and "G5 SG3847L1" indicated "saline group", "SG003 antibody treatment group", "SS002M91 fusion protein treatment group", "SG003 and SS002M91 combination treatment group" and "SG3847L1 fusion protein treatment group", respectively; the median survival time in the saline group was 11 days, the median survival time in the SG003 antibody treatment group and the SS002M91 fusion protein treatment group were 22 days and 21 days respectively, indicating that SG003 and SS002M91 significantly prolonged the survival time of mice. Until 23 days after grouping, there were no death in the SG003 and SS002M91 combination treatment group and the SG3847L1 fusion protein treatment group, indicating that compared with treatment by SG003 or SS002M91 alone, the survival time of mice in the SG003 and SS002M91 combination treatment group and the SG3847L1 single treatment group are all prolonged.

The foregoing detailed description is provided by means of explanations and examples, but not intending to limit the scope of the attached claims. The various variations of the embodiments currently listed in the present application are apparent to those with ordinary skills in the art, and reserved within the scope of the attached claims and its equivalent schemes.

The invention claimed is:

1. A fusion protein, comprising:
   a first binding domain that specifically binds a tumor-associated antigen; and
   a second binding domain that specifically binds a CD47 protein;
   wherein said second binding domain comprises a mutant of a human SIRPα variant 1 domain, wherein said mutant of the human SIRPα variant 1 domain comprises an amino acid sequence as set forth in any one of SEQ ID NOs: 52, 53, 60, 61, 62 or 64.

2. The fusion protein according to claim 1, wherein said first binding domain comprises an antibody or an antigen-binding fragment thereof.

3. The fusion protein according to claim 1, wherein said tumor-associated antigen is selected from the group consisting of: CD38, AXL and Trop2.

4. The fusion protein according to claim 3, wherein the first binding domain comprises an anti-CD38 antibody or an antigen-binding fragment thereof.

5. The fusion protein according to claim 4, wherein said antibody comprises a heavy chain and a light chain of the antibody or a fragment thereof, the heavy chain of the antibody or the fragment thereof comprises HCDR1-3 and the light chain comprises LCDR1-3, the amino acid sequences of the HCDR1-3 are SEQ ID NO: 4, SEQ ID NO: 5 and SEQ ID NO: 6, successively, and the amino acid sequences of said LCDR1-3 are SEQ ID NO: 1, SEQ ID NO: 2 and SEQ ID NO: 3, successively.

6. The fusion protein according to claim 3, wherein the first binding domain comprises an anti-AXL antibody or an antigen-binding fragment thereof.

7. The fusion protein according to claim 6, wherein the antibody comprises a heavy chain and a light chain of the antibody or a fragment thereof, the heavy chain of the antibody or the fragment thereof comprises HCDR1-3, the light chain of the antibody or the fragment thereof comprises LCDR1-3, the amino acid sequences of the HCDRI-3 are SEQ ID NO: 25, SEQ ID NO: 26 and SEQ ID NO: 27, successively, and the amino acid sequences of the LCDR1-3 are SEQ ID NO: 22, SEQ ID NO: 23 and SEQ ID NO: 24, successively.

8. The fusion protein according to claim 3, wherein the first binding domain comprises an anti-Trop2 antibody or an antigen-binding fragment thereof.

9. The fusion protein according to claim 8, wherein the antibody comprises a heavy chain and a light chain of the antibody or a fragment thereof, the heavy chain of the antibody or the fragment thereof comprises HCDR1-3, and the light chain of the antibody or the fragment thereof comprise LCDR1-3, the amino acid sequences of the HCDR1-3 are SEQ ID NO: 39, SEQ ID NO: 40 and SEQ ID NO: 41, successively, and the amino acid sequences of the LCDR1-3 are SEQ ID NO: 36, SEQ ID NO: 37 and SEQ ID NO: 38, successively.

10. The fusion protein according to claim 1, wherein the first binding domain is located at N-terminal of the second binding domain.

11. The fusion protein according to claim 1, wherein the fusion protein further comprises a linker, the linker is located at C-terminal of the first binding domain and located at N-terminal of the second binding domain.

12. The fusion protein according to claim 1, comprising at least two of the second binding domains.

13. The fusion protein according to claim 12, wherein each of the second binding domains is located at C-terminal of the first binding domain respectively.

14. A composition, comprising the fusion protein according to claim 1 and a pharmaceutically acceptable excipient.

15. A method of treating a tumor or an autoimmune disease, comprising administering the fusion protein to a subject in need thereof according to claim 1.

16. The fusion protein according to claim 1, comprising a first polypeptide chain and a second polypeptide chain, wherein,
   the first polypeptide chain comprises the amino acid sequences as set forth in SEQ ID NO: 11, and the second polypeptide chain comprises the amino acid sequences as set forth in SEQ ID NO: 75,
   the first polypeptide chain comprises the amino acid sequences as set forth in SEQ ID NO: 11, and the second polypeptide chain comprises the amino acid sequences as set forth in SEQ ID NO: 76,
   the first polypeptide chain comprises the amino acid sequences as set forth in SEQ ID NO: 46, and the second polypeptide chain comprises the amino acid sequences as set forth in SEQ ID NO: 78, or
   the first polypeptide chain comprises the amino acid sequences as set forth in SEQ ID NO: 32, and the second polypeptide chain comprises the amino acid sequences as set forth in SEQ ID NO: 77.

* * * * *